US011624053B2

(12) United States Patent
Koizumi et al.

(10) Patent No.: US 11,624,053 B2
(45) Date of Patent: Apr. 11, 2023

(54) APPLICATION OF LAMININ TO CORNEAL ENDOTHELIAL CELL CULTURE

(71) Applicants: KYOTO PREFECTURAL PUBLIC UNIVERSITY CORPORATION, Kyoto (JP); ActualEyes Inc., Kyoto (JP); CorneaGen, Inc., Seattle, WA (US)

(72) Inventors: Noriko Koizumi, Kyotanabe (JP); Naoki Okumura, Kyotanabe (JP); Shigeru Kinoshita, Kyoto (JP); Friedrich E. Kruse, Erlangen (DE); Ursula Schloetzer-Schrehardt, Erlangen (DE)

(73) Assignees: KYOTO PREFECTURAL PUBLIC UNIVERSITY CORPORATION, Kyoto (JP); ActualEyes Inc., Kyotanabe (JP); CorneaGen, Inc., Seattle, WA (US)

( * ) Notice: Subject to any disclaimer, the term of this patent is extended or adjusted under 35 U.S.C. 154(b) by 0 days.

(21) Appl. No.: 15/100,147

(22) PCT Filed: Nov. 26, 2014

(86) PCT No.: PCT/JP2014/081917
§ 371 (c)(1),
(2) Date: May 27, 2016

(87) PCT Pub. No.: WO2015/080297
PCT Pub. Date: Jun. 4, 2015

(65) Prior Publication Data
US 2017/0002318 A1 Jan. 5, 2017

(30) Foreign Application Priority Data
Nov. 27, 2013 (JP) .............................. JP2013-244972

(51) Int. Cl.
*C12N 5/079* (2010.01)
*A61K 35/30* (2015.01)

(52) U.S. Cl.
CPC ............ *C12N 5/0621* (2013.01); *A61K 35/30* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 6,153,593 A | 11/2000 | Burgeson et al. | |
| 6,693,169 B1 | 2/2004 | Brunken et al. | |
| 6,933,273 B2 | 8/2005 | Tryggvason et al. | |
| 2002/0142954 A1 | 10/2002 | Burgeson et al. | |
| 2004/0106646 A1 | 6/2004 | Takayama et al. | |
| 2005/0214259 A1* | 9/2005 | Sano | A61L 27/3808 424/93.7 |
| 2007/0092550 A1 | 4/2007 | Lui | |
| 2007/0275365 A1 | 11/2007 | Lui | |
| 2008/0131430 A1 | 6/2008 | Csaky et al. | |
| 2009/0306772 A1 | 12/2009 | Tao et al. | |
| 2010/0028407 A1 | 2/2010 | Del Priore et al. | |
| 2010/0209402 A1* | 8/2010 | Koizumi | A61K 31/496 424/93.7 |
| 2010/0233240 A1 | 9/2010 | Koizumi et al. | |
| 2011/0117062 A1 | 5/2011 | Klimanskaya et al. | |
| 2012/0156254 A1 | 6/2012 | Tryggvason et al. | |
| 2012/0282324 A1 | 11/2012 | Xing et al. | |
| 2012/0288482 A1 | 11/2012 | Takahashi et al. | |
| 2013/0195806 A1 | 8/2013 | Gay et al. | |
| 2014/0170751 A1* | 6/2014 | Hayashi | C12N 5/0621 435/377 |
| 2014/0341864 A1 | 11/2014 | Nakano et al. | |
| 2014/0370007 A1* | 12/2014 | McCabe | A61K 35/30 424/133.1 |
| 2015/0025452 A1 | 1/2015 | Marinkovich et al. | |

(Continued)

FOREIGN PATENT DOCUMENTS

| | | |
|---|---|---|
| CN | 1893988 A | 1/2007 |
| CN | 102597217 A | 7/2012 |

(Continued)

OTHER PUBLICATIONS

WO2013012087-English, English translation of WO 2013/012087 (Hayashi).*
Doi et al., Recombinant Human Laminin-10, The Journal of Biological Chemistry, vol. 277, No. 15, Issue of Apr. 12, pp. 12741-12748, 2002.*
Miyazaki et al., Laminin E8 fragments support efficient adhesion and expansion of dissociated human pluripotent stem cells, Nature Communications | 3:1236 (2012).*
Aumailley et al., A simplified laminin nomenclature, Matrix Biology 24 (2005) 326-332.*
Engelmann, Isolation and Long-Term Cultivation of Human Corneal Endothelial Cells, Investigative Ophthalmology & Visual Science, vol. 29, No. 11, Nov. 1988.*

(Continued)

*Primary Examiner* — Blaine Lankford
(74) *Attorney, Agent, or Firm* — Leydig, Voit & Mayer, Ltd.

(57) ABSTRACT

The present invention provides a method of culturing corneal endothelial cells. More specifically, the present invention provides a composition for culturing or growing corneal endothelial cells, comprising at least one agent consisting of laminins and fragments thereof which express in corneal endothelial cells. Specifically, the present invention can comprise laminin 511 (alpha5 beta1 gamma1) and laminin 512 (alpha5 beta2 gamma 1). The present invention further provides a culture container for corneal endothelial cells, which is coated with the composition of the present invention. Furthermore, the present invention provides a method for culturing corneal endothelial cells comprising the step of using the composition or the container of the present invention to culture the corneal endothelial cells.

3 Claims, 14 Drawing Sheets

Specification includes a Sequence Listing.

(56) References Cited

U.S. PATENT DOCUMENTS

| | | |
|---|---|---|
| 2017/0319665 A1 | 11/2017 | Koizumi et al. |
| 2017/0319693 A1 | 11/2017 | Koizumi et al. |
| 2020/0138868 A1 | 5/2020 | Thon et al. |

FOREIGN PATENT DOCUMENTS

| | | |
|---|---|---|
| CN | 102770136 A | 11/2012 |
| CN | 103384679 A | 11/2013 |
| CN | 103931608 A | 7/2014 |
| CN | 103937738 A | 7/2014 |
| EP | 2193806 A1 | 6/2010 |
| EP | 2 487 236 A1 | 8/2012 |
| EP | 2 733 201 A1 | 5/2014 |
| JP | 2013-128474 A | 7/2013 |
| RU | 2418067 C1 | 5/2011 |
| WO | WO 2000/066731 A2 | 11/2000 |
| WO | WO 2005/037144 A2 | 4/2005 |
| WO | WO 2007/091790 A1 | 8/2007 |
| WO | WO 2012/173207 A1 | 12/2012 |
| WO | WO 2013/012087 A1 | 1/2013 |
| WO | WO 2014/087244 A2 | 6/2014 |
| WO | WO 2015/053375 A1 | 4/2015 |

OTHER PUBLICATIONS

Okumura et al., Laminin-511 and -521 enable efficient in vitro expansion of human corneal endothelial cells, IOVS, 56:2933-2942,2015 (Year: 2015).*

European Patent Office, Communication pursuant to Article 94(3) EPC in European Patent Application No. 14831100.4 (dated May 12, 2017).

Kakutani et al., "The efficiency of laminin-511 and laminin-521 as extracellular matrix for human corneal endothelial cell culture," *Investigative Ophthalmology and Visual Science*, 55: Abstract 2055 (2014) [retrieved on Mar. 19, 2015, from the Internet at URL: http://abstracts.iovs.org/cgi/content/short/55/5/2055].

Yamaguchi et al., "Adhesion, Migration, and Proliferation of Cultured Human Corneal Endothelial Cells by Laminin-5," *Investigative Ophthalmology and Visual Science*, 52(2): 679-684 (2011).

Japanese Patent Office, International Search Report in International Patent Application No. PCT/JP2014/081917 (dated Apr. 1, 2015).

European Patent Office, Communication Pursuant to Article 94(3) EPC in European Patent Application No. 14831100.4 (dated Mar. 28, 2018).

Japanese Patent Office, Official Action in Japanese Patent Application No. 2016-535065 (dated Aug. 27, 2018).

Russian Patent Office, Official Action in Russian Patent Application No. 2016125225 (dated May 28, 2018).

Russian Patent Office, Search Report in Russian Patent Application No. 2016125225 (dated May 28, 2018).

Russian Patent Office, Official Action in Russian Patent Application No. 2016125225 (dated Sep. 5, 2018).

European Patent Office, Communication Pursuant to Article 94(3) EPC in European Patent Application No. 14831100.4 (dated Dec. 18, 2018).

Brazilian Patent Office, Office Action in Brazilian Patent Application No. BR112016011096-0 (dated Nov. 4, 2019).

Mexican Patent Office, Office Action in Mexican Patent Application No. MX/a/2016/006915 (dated Jun. 20, 2019).

Russian Patent Office, Official Action in Russian Patent Application No. 2017118405 (dated May 31, 2019).

Deutzmann et al., "Cell adhesion, spreading and neurite stimulation by laminin fragment E8 depends on maintenance of secondary and tertiary structure in its rod and globular domain," *Eur. J. Biochem.*, 191: 513-522 (1990).

Caissie et al., "In vivo enhancement of sensory perception recovery in a tissue-engineered skin enriched with laminin," *Biomaterials*, 27: 2988-2993 (2006).

Liebkind et al., "Is the Soluble KDI Domain of γ1 Laminin a Regeneration Factor for the Mammalian Central Nervous System?" *J. Neurosci. Res.*, 73: 637-643 (2003).

McMillan et al., "Colocalization of Multiple Laminin Isoforms Predominantly beneath Hemidesmosomes in the Upper Lamina Densa of the Epidermal Basement Membrane," *J. Histochem. Cytochem.*, 54(1): 109-118 (2006).

Menezes et al., "Polylaminin, a polymeric form of laminin, promotes regeneration after spinal cord injury," *FASEB J.*, 24: 4513-4522 (2010).

Plantman et al., "Integrin-laminin interactions controlling neurite outgrowth from adult DRG neurons in vitro," *Mol. Cell. Sci.*, 39: 50-62 (2008).

Chinese Patent Office, Second Office Action in Chinese Patent Application No. 201480065134.X (dated Jul. 3, 2019).

Europen Patent Office, Communication Pursuant to Article 94(3) EPC in European Patent Application No. 15854105.2 (dated Oct. 14, 2019).

Koizumi, "Development of New Therapeutic Modalities for Corneal Endothelial Disease Using Somatic Stem Cells", *Journal of Clinical and Experimental Medicine*, 241 (10): 765-770 (2012).

Li et al., "Relevance Between Proliferation of Corneal Endothelial Celland Cytoskeleton Under the Action of Laminin," *Ophthalmic Research*, 23(1): 29 (2005).

Numata et al., "Usefulness of Laminins 511 and 521 as Culture Substrates for Human Endothelial Cells", *Japan Cornea Conference 2014: 38th Japan Cornea Society and 30th Annual Meeting of Keratoplasty Society of Japan Program Shorokushu*, p. 82, abstract 038 (Jan. 31, 2014).

Okamoto et al., "Chapter 3 Strategies Toward Clinical Uses and Front-Line—Toward Drug Discovery and Establishment of Multicellular Bodies", *Experimental Medicine*, 30(10): 1646-1650 (2012).

Okumura et al., "Usefulness of Laminins 511 and 521 in Culture of Corneal Endothelial Cells", *Regenerative Medicine*, 13 (Suppl. 2014): 243, abstract O-44-1 (Jan. 27, 2014).

Sekiguchi et al., "Laminin-511 E8 Fragment as a Culture Substrate for Human Pluripotent Stem Cells Under Feeder-Free/Xeno-Free Conditions", *Clinical Evaluation*, 41(1): 124-127 (2013).

Sekiguchi et al., "Fundamental Technique for the Spread of Regenerative Medicine", *Saishin Igaku*, 69: 685-697 (Mar. 2014).

Ueno et al., "Realization of Regenerative Medicine for Corneal Endothelium by Transplantation of Cultured Human Corneal Endothelial Cells", *Inflammation and Immunology*, 21(2): 131-135 (2013).

Chinese Patent Office, First Office Action in Chinese Patent Application No. 201480065134X (dated Feb. 3, 2019).

Chinese Patent Office, Search Report in Chinese Patent Application No. 201480065134X (dated Feb. 3, 2019).

European Patent Office, Communication Pursuant to Rule 164(1) EPC in European Patent Application No. 15854105.2 (dated Jun. 11, 2018).

European Patent Office, Extended European Search Report in European Patent Application No. 15854129.2 (dated May 4, 2018).

Japanese Patent Office, International Search Report in International Patent Application No. PCT/JP2015/005473 (dated Dec. 8, 2015).

Japanese Patent Office, International Search Report in International Patent Application No. PCT/JP2015/005474 (dated Dec. 8, 2015).

Russian Patent Office, Notification of Official Action in Russian Patent Application No. 2016125225 (dated Jan. 22, 2019).

Colby et al., "Medical Treatment of Fuchs' Dystrophy in our Lifetime?" *Invest. Ophthalmol. Vis. Sci.*, 54(4): 2503 (2013).

Davis et al., "Regulation of Tissue Injury Responses by the Exposure of Matricryptic Sites within Extracellular Matrix Molecules," *Am. J. Pathol.*, 156(5): 1489-1498 (2000).

Kaufman, "The corneal endothelium in intraocular surgery," *J. R. Soc. Med.*, 73(3): 165-171 (1980).

Kerafast, "Human Laminin 332," Catalog No. EUV102 and EUV103 (2019).

Medline, "Fuchs' dystrophy," *MedlinePlus Medical Encyclopedia* (2015) [obtained at http://www.nlm.nih.gov/medlineplus/ency/article/007295.htm on Oct. 18, 2019].

Japanese Patent Office, Office Action in Japanese Patent Application No. 2016-556373 (dated Aug. 2, 2019).

Japanese Patent Office, Office Action in Japanese Patent Application No. 2016-556374 (dated Aug. 2, 2019).

(56) References Cited

OTHER PUBLICATIONS

Huang et al., "A Hierarchy of Endothelial Colony—Forming Cell Activity Displayed by Bovine Corneal Endothelial Cells," *Invest. Ophthalmol. Vis. Sci.*, 51(8): 3943-3949 (2010).
Japanese Patent Office, Notice of Reasons for Refusal in Japanese Patent Application No. 2016-556374 (dated Mar. 3, 2020).
Miner et al., "Laminin Functions in Tissue Morphogenesis," *Annu. Rev. Cell Dev. Biol.*, 20: 255-284 (2004).
Yan et al., "III. Repair of Corneal endothelial Wound," *Ocular Physiology*, 46-47 (Dec. 31, 2001).
Zheng, "VI. Research progress of corneal endothelial transplantation," *Ophthalmological Clinical Theory and Practice*, 87-88 (Oct. 31, 1998).
China National Intellectual Property Administration, Third Office Action in Chinese Patent Application No. 201580059642.1 (dated Jan. 4, 2021).
Japanese Patent Office, Inquiry in Appeal No. 2020-7637 for Japanese Patent Application No. 2016-556373 (Apr. 9, 2021).
Japanese Patent Office, Notice of Reasons for Rejection in Appeal No. 2020-7637 for Japanese Patent Application No. 2016-556373 (dated Apr. 9, 2021).
European Patent Office, Communication Pursuant to Article 94(3) EPC in European Patent Application No. 15854129.2 (dated Mar. 9, 2021).
European Patent Office, Communication Pursuant to Article 94(3) EPC in European Patent Application No. 15854105.2 (dated May 12, 2020).
Brazilian Patent Office, Preliminary Office Action in Brazilian Patent Application No. BR112017008805-3 (dated Aug. 13, 2020).
China National Intellectual Property Administration, Second Office Action in Chinese Patent Application No. 201580059642.1 (dated Sep. 2, 2020).
Mexican Patent Office, Office Action in Mexican Patent Application No. MX/a/2017/005522 (dated Sep. 17, 2020).
Bystrom et al., "Distribution of Laminins in the Developing Human Eye," *Invest. Ophthalmol Vis. Sci.*, 47(3): 777-785 (2006).
Osumi et al., "Concise Review: Pax6 Transcription Factor Contributes to both Embryonic and Adult Neurogenesis as a Multifunctional Regulator," *Stem Cells*, 26(7): 1663-1672 (2008).
Powell et al., "Neuronal Laminins and their Cellular Receptors," *Int. J. Biochem. Cell Biol.*, 29(3): 401-414 (1997).
China National Intellectual Property Administration, Decision of Rejection in Chinese Patent Application No. 201580059642.1 (dated Apr. 21, 2021).
Mexican Patent Office, Office Action in Mexican Patent Application No. MX/a/2017/005522 (dated Apr. 15, 2021).
Novus Biologicals, "Laminin Antibody," Catalog Entry NB300-144 (2022).
Takizawa et al., "Mechanistic basis for the recognition of laminin-511 by α6β1 integrin," *Sci. Adv.*, 3(9): e170497 (2017).
Farina et al., "Temporal proteomic profiling of embryonic stem cell secretome during cardiac and neural differentiation," *Proteomics*, 11 (20): 3972-3982 (2011).
Gospodarowicz et al., "The Production and Localization of Laminin in Cultured Vascular and Corneal Endothelial Cells," *J. Cell. Phys.*, 107(2): 171-183 (1981).
Taniguchi et al., "The C-terminal Region of Laminin β Chains Modulates the Integrin Binding Affinities of Laminins," *J. Biol. Chem.*, 284(12): 7820-7831 (2009).
China National Intellectual Property Administration, First Office Action and Search Report in Chinese Patent Application No. 201580059642.1 (dated Feb. 3, 2020).
European Patent Office, Communication Pursuant to Article 94(3) EPC in European Patent Application No. 15854129.2 (dated Jan. 28, 2020).
Japanese Patent Office, Final Office Action in Japanese Patent Application No. 2016-556373 (dated Mar. 3, 2020).
Canadian Patent Office, Examination Report and Search Report in Canadian Patent Application No. 2,965,770 (dated Oct. 20, 2021).
Japanese Patent Office, Notice of Reasons for Refusal in Japanese Patent Application No. 2020-097055 (dated Oct. 6, 2021).
Edwards et al., "Laminins and retinal vascular development," *Cell Adhesion and Migration*, 7(1): 82-89 (2013).
Suzuki et al., "Functional Sites in the Laminin Alpha Chains," *Connective Tissue Research*, 46(3): 142-152 (2005).
Japanese Patent Office, Decision of Refusal in Japanese Patent Application No. 2020-097055 (dated Feb. 15, 2022).
U.S. Appl. No. 15/523,231, filed Ap. 28, 2017.
U.S. Appl. No. 15/523,282, filed Apr. 28, 2017.
Thoughtco, "Suspension Definition in Chemistry" [accessed on Aug. 26, 2022 at https://www.thoughtco.com/definition-of-suspension-605714] (2022).
Okumura et al., "Enhancement on Primate Corneal Endothelial Cell Survival In Vitro by a Rock Inhibitor," *Invest. Ophthalmol. Vis. Sci.*, 50(8): 3680-3687 (2009).
Canadian Intellectual Property Office, Examiner Requisition in Canadian Patent Application No. 2,965,770 (dated Nov. 2, 2022).

* cited by examiner

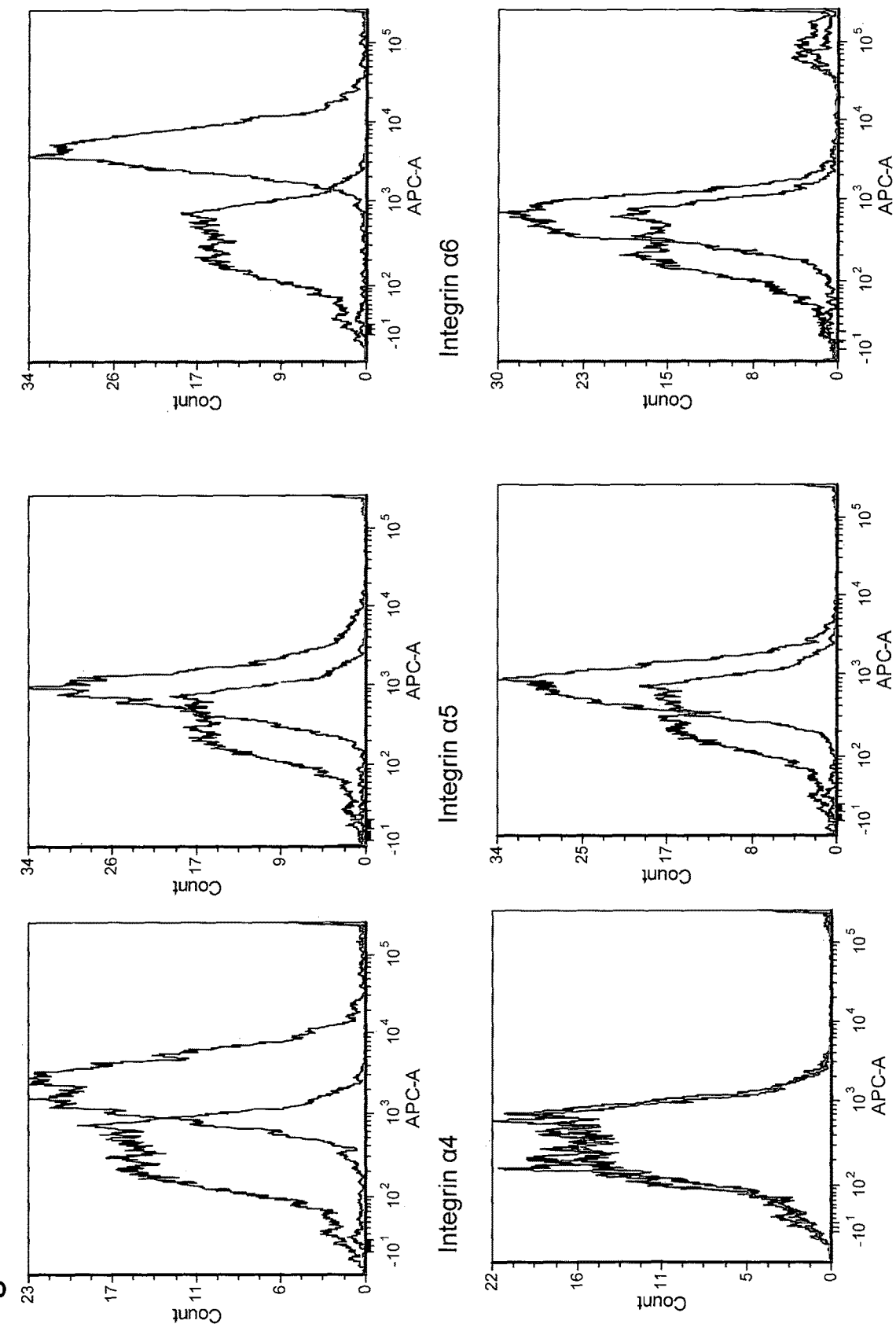

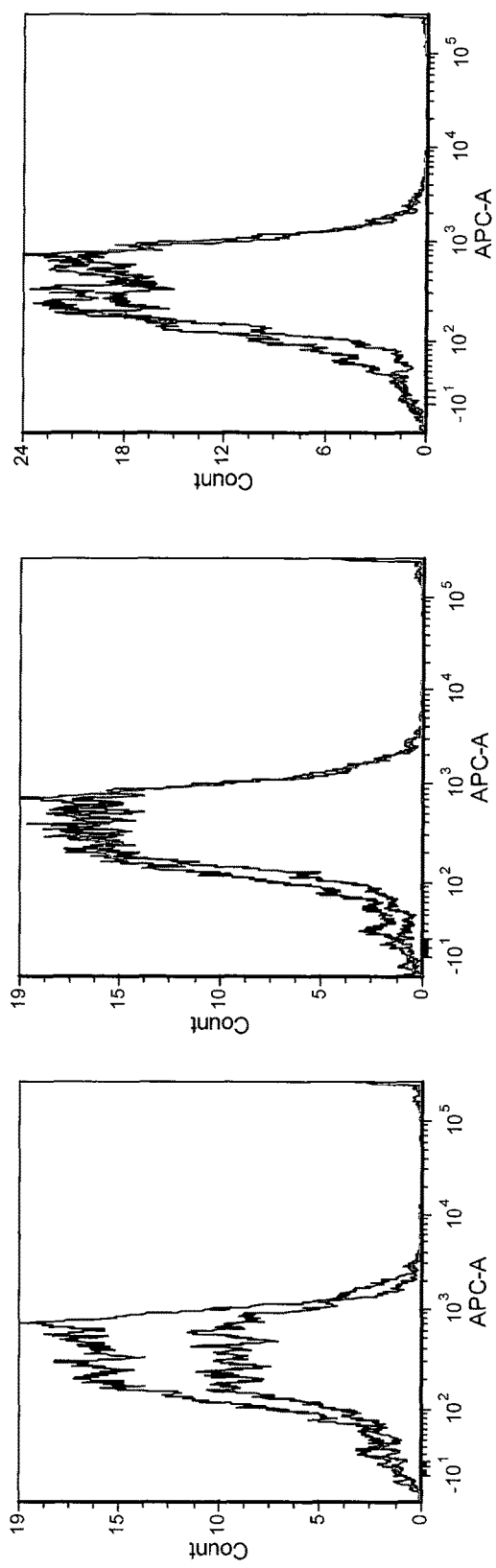
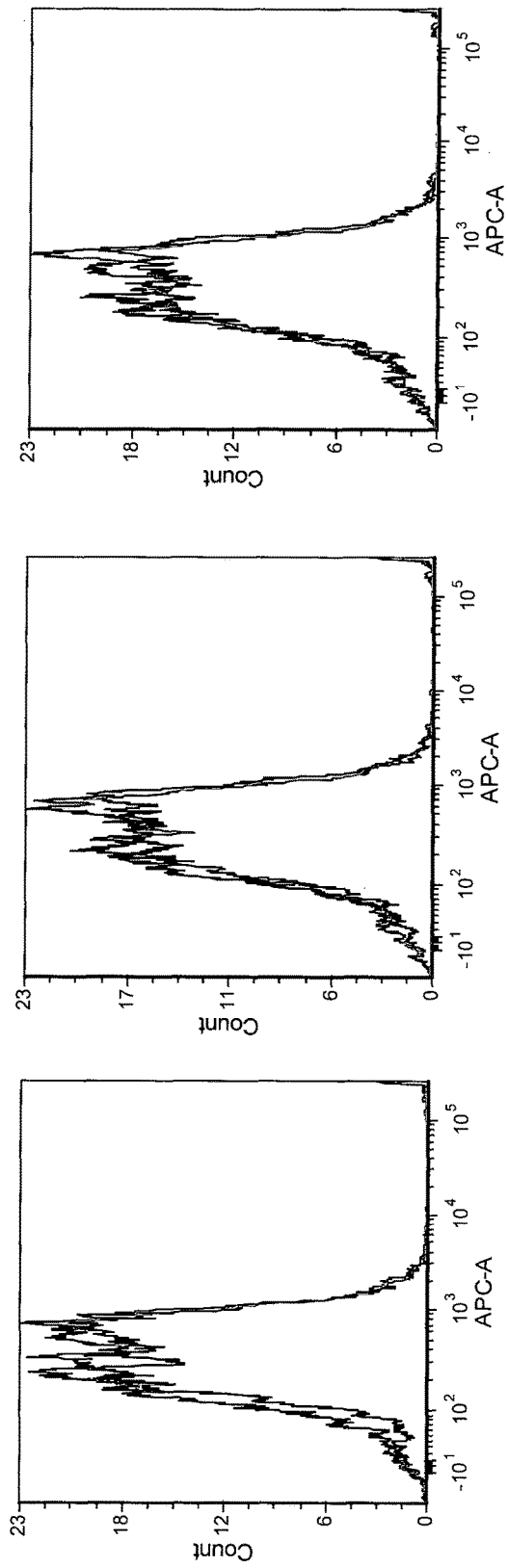
Fig. 3B

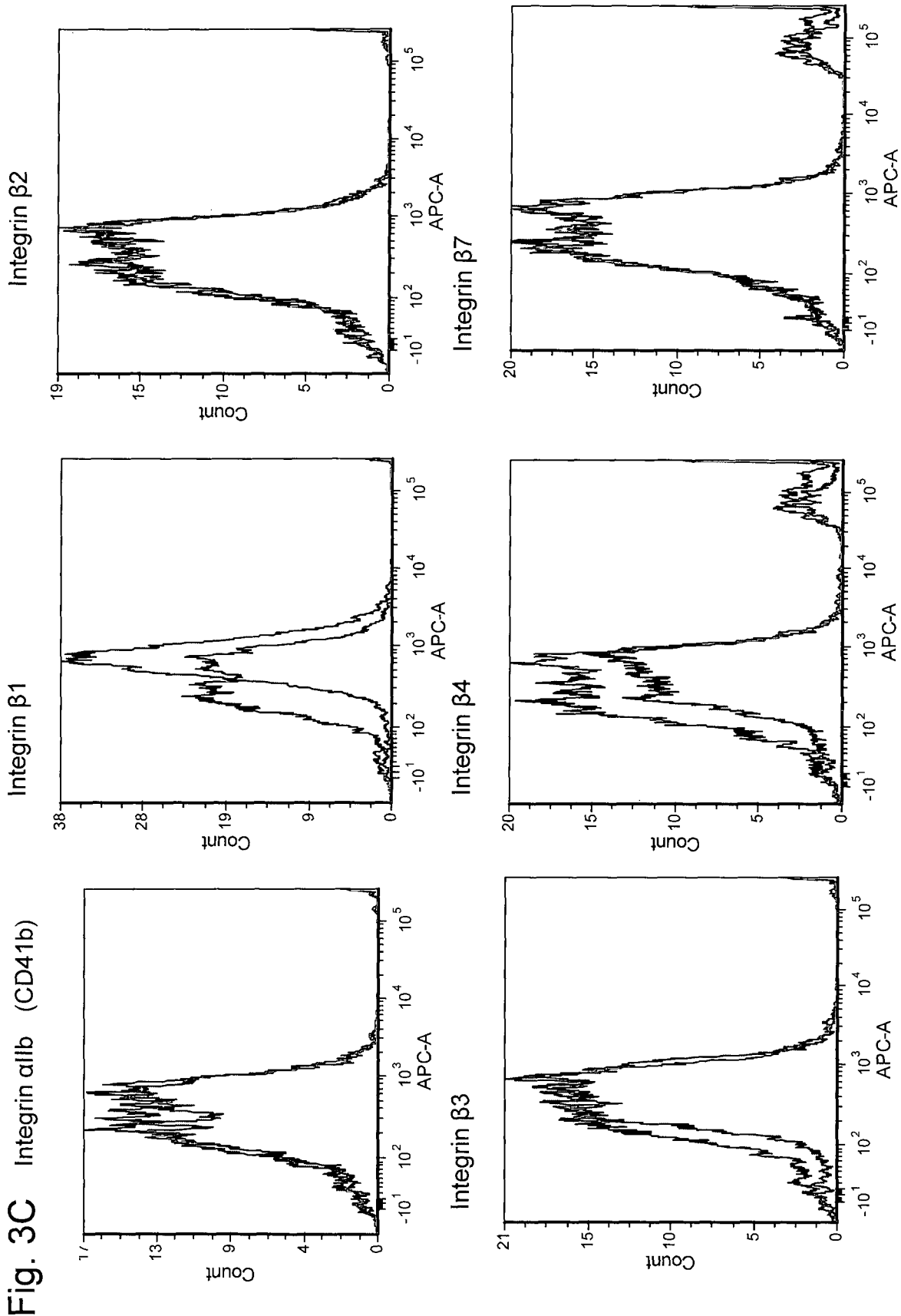

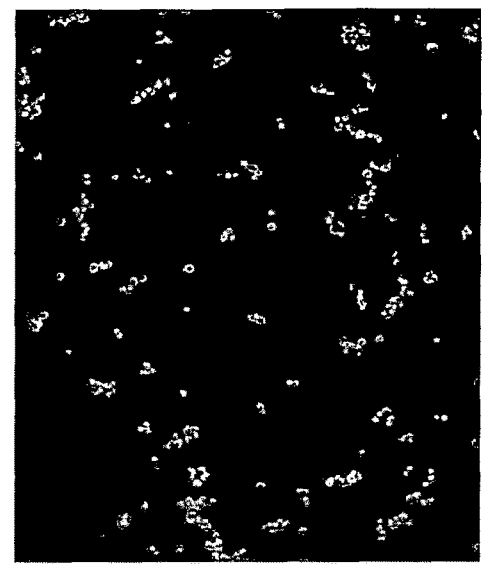
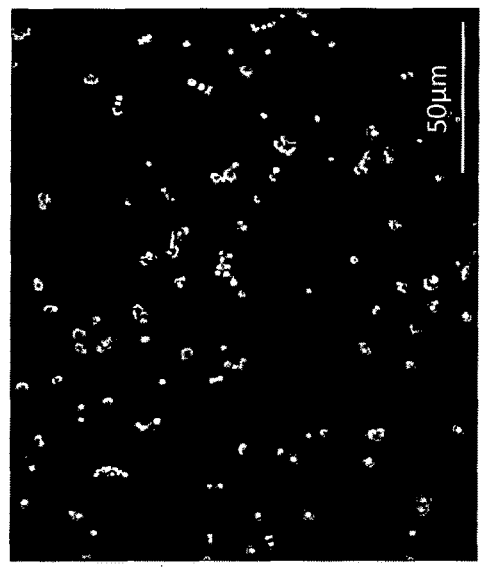
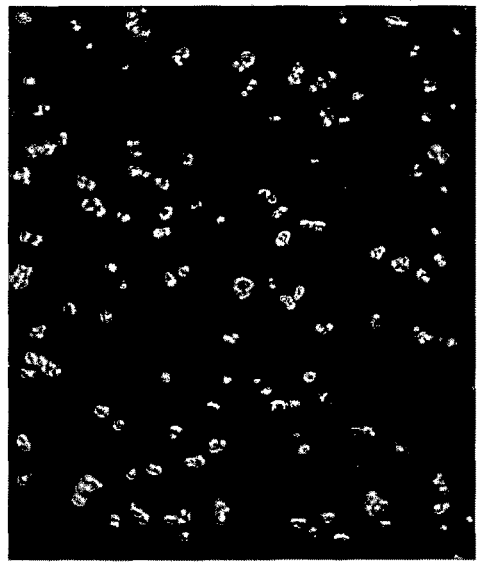
Fig. 4

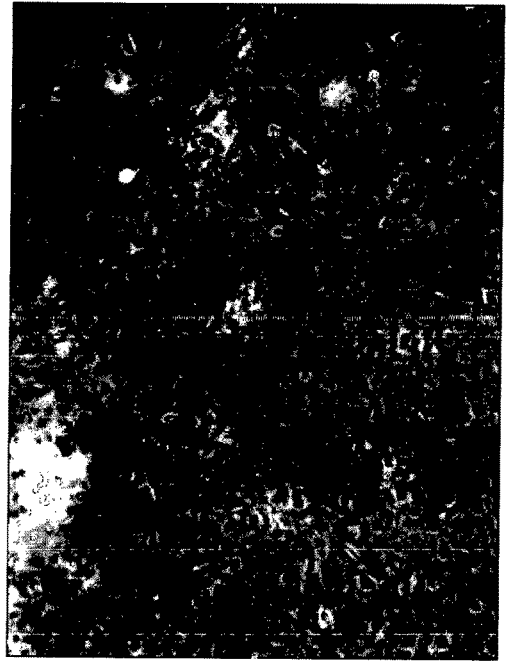
Fig. 8

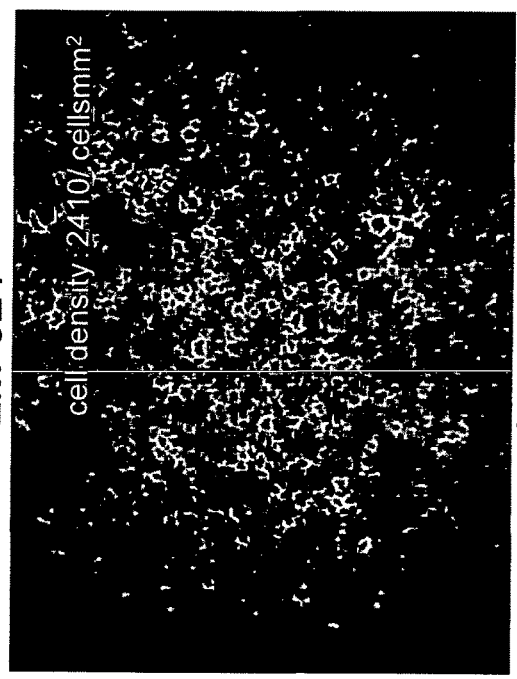 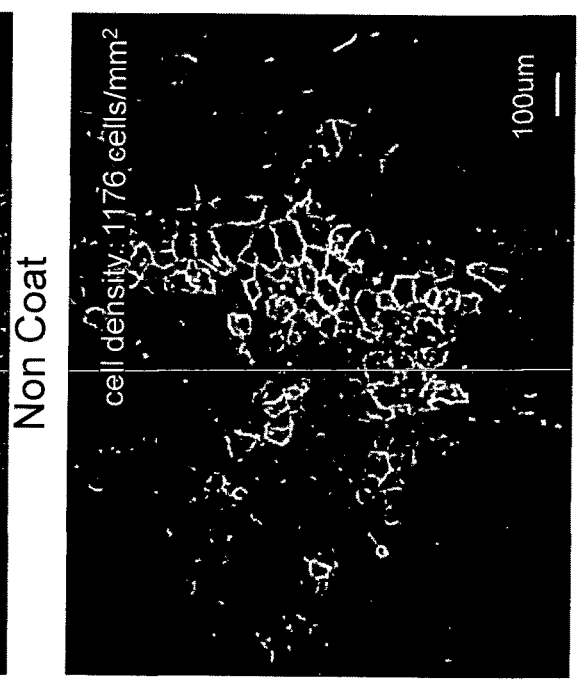
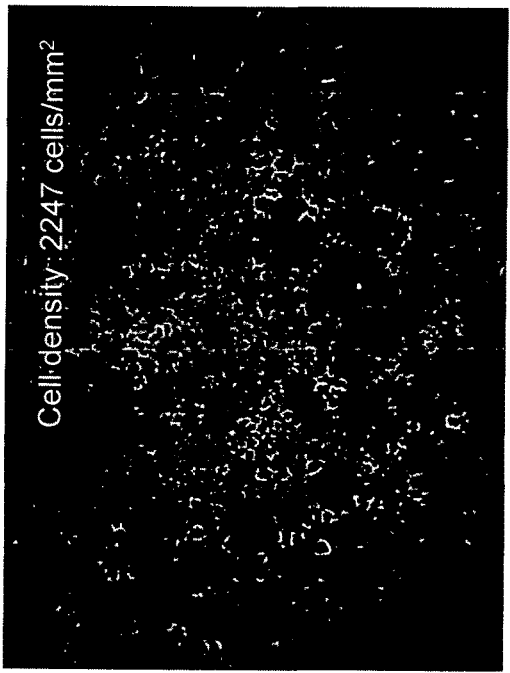 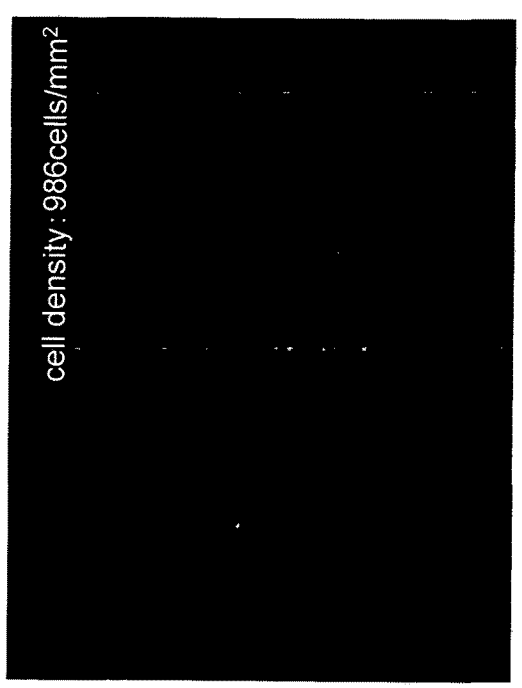
Fig. 10

SEQUENCE LISTING

```
<160> NUMBER OF SEQ ID NOS: 86

<210> SEQ ID NO 1
<211> LENGTH: 11445
<212> TYPE: DNA
<213> ORGANISM: Homo sapiens

<400> SEQUENCE: 1
agacccgccg ggctcccgcc gcgcgcgctg tccctggagc tcggggacgc ggcccggagc     60
cgggaagatg gcgaagcggc tctgcgcggg gagcgcactg tgtgttcgcg gccccgggg    120 ccccgcgccg ctgctgctgg tcgggctggc gctgctgggc gcggcgcggg cgcgggagga   180
```

```
ggcgggcggc ggcttcagcc tgcacccgcc ctacttcaac ctggccgagg gcgcccgcat      240
cgccgcctcc gcgacctgcg gagaggaggc cccggcgcgc ggctccccgc gccccaccga      300
ggacctttac tgcaagctgg taggggggccc cgtggccggc ggcgacccca accagaccat     360
ccggggccag tactgtgaca tctgcacggc tgccaacagc aacaaggcac accccgcgag      420
caatgccatc gatggcacgg agcgctggtg gcagagtcca ccgctgtccc gcggcctgga      480
gtacaacgag gtcaacgtca ccctggacct gggccaggtc ttccacgtgg cctacgtcct      540
catcaagttt gccaactcac cccggccgga cctctgggtg ctggagcggt ccatggactt      600
cggccgcacc taccagccct ggcagttctt tgcctcctcc aagagggact gtctggagcg      660
gttcgggcca cagacgctgg agcgcatcac acgggacgac gcggccatct gcaccaccga      720
gtactcacgc atcgtgcccc tggagaacgg agagatcgtg gtgtccctgg tgaacgacg      780 tccgggcgcc atgaatttct cctactcgcc gctgctacgt gagttcacca aggccaccaa      840
cgtccgcctg cgcttcctgc gtaccaacac gctgctgggc catctcatgg ggaaggcgct      900
gcgggacccc acggtcaccc gccggtatta ttacagcatc aaggatatca gcatcggagg      960
ccgctgtgtc tgccacggcc acgcggatgc ctgcgatgcc aaagaccccca cggacccgtt     1020 caggctgcag tgcacctgcc agcacaacac ctgcgggggc acctgcgacc gctgctgccc      1080
cggcttcaat cagcagccgt ggaagcctgc gactgccaac agtgccaacg agtgccagtc      1140
ctgtaactgc tacggccatg ccaccgactg ttactacgac cctgaggtgg accggcgccg      1200
cgccagccag agcctggatg gcacctatca gggtgggggt gtctgtatcg actgccagca      1260
ccacaccacc ggcgtcaact gtgagcgctg cctgccggc ttctaccgct ctcccaacca      1320
ccctctcgac tcgccccacg tctgccgccg ctgcaactgc gagtccgact tcacggatgg      1380
cacctgcgag gacctgacgg gtcgatgcta ctgccggccc aacttctctg ggagcggtg     1440 tgacgtgtgt gccgagggct tcacgggctt cccaagctgc tacccgacgc cctcgtcctc      1500
caatgacacc agggagcagg tgctgccagc cggccagatt gtgaattgtg actgcagcgc      1560
ggcagggacc cagggcaacg cctgccggaa ggacccaagg gtgggacgct gtctgtgcaa      1620
acccaacttc caaggcaccc attgtgagct ctgcgcgcca gggttctacg gccccggctg      1680
ccagccctgc cagtgttcca gccctggagt ggccgatgac cgctgtgacc ctgacacagg      1740
ccagtgcagg tgccgagtgg gcttcgaggg ggccacatgt gatcgctgtg cccccggcta      1800
ctttcacttc cctctctgcc agttgtgtgg ctgcagccct gcaggaacct tgcccgaggg      1860
ctgcgatgag gccggccgct gcctatgcca gcctgagttt gctggacctc attgtgaccg      1920
gtgccgccct ggctaccatg gtttccccaa ctgccaagca tgcacctgcg accctcgggg      1980
agccctggac cagctctgtg gggcgggagg tttgtgccgc tgccgcccccg gctacacagg      2040 cactgcctgc caggaatgca gccccggctt tcacggcttc cccagctgtg tccctgcca      2100 ctgctctgct gaaggctccc tgcacgcagc ctgtgacccc cggagtgggc agtgcagctg      2160
ccggccccgt gtgacgggc tgcggtgtga cacatgtgtg cccggtgcct acaacttccc      2220
ctactgcgaa gctggctctt gccaccctgc cggtctggcc ccagtggatc ctgcccttcc      2280
tgaggcacag gttccctgta tgtgccgggc tcacgtggag gggccgagct gtgaccgctg      2340
caaacctggg ttctggggac tgagccccag caaccccgag ggctgtaccc gctgcagctg      2400
cgacctcagg ggcacactgg gtggagttgc tgagtgccag ccgggcaccg gccagtgctt      2460
ctgcaagccc cacgtgtgcg gccaggcctg cgcgtcctgc aaggatggct tctttggact      2520
ggatcaggct gactattttg gctgccgcag ctgccggtgt gacattggcg gtgcactggg      2580
```

```
ccagagctgt gaaccgagga cgggcgtctg ccggtgccgc cccaacaccc agggccccac    2640
ctgcagcgag cctgcgaggg accactacct cccggacctg caccacctgc gcctggagct    2700
ggaggaggct gccacacctg agggtcacgc cgtgcgcttt ggcttcaacc ccctcgagtt    2760
cgagaacttc agctggaggg gctacgcgca gatggcacct gtccagccca ggatcgtggc    2820
caggctgaac ctgacctccc ctgaccttt ctggctcgtc ttccgatacg tcaaccgggg    2880
ggccatgagt gtgagcgggc gggtctctgt gcgagaggag ggcaggtcgg ccacctgcgc    2940
caactgcaca gcacagagtc agcccgtggc cttcccaccc agcacggagc ctgccttcat    3000
caccgtgccc cagaggggct tcggagagcc ctttgtgctg aaccctggca cctgggccct    3060
gcgtgtggag gccgaagggg tgctcctgga ctacgtggtt ctgctgccta gcgcatacta    3120
cgaggcggcg ctcctgcagc tgcgggtgac tgaggcctgc acataccgtc cctctgccca    3180
gcagtctggc gacaactgcc tcctctacac acacctcccc ctggatggct tccctcggc    3240 cgccgggctg gaggccctgt gtcgccagga caacagcctg ccccggccct gccccacgga    3300
gcagctcagc ccgtcgcacc cgccactgat cacctgcacg ggcagtgatg tggacgtcca    3360
gcttcaagtg gcagtgccac agccaggccg ctatgcccta gtggtggagt acgccaatga    3420
ggatgcccgc caggaggtgg gcgtggccgt gcacacccca cagcgggccc cccagcaggg    3480
gctgctctcc ctgcacccct gcctgtacag caccctgtgc cggggcactg cccgggatac    3540
ccaggaccac ctggctgtct tccacctgga ctcggaggcc agcgtgaggc tcacagccga    3600
acaggcacgc ttcttcctgc acgggtcac tctggtgccc attgaggagt tcagcccgga    3660
gttcgtggag ccccgggtca gctgcatcag cagccacggc gcctttggcc ccaacagtgc    3720
cgcctgtctg ccctcgcgct tcccaaagcc gccccagccc atcatcctca gggactgcca    3780
ggtgatcccg ctgccgcccg gcctcccgct gacccacgcg caggatctca ctccagccat    3840
gtccccagct ggaccccgac ctcggccccc caccgctgtg gacctgatg cagagcccac    3900 cctgctgcgt gagcccagg ccaccgtggt cttcaccacc catgtgccca cgctgggccg    3960
ctatgccttc ctgctgcacg gctaccagc agcccacccc accttcccg tggaagtcct    4020 catcaacgcc ggccgcgtgt ggcagggcca cgccaacgcc agcttctgtc cacatggcta    4080
cggctgccgc accctggtgg tgtgtgaggg ccaggccctg ctggacgtga cccacagcga    4140
gctcactgtg accgtgcgtg tgcccaaggg ccggtggctc tggctggatt atgtactcgt    4200
ggtccctgag aacgtctaca gctttggcta cctccgggag gagcccctgg ataaatccta    4260
tgacttcatc agccactgcg cagcccaggg ctaccacatc agcccagca gctcatccct    4320 gttctgccga aacgctgctg cttccctctc cctcttctat aacaacggag cccgtccatg    4380
tggctgccac gaagtaggtg ctacaggccc cacgtgtgag cccttcgggg gccagtgtcc    4440
ctgccatgcc catgtcattg gccgtgactg ctcccgctgt gccaccggat actggggctt    4500
ccccaactgc aggccctgtg actgcggtgc ccgcctctgt gacgagctca cgggccagtg    4560
catctgcccg ccacgcacca tccgcccga ctgcctgctg tgccagcccc agaccttgg    4620 ctgccacccc ctggtcggct gtgaggagtg taactgctca gggcccggca tccaggagct    4680
cacagaccct acctgtgaca cagacagcgg ccagtgcaag tgcagaccca acgtgactgg    4740
gcgccgctgt gatacctgct ccggggctt ccatggctac cccgctgcc gccctgtga    4800 ctgtcacgag gcgggcactg cgcctggcgt gtgtgacccc tcacagggc agtgctactg    4860 taaggagaac gtgcagggcc ccaaatgtga ccagtgcagc cttgggacct tctcactgga    4920
```

```
tgctgccaac cccaaaggtt gcacccgctg cttctgcttt ggggccacgg agcgctgccg    4980
gagctcgtcc tacacccgcc aggagttcgt ggatatggag ggatgggtgc tgctgagcac    5040
tgaccggcag gtggtgcccc acgagcggca gccagggacg gagatgctcc gtgcagacct    5100
gcggcacgtg cctgaggctg tgcccgaggc tttccccgag ctgtactggc aggccccacc    5160
ctcctacctg ggggaccggg tgtcatccta cggtgggacc ctccgttatg aactgcactc    5220
agagacccag cggggagatg tctttgtccc catggagagc aggccggatg tggtgctgca    5280
gggcaaccag atgagcatca cattcctgga gccggcatac cccacgcctg ccacgttca    5340 ccgtgggcag ctgcagctgg tggaggggaa cttccggcat acggagacgc gcaacactgt    5400
gtcccgcgag gagctcatga tggtgctggc cagcctggag cagctgcaga tccgtgccct    5460
cttctcacag atctcctcgg ctgtcttcct gcgcagggtg gcactggagg tggccagccc    5520
agcaggccag ggggccctgg ccagcaatgt ggagctgtgc ctgtgccccg ccagctaccg    5580
gggggactca tgccaggaat gtgccccgg cttctatcgg gacgtcaaag gtctcttcct    5640
gggccgatgt gtcccttgtc agtgccatgg acactcagac cgctgcctcc ctggctctgg    5700
cgtctgtgtg gactgccagc acaacaccga aggggcccac tgtgagcgct gccaggctgg    5760
cttcgtgagc agcagggacg accccagcgc ccctgtgtc agctgcccct gcccctctc    5820 agtgccttcc aacaacttcg ccgagggctg tgtcctgcga ggcggccgca cccagtgcct    5880
ctgcaaacct ggttatgcag gtgcctcctg cgagcggtgt gcgcccggat tctttgggaa    5940
cccactggtg ctgggcagct cctgccagcc atgcgactgc agcggcaacg gtgaccccaa    6000
cttgctcttc agcgactgcg accccctgac gggcgcctgc cgtggctgcc tgcgccacac    6060
cactgggccc cgctgcgaga tctgtgcccc cggcttctac ggcaacgccc tgctgcccgg    6120
caactgcacc cggtgcgact gtaccccatg tgggacagag gcctgcgacc ccacagcgg    6180 gcactgcctg tgcaaggcgg gcgtgactgg gcggcgctgt gaccgctgcc aggagggaca    6240
ttttggtttc gatggctgcg ggggctgccg ccgtgtgct tgtggaccgg ccgccgaggg    6300
ctccgagtgc caccccagag gcggacagtg ccactgccga ccagggacca tgggaccca    6360 gtgccgcgag tgtgccccctg gctactgggg gctccctgag cagggctgca ggcgctgcca    6420
gtgccctggg ggccgctgtg accctcacac gggccgctgc aactgccccc cggggctcag    6480
cggggagcgc tgcgacacct gcagccagca gcatcaggtg cctgttccag gcgggcctgt    6540
gggccacagc atccactgtg aagtgtgtga ccactgtgtg gtcctgctcc tggatgacct    6600
ggaacgggcc ggcgcctcc tccccgccat tcacgagcaa ctgcgtggca tcaatgccag    6660
ctccatggcc tgggcccgtc tgcacaggct gaacgcctcc atcgctgacc tgcagagcca    6720
gctccggagc cccctgggcc cccgccatga cacggcacag cagctggagg tgctggagca    6780
gcagagcaca agcctcgggc aggacgcacg gcggctaggc ggccaggccg tggggacccg    6840
agaccaggcg agccaattgc tggccggcac cgaggccaca ctgggccatg cgaagacgct    6900
gttggcggcc atccgggctg tggaccgcac cctgagcgag ctcatgtccc agacgggcca    6960
cctggggctg gccaatgcct cggctccatc aggtgagcag ctgctccgga cactggccga    7020 ggtgagcgg ctgctctggg agatgcgggc ccggacctg ggggcccgc aggcagcagc    7080 tgaggctgag ttggctgcag cacagagatt gctggcccgg gtgcaggagc agctgagcag    7140
cctctgggga gagaaccagg cactggccac acaaacccgc gaccggctgg cccagcacga    7200
ggccggcctc atgaccctgc gagaggcttt gaacccgggca gtggacgcca cacgggaggc    7260
ccaggagctc aacagccgca accaggagcg cctggaggaa gccctgcaaa ggaagcagga    7320
```

```
gctgtcccgg gacaatgcca ccctgcaggc cactctgcat gcggctaggg acacctggc    7380 cagcgtcttc agattgctgc acagcctgga ccaggctaag gaggagctgg agcgcctcgc   7440
cgccagcctg gacggggctc ggaccccact gctgcagagg atgcagacct tctccccggc   7500
gggcagcaag ctgcgtctag tggaggccgc cgaggcccac gcacagcagc tgggccagct   7560
ggcactcaat ctgtccagca tcatcctgga cgtcaaccag gaccgcctca cccagagggc   7620
catcgaggcc tccaacgcct acagccgcat cctgcaggcc gtgcaggctg ccgaggatgc   7680
tgctggccag gccctgcagc aggcggacca cacgtgggcg acggtggtgc ggcagggcct   7740
ggtggaccga gcccagcagc tcctggccaa cagcactgca ctagaagagg ccatgctcca   7800
ggaacagcag aggctgggcc ttgtgtgggc tgccctccag ggtgccagga cccagctccg   7860
agatgtccgg gccaagaagg accagctgga ggcgcacatc caggcggcgc aggccatgct   7920
tgccatggac acagacgaga caagcaagaa gatcgcacat gccaaggctg tggctgctga   7980
agcccaggac accgccaccc gtgtgcagtc ccagctgcag gccatgcagg agaatgtgga   8040
gcggtggcag ggccagtacg agggcctgcg ggccaggac ctgggccagg cagtgcttga    8100
cgcaggccac tcagtgtcca ccctggagaa gacgctgccc cagctgctgg ccaagctgag   8160
catcctggag aaccgtgggg tgcacaacgc cagcctggcc ctgtccgcca gcattggccg   8220
cgtgcgagag ctcattgccc aggcccgggg ggctgccagt aaggtcaagg tgcccatgaa   8280
gttcaacggg cgctcagggg tgcagctgcg caccccacgg gatcttgccg accttgctgc   8340
ctacactgcc ctcaagttct acctgcaggg cccagagcct gagcctgggc agggtaccga   8400
ggatcgcttt gtgatgtaca tgggcagccg ccaggccact ggggactaca tgggtgtgtc   8460
tctgcgtgac aagaaggtgc actgggtgta tcagctgggt gaggcgggcc ctgcagtcct   8520
aagcatcgat gaggacattg gggagcagtt cgcagctgtc agcctggaca ggactctcca   8580
gtttggccac atgtccgtca cagtggagag acagatgatc caggaaacca agggtgacac   8640
ggtggcccct ggggcagagg ggctgctcaa cctgcggcca gacgacttcg tcttctacgt   8700 cgggggggtac cccagtacct tcacgccccc tcccctgctt cgcttccccg gctaccgggg   8760
ctgcatcgag atggacacgc tgaatgagga ggtggtcagc ctctacaact cgagaggac    8820 cttccagctg gacacggctg tggacaggcc ttgtgcccgc tccaagtcga ccggggaccc   8880
gtggctcacg gacggctcct acctggacgg caccggcttc gcccgcatca gcttcgacag   8940
tcagatcagc accaccaagc gcttcgagca ggagctgcgg ctcgtgtcct acagcggggt   9000
gctcttcttc ctgaagcagc agagccagtt cctgtgcttg gccgtgcaag aaggcagcct   9060
cgtgctgttg tatgactttg gggctggcct gaaaaaggcc gtcccactgc agccccacc    9120 gccccctgacc tcggccagca aggcgatcca ggtgttcctg ctgggggca gccgcaagcg    9180 tgtgctggtg cgtgtggagc gggccacggt gtacagcgtg gagcaggaca atgatctgga   9240
gctggccgac gcctactacc tggggggcgt gccgcccgac cagctgcccc cgagcctgcg   9300
acggctcttc cccaccggag gctcagtccg tggctgcgtc aaaggcatca aggccctggg   9360
caagtatgtg gacctcaagc ggctgaacac gacaggcgtg agcgccggct gcaccgccga   9420
cctgctggtg gggcgcgcca tgactttcca tggccacggc ttccttcgcc tggcgctctc   9480
gaacgtggca ccgctcactg gcaacgtcta ctccggcttc ggcttccaca cgcccagga    9540 cagtgccctg ctctactacc gggcgtcccc ggatgggcta tgccaggtgt ccctgcagca   9600
gggccgtgtg agcctacagc tcctgaggac tgaagtgaaa actcaagcgg gcttcgccga   9660
```

```
tggtgccccc cattacgtcg ccttctacag caatgccacg ggagtctggc tgtatgtcga    9720
tgaccagctc cagcagatga agccccaccg gggaccaccc cccgagctcc agccgcagcc    9780
tgagggcccc ccgaggctcc tcctgggagg cctgcctgag tctggcacca tttacaactt    9840
cagtggctgc atcagcaacg tcttcgtgca gcggctcctg ggcccacagc gcgtatttga    9900
tctgcagcag aacctgggca gcgtcaatgt gagcacgggc tgtgcacccg ccctgcaagc    9960
ccagaccccg ggcctggggc ctagaggact gcaggccacc gcccggaagg cctcccgccg   10020
cagccgtcag cccgcccggc atcctgcctg catgctgccc ccacacctca ggaccacccg   10080
agactcctac cagtttgggg gttccctgtc cagtcacctg gagtttgtgg gcatcctggc   10140
ccgacatagg aactggccca gtctctccat gcacgtcctc ccgcgaagct cccgaggcct   10200
cctcctcttc actgcccgtc tgaggcccgg cagcccctcc ctggcgctct tcctgagcaa   10260
tggccacttc gttgcacaga tggaaggcct cgggactcgg ctccgcgccc agagccgcca   10320
gcgctcccgg cctggccgct ggcacaaggt ctccgtgcgc tgggagaaga accggatcct   10380
gctggtgacg gacggggccc gggcctggag ccaggagggg ccgcaccggc agcaccaggg   10440
ggcagagcac ccccagcccc acaccctctt tgtgggcggc ctcccggcca gcagccacag   10500
ctccaaactt ccggtgaccg tcgggttcag cggctgtgtg aagagactga ggctgcacgg   10560
gaggcccctg ggggcccccca cacggatggc aggggtcaca ccctgcatct tgggcccct   10620 ggaggcgggc ctgttcttcc caggcagcgg gggagttatc actttagacc tcccaggagc   10680
tacactgcct gatgtgggcc tggaactgga ggtgcggccc ctggcagtca ccggactgat   10740
cttccacttg ggccaggccc ggacgccccc ctacttgcag ttgcaggtga ccgagaagca   10800
agtcctgctg cgggcggatg acggagcagg ggagttctcc acgtcagtga cccgcccctc   10860
agtgctgtgt gatggccagt ggcaccggct agcggtgatg aaaagcggga atgtgctccg   10920
gctggaggtg gacgcgcaga gcaaccacac cgtgggcccc ttgctggcgg ctgcagctgg   10980
tgccccagcc cctctgtacc tcgggggcct gcctgagccc atggccgtgc agccctggcc   11040
ccccgcctac tgcggctgca tgaggaggct ggcggtgaac cggtccccg tcgccatgac   11100 tcgctctgtg gaggtccacg gggcagtggg gccagtggc tgcccagccg cctaggacac   11160
agccaacccc ggccctggt caggcccctg cagctgcctc acaccgcccc ttgtgctcgc   11220
ctcataggtg tctatttgga ctctaagctc tacgggtgac agatcttgtt tctgaagatg   11280
gtttaagtta tagcttctta aacgaaagaa taaaatactg caaaatgttt ttatatttgg   11340
cccttccacc catttttaat tgtgagagat ttgtcaccaa tcatcactgg ttcctcctta   11400
aaaattaaaa agtaacttct gtgtaaccga aaaaaaaaaa aaaaa                    11445
```

<210> SEQ ID NO 2
<211> LENGTH: 3695
<212> TYPE: PRT
<213> ORGANISM: Homo sapiens

<400> SEQUENCE: 2

```
Met Ala Lys Arg Leu Cys Ala Gly Ser Ala Leu Cys Val Arg Gly Pro
1               5                   10                  15

Arg Gly Pro Ala Pro Leu Leu Leu Val Gly Leu Ala Leu Leu Gly Ala
            20                  25                  30

Ala Arg Ala Arg Glu Glu Ala Gly Gly Gly Phe Ser Leu His Pro Pro
        35                  40                  45

Tyr Phe Asn Leu Ala Glu Gly Ala Arg Ile Ala Ala Ser Ala Thr Cys
    50                  55                  60
```

```
Gly Glu Glu Ala Pro Ala Arg Gly Ser Pro Arg Pro Thr Glu Asp Leu
 65                  70                  75                  80

Tyr Cys Lys Leu Val Gly Gly Pro Val Ala Gly Gly Asp Pro Asn Gln
                 85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
            115                 120                 125

Gln Ser Pro Pro Leu Ser Arg Gly Leu Glu Tyr Asn Glu Val Asn Val
            130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Phe Ala Ser Ser Lys
                180                 185                 190

Arg Asp Cys Leu Glu Arg Phe Gly Pro Gln Thr Leu Glu Arg Ile Thr
            195                 200                 205

Arg Asp Asp Ala Ala Ile Cys Thr Thr Glu Tyr Ser Arg Ile Val Pro
            210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
                260                 265                 270

Leu Met Gly Lys Ala Leu Arg Asp Pro Thr Val Thr Arg Arg Tyr Tyr
            275                 280                 285

Tyr Ser Ile Lys Asp Ile Ser Ile Gly Gly Arg Cys Val Cys His Gly
            290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
                340                 345                 350

Ala Asn Glu Cys Gln Ser Cys Asn Cys Tyr Gly His Ala Thr Asp Cys
            355                 360                 365

Tyr Tyr Asp Pro Glu Val Asp Arg Arg Arg Ala Ser Gln Ser Leu Asp
            370                 375                 380

Gly Thr Tyr Gln Gly Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
                420                 425                 430

Ser Asp Phe Thr Asp Gly Thr Cys Glu Asp Leu Thr Gly Arg Cys Tyr
            435                 440                 445

Cys Arg Pro Asn Phe Ser Gly Glu Arg Cys Asp Val Cys Ala Glu Gly
            450                 455                 460

Phe Thr Gly Phe Pro Ser Cys Tyr Pro Thr Pro Ser Ser Ser Asn Asp
465                 470                 475                 480
```

-continued

```
Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
        515                 520                 525

Cys Ala Pro Gly Phe Tyr Gly Pro Gly Cys Gln Pro Cys Gln Cys Ser
    530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575

Gly Tyr Phe His Phe Pro Leu Cys Gln Leu Cys Gly Cys Ser Pro Ala
            580                 585                 590

Gly Thr Leu Pro Glu Gly Cys Asp Glu Ala Gly Arg Cys Leu Cys Gln
        595                 600                 605

Pro Glu Phe Ala Gly Pro His Cys Asp Arg Cys Arg Pro Gly Tyr His
    610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
        675                 680                 685

Cys Asp Pro Arg Ser Gly Gln Cys Ser Cys Arg Pro Arg Val Thr Gly
    690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
        755                 760                 765

Asn Pro Glu Gly Cys Thr Arg Cys Ser Cys Asp Leu Arg Gly Thr Leu
    770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
            820                 825                 830

Ile Gly Gly Ala Leu Gly Gln Ser Cys Glu Pro Arg Thr Gly Val Cys
        835                 840                 845

Arg Cys Arg Pro Asn Thr Gln Gly Pro Thr Cys Ser Glu Pro Ala Arg
    850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895
```

```
Glu Phe Glu Asn Phe Ser Trp Arg Gly Tyr Ala Gln Met Ala Pro Val
        900                 905                 910

Gln Pro Arg Ile Val Ala Arg Leu Asn Leu Thr Ser Pro Asp Leu Phe
        915                 920                 925

Trp Leu Val Phe Arg Tyr Val Asn Arg Gly Ala Met Ser Val Ser Gly
        930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Ser Thr Glu Pro Ala
                965                 970                 975

Phe Ile Thr Val Pro Gln Arg Gly Phe Gly Pro Phe Val Leu Asn
                980                 985                 990

Pro Gly Thr Trp Ala Leu Arg Val Glu Ala Glu Gly Val Leu Leu Asp
        995                 1000                1005

Tyr Val Val Leu Leu Pro Ser Ala Tyr Tyr Glu Ala Ala Leu Leu
    1010                1015                1020

Gln Leu Arg Val Thr Glu Ala Cys Thr Tyr Arg Pro Ser Ala Gln
    1025                1030                1035

Gln Ser Gly Asp Asn Cys Leu Leu Tyr Thr His Leu Pro Leu Asp
    1040                1045                1050

Gly Phe Pro Ser Ala Ala Gly Leu Glu Ala Leu Cys Arg Gln Asp
    1055                1060                1065

Asn Ser Leu Pro Arg Pro Cys Pro Thr Glu Gln Leu Ser Pro Ser
    1070                1075                1080

His Pro Pro Leu Ile Thr Cys Thr Gly Ser Asp Val Asp Val Gln
    1085                1090                1095

Leu Gln Val Ala Val Pro Gln Pro Gly Arg Tyr Ala Leu Val Val
    1100                1105                1110

Glu Tyr Ala Asn Glu Asp Ala Arg Gln Glu Val Gly Val Ala Val
    1115                1120                1125

His Thr Pro Gln Arg Ala Pro Gln Gln Gly Leu Leu Ser Leu His
    1130                1135                1140

Pro Cys Leu Tyr Ser Thr Leu Cys Arg Gly Thr Ala Arg Asp Thr
    1145                1150                1155

Gln Asp His Leu Ala Val Phe His Leu Asp Ser Glu Ala Ser Val
    1160                1165                1170

Arg Leu Thr Ala Glu Gln Ala Arg Phe Phe Leu His Gly Val Thr
    1175                1180                1185

Leu Val Pro Ile Glu Glu Phe Ser Pro Glu Phe Val Glu Pro Arg
    1190                1195                1200

Val Ser Cys Ile Ser Ser His Gly Ala Phe Gly Pro Asn Ser Ala
    1205                1210                1215

Ala Cys Leu Pro Ser Arg Phe Pro Lys Pro Pro Gln Pro Ile Ile
    1220                1225                1230

Leu Arg Asp Cys Gln Val Ile Pro Leu Pro Pro Gly Leu Pro Leu
    1235                1240                1245

Thr His Ala Gln Asp Leu Thr Pro Ala Met Ser Pro Ala Gly Pro
    1250                1255                1260

Arg Pro Arg Pro Pro Thr Ala Val Asp Pro Asp Ala Glu Pro Thr
    1265                1270                1275

Leu Leu Arg Glu Pro Gln Ala Thr Val Val Phe Thr Thr His Val
    1280                1285                1290
```

```
Pro Thr Leu Gly Arg Tyr Ala Phe Leu Leu His Gly Tyr Gln Pro
    1295                1300                1305

Ala His Pro Thr Phe Pro Val Glu Val Leu Ile Asn Ala Gly Arg
    1310                1315                1320

Val Trp Gln Gly His Ala Asn Ala Ser Phe Cys Pro His Gly Tyr
    1325                1330                1335

Gly Cys Arg Thr Leu Val Val Cys Glu Gly Gln Ala Leu Leu Asp
    1340                1345                1350

Val Thr His Ser Glu Leu Thr Val Thr Val Arg Val Pro Lys Gly
    1355                1360                1365

Arg Trp Leu Trp Leu Asp Tyr Val Leu Val Val Pro Glu Asn Val
    1370                1375                1380

Tyr Ser Phe Gly Tyr Leu Arg Glu Glu Pro Leu Asp Lys Ser Tyr
    1385                1390                1395

Asp Phe Ile Ser His Cys Ala Ala Gln Gly Tyr His Ile Ser Pro
    1400                1405                1410

Ser Ser Ser Ser Leu Phe Cys Arg Asn Ala Ala Ala Ser Leu Ser
    1415                1420                1425

Leu Phe Tyr Asn Asn Gly Ala Arg Pro Cys Gly Cys His Glu Val
    1430                1435                1440

Gly Ala Thr Gly Pro Thr Cys Glu Pro Phe Gly Gly Gln Cys Pro
    1445                1450                1455

Cys His Ala His Val Ile Gly Arg Asp Cys Ser Arg Cys Ala Thr
    1460                1465                1470

Gly Tyr Trp Gly Phe Pro Asn Cys Arg Pro Cys Asp Cys Gly Ala
    1475                1480                1485

Arg Leu Cys Asp Glu Leu Thr Gly Gln Cys Ile Cys Pro Pro Arg
    1490                1495                1500

Thr Ile Pro Pro Asp Cys Leu Leu Cys Gln Pro Gln Thr Phe Gly
    1505                1510                1515

Cys His Pro Leu Val Gly Cys Glu Glu Cys Asn Cys Ser Gly Pro
    1520                1525                1530

Gly Ile Gln Glu Leu Thr Asp Pro Thr Cys Asp Thr Asp Ser Gly
    1535                1540                1545

Gln Cys Lys Cys Arg Pro Asn Val Thr Gly Arg Arg Cys Asp Thr
    1550                1555                1560

Cys Ser Pro Gly Phe His Gly Tyr Pro Arg Cys Arg Pro Cys Asp
    1565                1570                1575

Cys His Glu Ala Gly Thr Ala Pro Gly Val Cys Asp Pro Leu Thr
    1580                1585                1590

Gly Gln Cys Tyr Cys Lys Glu Asn Val Gln Gly Pro Lys Cys Asp
    1595                1600                1605

Gln Cys Ser Leu Gly Thr Phe Ser Leu Asp Ala Ala Asn Pro Lys
    1610                1615                1620

Gly Cys Thr Arg Cys Phe Cys Phe Gly Ala Thr Glu Arg Cys Arg
    1625                1630                1635

Ser Ser Ser Tyr Thr Arg Gln Glu Phe Val Asp Met Glu Gly Trp
    1640                1645                1650

Val Leu Leu Ser Thr Asp Arg Gln Val Val Pro His Glu Arg Gln
    1655                1660                1665

Pro Gly Thr Glu Met Leu Arg Ala Asp Leu Arg His Val Pro Glu
    1670                1675                1680
```

```
Ala Val Pro Glu Ala Phe Pro Glu Leu Tyr Trp Gln Ala Pro Pro
1685                1690                1695

Ser Tyr Leu Gly Asp Arg Val Ser Ser Tyr Gly Gly Thr Leu Arg
1700                1705                1710

Tyr Glu Leu His Ser Glu Thr Gln Arg Gly Asp Val Phe Val Pro
1715                1720                1725

Met Glu Ser Arg Pro Asp Val Val Leu Gln Gly Asn Gln Met Ser
1730                1735                1740

Ile Thr Phe Leu Glu Pro Ala Tyr Pro Thr Pro Gly His Val His
1745                1750                1755

Arg Gly Gln Leu Gln Leu Val Glu Gly Asn Phe Arg His Thr Glu
1760                1765                1770

Thr Arg Asn Thr Val Ser Arg Glu Glu Leu Met Met Val Leu Ala
1775                1780                1785

Ser Leu Glu Gln Leu Gln Ile Arg Ala Leu Phe Ser Gln Ile Ser
1790                1795                1800

Ser Ala Val Phe Leu Arg Arg Val Ala Leu Glu Val Ala Ser Pro
1805                1810                1815

Ala Gly Gln Gly Ala Leu Ala Ser Asn Val Glu Leu Cys Leu Cys
1820                1825                1830

Pro Ala Ser Tyr Arg Gly Asp Ser Cys Gln Glu Cys Ala Pro Gly
1835                1840                1845

Phe Tyr Arg Asp Val Lys Gly Leu Phe Leu Gly Arg Cys Val Pro
1850                1855                1860

Cys Gln Cys His Gly His Ser Asp Arg Cys Leu Pro Gly Ser Gly
1865                1870                1875

Val Cys Val Asp Cys Gln His Asn Thr Glu Gly Ala His Cys Glu
1880                1885                1890

Arg Cys Gln Ala Gly Phe Val Ser Ser Arg Asp Pro Ser Ala
1895                1900                1905

Pro Cys Val Ser Cys Pro Cys Pro Leu Ser Val Pro Ser Asn Asn
1910                1915                1920

Phe Ala Glu Gly Cys Val Leu Arg Gly Gly Arg Thr Gln Cys Leu
1925                1930                1935

Cys Lys Pro Gly Tyr Ala Gly Ala Ser Cys Glu Arg Cys Ala Pro
1940                1945                1950

Gly Phe Phe Gly Asn Pro Leu Val Leu Gly Ser Ser Cys Gln Pro
1955                1960                1965

Cys Asp Cys Ser Gly Asn Gly Asp Pro Asn Leu Leu Phe Ser Asp
1970                1975                1980

Cys Asp Pro Leu Thr Gly Ala Cys Arg Gly Cys Leu Arg His Thr
1985                1990                1995

Thr Gly Pro Arg Cys Glu Ile Cys Ala Pro Gly Phe Tyr Gly Asn
2000                2005                2010

Ala Leu Leu Pro Gly Asn Cys Thr Arg Cys Asp Cys Thr Pro Cys
2015                2020                2025

Gly Thr Glu Ala Cys Asp Pro His Ser Gly His Cys Leu Cys Lys
2030                2035                2040

Ala Gly Val Thr Gly Arg Arg Cys Asp Arg Cys Gln Glu Gly His
2045                2050                2055

Phe Gly Phe Asp Gly Cys Gly Gly Cys Arg Pro Cys Ala Cys Gly
2060                2065                2070
```

-continued

Pro Ala Ala Glu Gly Ser Glu Cys His Pro Gln Ser Gly Gln Cys
2075                2080                2085

His Cys Arg Pro Gly Thr Met Gly Pro Gln Cys Arg Glu Cys Ala
2090                2095                2100

Pro Gly Tyr Trp Gly Leu Pro Glu Gln Gly Cys Arg Arg Cys Gln
2105                2110                2115

Cys Pro Gly Gly Arg Cys Asp Pro His Thr Gly Arg Cys Asn Cys
2120                2125                2130

Pro Pro Gly Leu Ser Gly Glu Arg Cys Asp Thr Cys Ser Gln Gln
2135                2140                2145

His Gln Val Pro Val Pro Gly Gly Pro Val Gly His Ser Ile His
2150                2155                2160

Cys Glu Val Cys Asp His Cys Val Val Leu Leu Leu Asp Asp Leu
2165                2170                2175

Glu Arg Ala Gly Ala Leu Leu Pro Ala Ile His Glu Gln Leu Arg
2180                2185                2190

Gly Ile Asn Ala Ser Ser Met Ala Trp Ala Arg Leu His Arg Leu
2195                2200                2205

Asn Ala Ser Ile Ala Asp Leu Gln Ser Gln Leu Arg Ser Pro Leu
2210                2215                2220

Gly Pro Arg His Glu Thr Ala Gln Gln Leu Glu Val Leu Glu Gln
2225                2230                2235

Gln Ser Thr Ser Leu Gly Gln Asp Ala Arg Arg Leu Gly Gly Gln
2240                2245                2250

Ala Val Gly Thr Arg Asp Gln Ala Ser Gln Leu Leu Ala Gly Thr
2255                2260                2265

Glu Ala Thr Leu Gly His Ala Lys Thr Leu Leu Ala Ala Ile Arg
2270                2275                2280

Ala Val Asp Arg Thr Leu Ser Glu Leu Met Ser Gln Thr Gly His
2285                2290                2295

Leu Gly Leu Ala Asn Ala Ser Ala Pro Ser Gly Glu Gln Leu Leu
2300                2305                2310

Arg Thr Leu Ala Glu Val Glu Arg Leu Leu Trp Glu Met Arg Ala
2315                2320                2325

Arg Asp Leu Gly Ala Pro Gln Ala Ala Glu Ala Glu Leu Ala
2330                2335                2340

Ala Ala Gln Arg Leu Leu Ala Arg Val Gln Glu Gln Leu Ser Ser
2345                2350                2355

Leu Trp Glu Glu Asn Gln Ala Leu Ala Thr Gln Thr Arg Asp Arg
2360                2365                2370

Leu Ala Gln His Glu Ala Gly Leu Met Asp Leu Arg Glu Ala Leu
2375                2380                2385

Asn Arg Ala Val Asp Ala Thr Arg Glu Ala Gln Glu Leu Asn Ser
2390                2395                2400

Arg Asn Gln Glu Arg Leu Glu Glu Ala Leu Gln Arg Lys Gln Glu
2405                2410                2415

Leu Ser Arg Asp Asn Ala Thr Leu Gln Ala Thr Leu His Ala Ala
2420                2425                2430

Arg Asp Thr Leu Ala Ser Val Phe Arg Leu Leu His Ser Leu Asp
2435                2440                2445

Gln Ala Lys Glu Glu Leu Glu Arg Leu Ala Ala Ser Leu Asp Gly
2450                2455                2460

```
Ala Arg Thr Pro Leu Leu Gln Arg Met Gln Thr Phe Ser Pro Ala
    2465            2470                2475

Gly Ser Lys Leu Arg Leu Val Glu Ala Ala Glu Ala His Ala Gln
    2480            2485                2490

Gln Leu Gly Gln Leu Ala Leu Asn Leu Ser Ser Ile Ile Leu Asp
    2495            2500                2505

Val Asn Gln Asp Arg Leu Thr Gln Arg Ala Ile Glu Ala Ser Asn
    2510            2515                2520

Ala Tyr Ser Arg Ile Leu Gln Ala Val Gln Ala Ala Glu Asp Ala
    2525            2530                2535

Ala Gly Gln Ala Leu Gln Gln Ala Asp His Thr Trp Ala Thr Val
    2540            2545                2550

Val Arg Gln Gly Leu Val Asp Arg Ala Gln Gln Leu Leu Ala Asn
    2555            2560                2565

Ser Thr Ala Leu Glu Glu Ala Met Leu Gln Glu Gln Gln Arg Leu
    2570            2575                2580

Gly Leu Val Trp Ala Ala Leu Gln Gly Ala Arg Thr Gln Leu Arg
    2585            2590                2595

Asp Val Arg Ala Lys Lys Asp Gln Leu Glu Ala His Ile Gln Ala
    2600            2605                2610

Ala Gln Ala Met Leu Ala Met Asp Thr Asp Glu Thr Ser Lys Lys
    2615            2620                2625

Ile Ala His Ala Lys Ala Val Ala Ala Glu Ala Gln Asp Thr Ala
    2630            2635                2640

Thr Arg Val Gln Ser Gln Leu Gln Ala Met Gln Glu Asn Val Glu
    2645            2650                2655

Arg Trp Gln Gly Gln Tyr Glu Gly Leu Arg Gly Gln Asp Leu Gly
    2660            2665                2670

Gln Ala Val Leu Asp Ala Gly His Ser Val Ser Thr Leu Glu Lys
    2675            2680                2685

Thr Leu Pro Gln Leu Leu Ala Lys Leu Ser Ile Leu Glu Asn Arg
    2690            2695                2700

Gly Val His Asn Ala Ser Leu Ala Leu Ser Ala Ser Ile Gly Arg
    2705            2710                2715

Val Arg Glu Leu Ile Ala Gln Ala Arg Gly Ala Ala Ser Lys Val
    2720            2725                2730

Lys Val Pro Met Lys Phe Asn Gly Arg Ser Gly Val Gln Leu Arg
    2735            2740                2745

Thr Pro Arg Asp Leu Ala Asp Leu Ala Ala Tyr Thr Ala Leu Lys
    2750            2755                2760

Phe Tyr Leu Gln Gly Pro Glu Pro Glu Pro Gly Gln Gly Thr Glu
    2765            2770                2775

Asp Arg Phe Val Met Tyr Met Gly Ser Arg Gln Ala Thr Gly Asp
    2780            2785                2790

Tyr Met Gly Val Ser Leu Arg Asp Lys Lys Val His Trp Val Tyr
    2795            2800                2805

Gln Leu Gly Glu Ala Gly Pro Ala Val Leu Ser Ile Asp Glu Asp
    2810            2815                2820

Ile Gly Glu Gln Phe Ala Ala Val Ser Leu Asp Arg Thr Leu Gln
    2825            2830                2835

Phe Gly His Met Ser Val Thr Val Glu Arg Gln Met Ile Gln Glu
    2840            2845                2850
```

```
Thr Lys Gly Asp Thr Val Ala Pro Gly Ala Glu Gly Leu Leu Asn
2855                2860                2865

Leu Arg Pro Asp Asp Phe Val Phe Tyr Val Gly Gly Tyr Pro Ser
2870                2875                2880

Thr Phe Thr Pro Pro Pro Leu Leu Arg Phe Pro Gly Tyr Arg Gly
2885                2890                2895

Cys Ile Glu Met Asp Thr Leu Asn Glu Glu Val Val Ser Leu Tyr
2900                2905                2910

Asn Phe Glu Arg Thr Phe Gln Leu Asp Thr Ala Val Asp Arg Pro
2915                2920                2925

Cys Ala Arg Ser Lys Ser Thr Gly Asp Pro Trp Leu Thr Asp Gly
2930                2935                2940

Ser Tyr Leu Asp Gly Thr Gly Phe Ala Arg Ile Ser Phe Asp Ser
2945                2950                2955

Gln Ile Ser Thr Thr Lys Arg Phe Glu Gln Glu Leu Arg Leu Val
2960                2965                2970

Ser Tyr Ser Gly Val Leu Phe Phe Leu Lys Gln Gln Ser Gln Phe
2975                2980                2985

Leu Cys Leu Ala Val Gln Glu Gly Ser Leu Val Leu Leu Tyr Asp
2990                2995                3000

Phe Gly Ala Gly Leu Lys Lys Ala Val Pro Leu Gln Pro Pro Pro
3005                3010                3015

Pro Leu Thr Ser Ala Ser Lys Ala Ile Gln Val Phe Leu Leu Gly
3020                3025                3030

Gly Ser Arg Lys Arg Val Leu Val Arg Val Glu Arg Ala Thr Val
3035                3040                3045

Tyr Ser Val Glu Gln Asp Asn Asp Leu Glu Leu Ala Asp Ala Tyr
3050                3055                3060

Tyr Leu Gly Gly Val Pro Pro Asp Gln Leu Pro Pro Ser Leu Arg
3065                3070                3075

Arg Leu Phe Pro Thr Gly Gly Ser Val Arg Gly Cys Val Lys Gly
3080                3085                3090

Ile Lys Ala Leu Gly Lys Tyr Val Asp Leu Lys Arg Leu Asn Thr
3095                3100                3105

Thr Gly Val Ser Ala Gly Cys Thr Ala Asp Leu Leu Val Gly Arg
3110                3115                3120

Ala Met Thr Phe His Gly His Gly Phe Leu Arg Leu Ala Leu Ser
3125                3130                3135

Asn Val Ala Pro Leu Thr Gly Asn Val Tyr Ser Gly Phe Gly Phe
3140                3145                3150

His Ser Ala Gln Asp Ser Ala Leu Leu Tyr Tyr Arg Ala Ser Pro
3155                3160                3165

Asp Gly Leu Cys Gln Val Ser Leu Gln Gln Gly Arg Val Ser Leu
3170                3175                3180

Gln Leu Leu Arg Thr Glu Val Lys Thr Gln Ala Gly Phe Ala Asp
3185                3190                3195

Gly Ala Pro His Tyr Val Ala Phe Tyr Ser Asn Ala Thr Gly Val
3200                3205                3210

Trp Leu Tyr Val Asp Asp Gln Leu Gln Gln Met Lys Pro His Arg
3215                3220                3225

Gly Pro Pro Pro Glu Leu Gln Pro Gln Pro Glu Gly Pro Pro Arg
3230                3235                3240
```

-continued

Leu Leu Leu Gly Gly Leu Pro Glu Ser Gly Thr Ile Tyr Asn Phe
3245                3250                3255

Ser Gly Cys Ile Ser Asn Val Phe Val Gln Arg Leu Leu Gly Pro
3260                3265                3270

Gln Arg Val Phe Asp Leu Gln Gln Asn Leu Gly Ser Val Asn Val
3275                3280                3285

Ser Thr Gly Cys Ala Pro Ala Leu Gln Ala Gln Thr Pro Gly Leu
3290                3295                3300

Gly Pro Arg Gly Leu Gln Ala Thr Ala Arg Lys Ala Ser Arg Arg
3305                3310                3315

Ser Arg Gln Pro Ala Arg His Pro Ala Cys Met Leu Pro Pro His
3320                3325                3330

Leu Arg Thr Thr Arg Asp Ser Tyr Gln Phe Gly Gly Ser Leu Ser
3335                3340                3345

Ser His Leu Glu Phe Val Gly Ile Leu Ala Arg His Arg Asn Trp
3350                3355                3360

Pro Ser Leu Ser Met His Val Leu Pro Arg Ser Ser Arg Gly Leu
3365                3370                3375

Leu Leu Phe Thr Ala Arg Leu Arg Pro Gly Ser Pro Ser Leu Ala
3380                3385                3390

Leu Phe Leu Ser Asn Gly His Phe Val Ala Gln Met Glu Gly Leu
3395                3400                3405

Gly Thr Arg Leu Arg Ala Gln Ser Arg Gln Arg Ser Arg Pro Gly
3410                3415                3420

Arg Trp His Lys Val Ser Val Arg Trp Glu Lys Asn Arg Ile Leu
3425                3430                3435

Leu Val Thr Asp Gly Ala Arg Ala Trp Ser Gln Glu Gly Pro His
3440                3445                3450

Arg Gln His Gln Gly Ala Glu His Pro Gln Pro His Thr Leu Phe
3455                3460                3465

Val Gly Gly Leu Pro Ala Ser Ser His Ser Ser Lys Leu Pro Val
3470                3475                3480

Thr Val Gly Phe Ser Gly Cys Val Lys Arg Leu Arg Leu His Gly
3485                3490                3495

Arg Pro Leu Gly Ala Pro Thr Arg Met Ala Gly Val Thr Pro Cys
3500                3505                3510

Ile Leu Gly Pro Leu Glu Ala Gly Leu Phe Phe Pro Gly Ser Gly
3515                3520                3525

Gly Val Ile Thr Leu Asp Leu Pro Gly Ala Thr Leu Pro Asp Val
3530                3535                3540

Gly Leu Glu Leu Glu Val Arg Pro Leu Ala Val Thr Gly Leu Ile
3545                3550                3555

Phe His Leu Gly Gln Ala Arg Thr Pro Pro Tyr Leu Gln Leu Gln
3560                3565                3570

Val Thr Glu Lys Gln Val Leu Leu Arg Ala Asp Asp Gly Ala Gly
3575                3580                3585

Glu Phe Ser Thr Ser Val Thr Arg Pro Ser Val Leu Cys Asp Gly
3590                3595                3600

Gln Trp His Arg Leu Ala Val Met Lys Ser Gly Asn Val Leu Arg
3605                3610                3615

Leu Glu Val Asp Ala Gln Ser Asn His Thr Val Gly Pro Leu Leu
3620                3625                3630

| Ala | Ala | Ala | Ala | Gly | Ala | Pro | Ala | Pro | Leu | Tyr | Leu | Gly | Gly | Leu |
|---|---|---|---|---|---|---|---|---|---|---|---|---|---|---|
| 3635 | | | | 3640 | | | | 3645 | | | | | | |

| Pro | Glu | Pro | Met | Ala | Val | Gln | Pro | Trp | Pro | Pro | Ala | Tyr | Cys | Gly |
|---|---|---|---|---|---|---|---|---|---|---|---|---|---|---|
| 3650 | | | | 3655 | | | | 3660 | | | | | | |

| Cys | Met | Arg | Arg | Leu | Ala | Val | Asn | Arg | Ser | Pro | Val | Ala | Met | Thr |
|---|---|---|---|---|---|---|---|---|---|---|---|---|---|---|
| 3665 | | | | 3670 | | | | 3675 | | | | | | |

| Arg | Ser | Val | Glu | Val | His | Gly | Ala | Val | Gly | Ala | Ser | Gly | Cys | Pro |
|---|---|---|---|---|---|---|---|---|---|---|---|---|---|---|
| 3680 | | | | 3685 | | | | 3690 | | | | | | |

| Ala | Ala |
|---|---|
| 3695 | |

<210> SEQ ID NO 3
<211> LENGTH: 5866
<212> TYPE: DNA
<213> ORGANISM: Homo sapiens

<400> SEQUENCE: 3

```
gggacctgga agcgccccag ccccgcagcg atcgcagatt cggctttcaa acaaaagagg      60
cgccccgggg ggtgggaccg ggacctcacc cggtcctcgc agagttgcgg ccgcccgccc     120
cttcagcccc ggctctccgt atgcgcatga gcagaggcgc ctccctctgt tcctcccaag     180
gctaaacttt ctaattccct tctttgggct cgggggctcc cggagcaggg cgagagctcg     240
cgtcgccgga aggaagacg ggaagaaagg gcaggcggct cggcgggcgt cttctccact     300
cctctgccgc gtccccgtgg ctgcagggag ccggcatggg gcttctccag ttgctagctt     360
tcagtttctt agccctgtgc agagcccgag tgcgcgctca ggaacccgag ttcagctacg     420
gctgcgcaga aggcagctgc tatcccgcca cgggcgacct tctcatcggc cgagcacaga     480
agctttcggt gacctcgacg tgcgggctgc acaagcccga accctactgt atcgtcagcc     540
acttgcagga ggacaaaaaa tgcttcatat gcaattccca agatccttat catgagaccc     600
tgaatcctga cagccatctc attgaaaatg tggtcactac atttgctcca aaccgcctta     660
agatttggtg gcaatctgaa atggtgtgg aaaatgtaac tatccaactg gatttggaag     720
cagaattcca ttttactcat ctcataatga cttttcaagac attccgtcca gctgctatgc     780
tgatagaacg atcgtccgac tttgggaaaa cctggggtgt gtatagatac ttcgcctatg     840
actgtgaggc ctcgtttcca ggcatttcaa ctggccccat gaaaaaagtc gatgacataa     900
tttgtgattc tcgatattct gacattgaac cctcaactga aggagaggtg atatttcgtg     960
ctttagatcc tgctttcaaa atagaagatc cttatagccc aaggatacag aatttattaa    1020
aaattaccaa cttgagaatc aagtttgtga aactgcatac tttgggagat aaccttctgg    1080
attccaggat ggaaatcaga gaaaagtatt attatgcagt ttatgatatg gtggttcgag    1140
gaaattgctt ctgctatggt catgccagcg aatgtgcccc tgtggatgga ttcaatgaag    1200
aagtggaagg aatggttcac ggacactgca tgtgcaggca taacaccaag ggcttaaact    1260
gtgaactctg catggatttc taccatgatt taccttggag acctgctgaa ggccgaaaca    1320
gcaacgcctg taaaaaatgt aactgcaatg aacattccat ctcttgtcac tttgacatgg    1380
ctgtttacct ggccacgggg aacgtcagcg gaggcgtgtg tgatgactgt cagcacaaca    1440
ccatggggcg caactgtgag cagtgcaagc cgttttacta ccagcaccca gagagggaca    1500
tccgagatcc taatttctgt gaacgatgta cgtgtgaccc agctggctct caaaatgagg    1560
gaatttgtga cagctatact gattttttcta ctggtctcat tgctggccag tgtcggtgta    1620
aattaaatgt ggaaggagaa cattgtgatg tttgcaaaga aggcttctat gatttaagca    1680
```

```
gtgaagatcc atttggttgt aaatcttgtg cttgcaatcc tctgggaaca attcctggag    1740
ggaatccttg tgattccgag acaggtcact gctactgcaa gcgtctggtg acaggacagc    1800
attgtgacca gtgcctgcca gagcactggg gcttaagcaa tgatttggat ggatgtcgac    1860
catgtgactg tgaccttggg ggagccttaa acaacagttg ctttgcggag tcaggccagt    1920
gctcatgccg gcctcacatg attggacgtc agtgcaacga agtggaacct ggttactact    1980
ttgccaccct ggatcactac ctctatgaag cggaggaagc caacttgggg cctggggtta    2040
gcatagtgga gcggcaatat atccaggacc ggattccctc ctggactgga gccggcttcg    2100
tccgagtgcc tgaaggggct tatttggagt ttttcattga caacatacca tattccatgg    2160
agtacgacat cctaattcgc tacgagccac agctacccga ccactgggaa aaagctgtca    2220
tcacagtgca gcgacctgga aggattccaa ccagcagccg atgtggtaat accatccccg    2280
atgatgacaa ccaggtggtg tcattatcac caggctcaag atatgtcgtc cttcctcggc    2340
cggtgtgctt tgagaaggga acaaactaca cggtgaggtt ggagctgcct cagtacacct    2400
cctctgatag cgacgtggag agccctaca cgctgatcga ttctcttgtt ctcatgccat    2460
actgtaaatc actggacatc ttcaccgtgg gaggttcagg agatggggtg gtcaccaaca    2520
gtgcctggga aaccttttcag agataccgat gtctagagaa cagcagaagc gttgtgaaaa    2580
caccgatgac agatgtttgc agaaacatca tctttagcat ttctgccctg ttacaccaga    2640
caggcctggc ttgtgaatgc gaccctcagg gttcgttaag ttccgtgtgt gatcccaacg    2700
gaggccagtg ccagtgccgg cccaacgtgg ttggaagaac ctgcaacaga tgtgcacctg    2760
gaacttttgg ctttggcccc agtggatgca aaccttgtga gtgccatctg caaggatctg    2820
tcaatgcctt ctgcaatccc gtcactggcc agtgccactg tttccaggga gtgtatgctc    2880
ggcagtgtga tcggtgctta cctgggcact ggggctttcc aagttgccag ccctgccagt    2940
gcaatggcca cgccgatgac tgcgacccag tgactgggga gtgcttgaac tgccaggact    3000
acaccatggg tcataactgt gaaaggtgct tggctggtta ctatgcgac cccatcattg    3060 ggtcaggaga tcactgccgc ccttgccctt gcccagatgg tcccgacagt ggacgccagt    3120
ttgccaggag ctgctaccaa gatcctgtta ctttacagct tgcctgtgtt tgtgatcctg    3180
gatacattgg ttccagatgt gacgactgtg cctcaggata ctttggcaat ccatcagaag    3240 ttgggggggtc gtgtcagcct tgccagtgtc acaacaacat tgacacgaca gacccagaag    3300
cctgtgacaa ggagactggg aggtgtctca gtgcctgta ccacacggaa ggggaacact    3360
gtcagttctg ccggtttgga tactatggtg atgccctcca gcaggactgt cgaaagtgtg    3420
tctgtaatta cctgggcacc gtgcaagagc actgtaacgg ctctgactgc cagtgcgaca    3480
aagccactgg tcagtgcttg tgtcttccta atgtgatcgg gcagaactgt gaccgctgtg    3540
cgcccaatac ctggcagctg gccagtggca ctggctgtga cccatgcaac tgcaatgctg    3600
ctcattcctt cgggccatct tgcaatgagt tcacggggca gtgccagtgc atgcctgggt    3660
ttggaggccg cacctgcagc gagtgccagg aactcttctg gggagacccc gacgtggagt    3720
gccgagcctg tgactgtgac cccaggggca ttgagacgcc acagtgtgac cagtccacgg    3780
gccagtgtgt ctgcgttgag ggtgttgagg gtccacgctg tgacaagtgc acgcgagggt    3840
actcgggggt cttccctgac tgcacaccct gccaccagtg ctttgctctc tgggatgtga    3900
tcattgccga gctgaccaac aggacacaca gattcctgga aaagccaag gccttgaaga    3960 tcagtggtgt gatcggcct taccgtgaga ctgtggactc ggtggagagg aaagtcagcg    4020
agataaaaga catcctggcg cagagccccg cagcagagcc actgaaaaac attgggaatc    4080
```

-continued

```
tctttgagga agcagagaaa ctgattaaag atgttacaga aatgatggct caagtagaag    4140
tgaaattatc tgacacaact tcccaaagca acagcacagc caaagaactg gattctctac    4200
agacagaagc cgaaagccta gacaacactg tgaagaact tgctgaacaa ctggaattta    4260
tcaaaaactc agatattcgg ggtgccttgg atagcattac caagtatttc cagatgtctc    4320
ttgaggcaga ggagagggtg aatgcctcca ccacagaacc caacagcact gtggagcagt    4380
cagccctcat gagagacaga gtagaagacg tgatgatgga gcgagaatcc cagttcaagg    4440
aaaaacaaga ggagcaggct cgcctccttg atgaactggc aggcaagcta caaagcctag    4500
acctttcagc cgctgccgaa atgacctgtg aacacccc aggggcctcc tgttccgaga    4560
ctgaatgtgg cgggccaaac tgcagaactg acgaaggaga gaggaagtgt gggggcctg    4620 gctgtggtgg tctggttact gttgcacaca acgcctggca gaaagccatg gacttggacc    4680
aagatgtcct gagtgccctg gctgaagtgg aacagctctc caagatggtc tctgaagcaa    4740
aactgagggc agatgaggca aaacaaagtg ctgaagacat tctgttgaag acaaatgcta    4800
ccaaagaaaa aatggacaag agcaatgagg agctgagaaa tctaatcaag caaatcagaa    4860 acttttttgac ccaggatagt gctgattgg acagcattga agcagttgct aatgaagtat    4920
tgaaaatgga gatgcctagc accccacagc agttacagaa cttgacagaa gatatacgtg    4980
aacgagttga aagccttct caagtagagg ttattcttca gcatagtgct gctgacattg    5040
ccagagctga gatgttgtta gaagaagcta aaagagcaa caaaagtgca acagatgtta    5100
aagtcactgc agatatggta aaggaagctc tggaagaagc agaaaaggcc caggtcgcag    5160
cagagaaggc aattaaacaa gcagatgaag acattcaagg aacccagaac tgttaacct    5220 cgattgagtc tgaaacagca gcttctgagg aaaccttgtt caacgcgtcc cagcgcatca    5280
gcgagttaga gaggaatgtg gaagaactta agcggaaagc tgcccaaaac tccggggagg    5340
cagaatatat tgaaaaagta gtatatactg tgaagcaaag tgcagaagat gttaagaaga    5400
ctttagatgg tgaacttgat gaaaagtata aaaagtaga aatttaatt gccaaaaaaa    5460 ctgaagagtc agctgatgcc agaaggaaag ccgaaatgct acaaaatgaa gcaaaaactc    5520
ttttagctca agcaaatagc aagctgcaac tgctcaaaga tttagaaaga aaatatgaag    5580
acaatcaaag atacttagaa gataaagctc aagaattagc aagactggaa ggagaagtcc    5640
gttcactcct aaaggatata agccagaaag ttgctgtgta tagcacatgc ttgtaacaga    5700
ggagaataaa aaatggctga ggtgaacaag gtaaaacaac tacattttaa aaactgactt    5760
aatgctcttc aaaataaaac atcacctatt taatgttttt aatcacattt tgtatggagt    5820
taaataaagt acagtgcttt tgtataaaaa aaaaaaaaa aaaaaa               5866
```

<210> SEQ ID NO 4
<211> LENGTH: 1786
<212> TYPE: PRT
<213> ORGANISM: Homo sapiens

<400> SEQUENCE: 4

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
                20                  25                  30

Gly Ser Cys Tyr Pro Ala Thr Gly Asp Leu Leu Ile Gly Arg Ala Gln
            35                  40                  45

-continued

```
Lys Leu Ser Val Thr Ser Thr Cys Gly Leu His Lys Pro Glu Pro Tyr
 50                  55                  60
Cys Ile Val Ser His Leu Gln Glu Asp Lys Lys Cys Phe Ile Cys Asn
 65                  70                  75                  80
Ser Gln Asp Pro Tyr His Glu Thr Leu Asn Pro Asp Ser His Leu Ile
                 85                  90                  95
Glu Asn Val Val Thr Thr Phe Ala Pro Asn Arg Leu Lys Ile Trp Trp
                100                 105                 110
Gln Ser Glu Asn Gly Val Glu Asn Val Thr Ile Gln Leu Asp Leu Glu
            115                 120                 125
Ala Glu Phe His Phe Thr His Leu Ile Met Thr Phe Lys Thr Phe Arg
130                 135                 140
Pro Ala Ala Met Leu Ile Glu Arg Ser Ser Asp Phe Gly Lys Thr Trp
145                 150                 155                 160
Gly Val Tyr Arg Tyr Phe Ala Tyr Asp Cys Glu Ala Ser Phe Pro Gly
                165                 170                 175
Ile Ser Thr Gly Pro Met Lys Lys Val Asp Asp Ile Ile Cys Asp Ser
            180                 185                 190
Arg Tyr Ser Asp Ile Glu Pro Ser Thr Glu Gly Glu Val Ile Phe Arg
        195                 200                 205
Ala Leu Asp Pro Ala Phe Lys Ile Glu Asp Pro Tyr Ser Pro Arg Ile
210                 215                 220
Gln Asn Leu Leu Lys Ile Thr Asn Leu Arg Ile Lys Phe Val Lys Leu
225                 230                 235                 240
His Thr Leu Gly Asp Asn Leu Leu Asp Ser Arg Met Glu Ile Arg Glu
                245                 250                 255
Lys Tyr Tyr Tyr Ala Val Tyr Asp Met Val Val Arg Gly Asn Cys Phe
            260                 265                 270
Cys Tyr Gly His Ala Ser Glu Cys Ala Pro Val Asp Gly Phe Asn Glu
        275                 280                 285
Glu Val Glu Gly Met Val His Gly His Cys Met Cys Arg His Asn Thr
290                 295                 300
Lys Gly Leu Asn Cys Glu Leu Cys Met Asp Phe Tyr His Asp Leu Pro
305                 310                 315                 320
Trp Arg Pro Ala Glu Gly Arg Asn Ser Asn Ala Cys Lys Lys Cys Asn
                325                 330                 335
Cys Asn Glu His Ser Ile Ser Cys His Phe Asp Met Ala Val Tyr Leu
            340                 345                 350
Ala Thr Gly Asn Val Ser Gly Val Cys Asp Asp Cys Gln His Asn
        355                 360                 365
Thr Met Gly Arg Asn Cys Glu Gln Cys Lys Pro Phe Tyr Tyr Gln His
370                 375                 380
Pro Glu Arg Asp Ile Arg Asp Pro Asn Phe Cys Glu Arg Cys Thr Cys
385                 390                 395                 400
Asp Pro Ala Gly Ser Gln Asn Glu Gly Ile Cys Asp Ser Tyr Thr Asp
                405                 410                 415
Phe Ser Thr Gly Leu Ile Ala Gly Gln Cys Arg Cys Lys Leu Asn Val
            420                 425                 430
Glu Gly Glu His Cys Asp Val Cys Lys Glu Gly Phe Tyr Asp Leu Ser
        435                 440                 445
Ser Glu Asp Pro Phe Gly Cys Lys Ser Cys Ala Cys Asn Pro Leu Gly
450                 455                 460
```

```
Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
                500                 505                 510

Asp Leu Gly Gly Ala Leu Asn Asn Ser Cys Phe Ala Glu Ser Gly Gln
                515                 520                 525

Cys Ser Cys Arg Pro His Met Ile Gly Arg Gln Cys Asn Glu Val Glu
            530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
                580                 585                 590

Glu Gly Ala Tyr Leu Glu Phe Phe Ile Asp Asn Ile Pro Tyr Ser Met
                595                 600                 605

Glu Tyr Asp Ile Leu Ile Arg Tyr Glu Pro Gln Leu Pro Asp His Trp
            610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
                660                 665                 670

Glu Lys Gly Thr Asn Tyr Thr Val Arg Leu Glu Leu Pro Gln Tyr Thr
                675                 680                 685

Ser Ser Asp Ser Asp Val Glu Ser Pro Tyr Thr Leu Ile Asp Ser Leu
            690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
                740                 745                 750

Asp Val Cys Arg Asn Ile Ile Phe Ser Ile Ser Ala Leu Leu His Gln
            755                 760                 765

Thr Gly Leu Ala Cys Glu Cys Asp Pro Gln Gly Ser Leu Ser Ser Val
770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
            820                 825                 830

Cys Asn Pro Val Thr Gly Gln Cys His Cys Phe Gln Gly Val Tyr Ala
            835                 840                 845

Arg Gln Cys Asp Arg Cys Leu Pro Gly His Trp Gly Phe Pro Ser Cys
            850                 855                 860

Gln Pro Cys Gln Cys Asn Gly His Ala Asp Asp Cys Asp Pro Val Thr
865                 870                 875                 880
```

```
Gly Glu Cys Leu Asn Cys Gln Asp Tyr Thr Met Gly His Asn Cys Glu
                885                 890                 895

Arg Cys Leu Ala Gly Tyr Tyr Gly Asp Pro Ile Ile Gly Ser Gly Asp
            900                 905                 910

His Cys Arg Pro Cys Pro Cys Pro Asp Gly Pro Asp Ser Gly Arg Gln
            915                 920                 925

Phe Ala Arg Ser Cys Tyr Gln Asp Pro Val Thr Leu Gln Leu Ala Cys
        930                 935                 940

Val Cys Asp Pro Gly Tyr Ile Gly Ser Arg Cys Asp Asp Cys Ala Ser
945                 950                 955                 960

Gly Tyr Phe Gly Asn Pro Ser Glu Val Gly Gly Ser Cys Gln Pro Cys
                965                 970                 975

Gln Cys His Asn Asn Ile Asp Thr Thr Asp Pro Glu Ala Cys Asp Lys
            980                 985                 990

Glu Thr Gly Arg Cys Leu Lys Cys Leu Tyr His Thr Glu Gly Glu His
            995                 1000                1005

Cys Gln Phe Cys Arg Phe Gly Tyr Tyr Gly Asp Ala Leu Gln Gln
    1010                1015                1020

Asp Cys Arg Lys Cys Val Cys Asn Tyr Leu Gly Thr Val Gln Glu
    1025                1030                1035

His Cys Asn Gly Ser Asp Cys Gln Cys Asp Lys Ala Thr Gly Gln
    1040                1045                1050

Cys Leu Cys Leu Pro Asn Val Ile Gly Gln Asn Cys Asp Arg Cys
    1055                1060                1065

Ala Pro Asn Thr Trp Gln Leu Ala Ser Gly Thr Gly Cys Asp Pro
    1070                1075                1080

Cys Asn Cys Asn Ala Ala His Ser Phe Gly Pro Ser Cys Asn Glu
    1085                1090                1095

Phe Thr Gly Gln Cys Gln Cys Met Pro Gly Phe Gly Gly Arg Thr
    1100                1105                1110

Cys Ser Glu Cys Gln Glu Leu Phe Trp Gly Asp Pro Asp Val Glu
    1115                1120                1125

Cys Arg Ala Cys Asp Cys Asp Pro Arg Gly Ile Glu Thr Pro Gln
    1130                1135                1140

Cys Asp Gln Ser Thr Gly Gln Cys Val Cys Val Glu Gly Val Glu
    1145                1150                1155

Gly Pro Arg Cys Asp Lys Cys Thr Arg Gly Tyr Ser Gly Val Phe
    1160                1165                1170

Pro Asp Cys Thr Pro Cys His Gln Cys Phe Ala Leu Trp Asp Val
    1175                1180                1185

Ile Ile Ala Glu Leu Thr Asn Arg Thr His Arg Phe Leu Glu Lys
    1190                1195                1200

Ala Lys Ala Leu Lys Ile Ser Gly Val Ile Gly Pro Tyr Arg Glu
    1205                1210                1215

Thr Val Asp Ser Val Glu Arg Lys Val Ser Glu Ile Lys Asp Ile
    1220                1225                1230

Leu Ala Gln Ser Pro Ala Ala Glu Pro Leu Lys Asn Ile Gly Asn
    1235                1240                1245

Leu Phe Glu Glu Ala Glu Lys Leu Ile Lys Asp Val Thr Glu Met
    1250                1255                1260

Met Ala Gln Val Glu Val Lys Leu Ser Asp Thr Thr Ser Gln Ser
    1265                1270                1275
```

```
Asn Ser Thr Ala Lys Glu Leu Asp Ser Leu Gln Thr Glu Ala Glu
    1280                1285                1290

Ser Leu Asp Asn Thr Val Lys Glu Leu Ala Glu Gln Leu Glu Phe
    1295                1300                1305

Ile Lys Asn Ser Asp Ile Arg Gly Ala Leu Asp Ser Ile Thr Lys
    1310                1315                1320

Tyr Phe Gln Met Ser Leu Glu Ala Glu Arg Val Asn Ala Ser
    1325                1330                1335

Thr Thr Glu Pro Asn Ser Thr Val Glu Gln Ser Ala Leu Met Arg
    1340                1345                1350

Asp Arg Val Glu Asp Val Met Met Glu Arg Glu Ser Gln Phe Lys
    1355                1360                1365

Glu Lys Gln Glu Glu Gln Ala Arg Leu Leu Asp Glu Leu Ala Gly
    1370                1375                1380

Lys Leu Gln Ser Leu Asp Leu Ser Ala Ala Ala Glu Met Thr Cys
    1385                1390                1395

Gly Thr Pro Pro Gly Ala Ser Cys Ser Gly Thr Glu Cys Gly Gly
    1400                1405                1410

Pro Asn Cys Arg Thr Asp Glu Gly Glu Arg Lys Cys Gly Gly Pro
    1415                1420                1425

Gly Cys Gly Gly Leu Val Thr Val Ala His Asn Ala Trp Gln Lys
    1430                1435                1440

Ala Met Asp Leu Asp Gln Asp Val Leu Ser Ala Leu Ala Glu Val
    1445                1450                1455

Glu Gln Leu Ser Lys Met Val Ser Glu Ala Lys Leu Arg Ala Asp
    1460                1465                1470

Glu Ala Lys Gln Ser Ala Glu Asp Ile Leu Leu Lys Thr Asn Ala
    1475                1480                1485

Thr Lys Glu Lys Met Asp Lys Ser Asn Glu Glu Leu Arg Asn Leu
    1490                1495                1500

Ile Lys Gln Ile Arg Asn Phe Leu Thr Gln Asp Ser Ala Asp Leu
    1505                1510                1515

Asp Ser Ile Glu Ala Val Ala Asn Glu Val Leu Lys Met Glu Met
    1520                1525                1530

Pro Ser Thr Pro Gln Gln Leu Gln Asn Leu Thr Glu Asp Ile Arg
    1535                1540                1545

Glu Arg Val Glu Ser Leu Ser Gln Val Glu Val Ile Leu Gln His
    1550                1555                1560

Ser Ala Ala Asp Ile Ala Arg Ala Glu Met Leu Leu Glu Glu Ala
    1565                1570                1575

Lys Arg Ala Ser Lys Ser Ala Thr Asp Val Lys Val Thr Ala Asp
    1580                1585                1590

Met Val Lys Glu Ala Leu Glu Ala Glu Lys Ala Gln Val Ala
    1595                1600                1605

Ala Glu Lys Ala Ile Lys Gln Ala Asp Glu Asp Ile Gln Gly Thr
    1610                1615                1620

Gln Asn Leu Leu Thr Ser Ile Glu Ser Glu Thr Ala Ala Ser Glu
    1625                1630                1635

Glu Thr Leu Phe Asn Ala Ser Gln Arg Ile Ser Glu Leu Glu Arg
    1640                1645                1650

Asn Val Glu Glu Leu Lys Arg Lys Ala Ala Gln Asn Ser Gly Glu
    1655                1660                1665
```

| | | | | | | | | | | |
|---|---|---|---|---|---|---|---|---|---|---|
|Ala|Glu|Tyr|Ile|Glu|Lys|Val|Val|Tyr|Thr|Val|Lys|Gln|Ser|Ala|
| |1670| | | |1675| | | |1680| |

| | | | | | | | | | | |
|---|---|---|---|---|---|---|---|---|---|---|
|Glu|Asp|Val|Lys|Lys|Thr|Leu|Asp|Gly|Glu|Leu|Asp|Glu|Lys|Tyr|
| |1685| | | |1690| | | |1695| |

| | | | | | | | | | | |
|---|---|---|---|---|---|---|---|---|---|---|
|Lys|Lys|Val|Glu|Asn|Leu|Ile|Ala|Lys|Lys|Thr|Glu|Glu|Ser|Ala|
| |1700| | | |1705| | | |1710| |

| | | | | | | | | | | |
|---|---|---|---|---|---|---|---|---|---|---|
|Asp|Ala|Arg|Arg|Lys|Ala|Glu|Met|Leu|Gln|Asn|Glu|Ala|Lys|Thr|
| |1715| | | |1720| | | |1725| |

| | | | | | | | | | | |
|---|---|---|---|---|---|---|---|---|---|---|
|Leu|Leu|Ala|Gln|Ala|Asn|Ser|Lys|Leu|Gln|Leu|Leu|Lys|Asp|Leu|
| |1730| | | |1735| | | |1740| |

| | | | | | | | | | | |
|---|---|---|---|---|---|---|---|---|---|---|
|Glu|Arg|Lys|Tyr|Glu|Asp|Asn|Gln|Arg|Tyr|Leu|Glu|Asp|Lys|Ala|
| |1745| | | |1750| | | |1755| |

| | | | | | | | | | | |
|---|---|---|---|---|---|---|---|---|---|---|
|Gln|Glu|Leu|Ala|Arg|Leu|Glu|Gly|Glu|Val|Arg|Ser|Leu|Leu|Lys|
| |1760| | | |1765| | | |1770| |

| | | | | | | | |
|---|---|---|---|---|---|---|---|
|Asp|Ile|Ser|Gln|Lys|Val|Ala|Val|Tyr|Ser|Thr|Cys|Leu|
| |1775| | | |1780| | | |1785|

<210> SEQ ID NO 5
<211> LENGTH: 5817
<212> TYPE: DNA
<213> ORGANISM: Homo sapiens

<400> SEQUENCE: 5

```
gaaggcagtt tccggaggga aggggtaggg ttggggtggg ggcgctctcc gcccggtgtt      60
gcgctccttc ccagaatccg ctccggcctt tccttcctgc cgcgattccc aactttgctc     120
aaagtcgctg gactctaagc tgtcggaggg accgctggac agacctggga actgacagag     180
ggcctggagg gaaacaggcc aaagacccac aggcagagtt gacacggaac cccaaagcaa     240
ggaggagggc tcgggcccga gaccgttcac ctccccttat ccctgttccc ctcttcagga     300
tggagctgac ctcaagggaa agagggaggg gacagcctct gccctgggaa cttcgactgg     360
gcctactgct aagcgtgctg gctgccacac tggcacaggc ccctgccccg gatgtgcctg     420
gctgttccag gggaagctgc taccccgcca cgggcgacct gctggtgggc cgagctgaca     480
gactgactgc ctcatccact tgtggcctga atggccccca gccctactgc atcgtcagtc     540
acctgcagga cgaaaagaag tgcttccttt gtgactcccg cgcccccttc tctgctagag     600
acaacccaca cagccatcgc atccagaatg tagtcaccag ctttgcacca cagcggcggg     660
cagcctggtg gcagtcagag aatggtatcc ctgcggtcac catccagctg acctggagg      720
ctgagtttca tttcacacac ctcattatga ccttcaagac atttcgccct gctgccatgc     780
tggtggaacg ctcagcagac tttggccgca cctggcatgt gtaccgatat ttctcctatg     840
actgtggggc tgacttccca ggagtccac tagcacccc acggcactgg gatgatgtag      900
tctgtgagtc ccgctactca gagattgagc catccactga aggcgaggtc atctatcgtg     960
tgctggaccc tgccatccct atcccagacc cctacagctc acggattcag aacctgttga    1020
agatcaccaa cctacgggtg aacctgactc gtctacacac gttgggagac aacctactcg    1080
acccacggag ggagatccga gagaagtact actatgccct ctatgagctg gttgtacgtg    1140
gcaactgctt ctgctacgga cacgcctcag agtgtgcacc cgcccagggg caccagccc     1200
atgctgaggg catggtgcac ggagcttgca tctgcaaaca caacacacgt ggcctcaact    1260
gcgagcagtg tcaggatttc tatcgtgacc tgccctggcg tccggctgag gacggccata    1320
gtcatgcctg taggaagtgt gagtgccatg gcacaccca cagctgccac ttcgacatgg    1380
```

```
ccgtatacct ggcatctggc aatgtgagtg gaggtgtgtg tgatggatgt cagcataaca    1440
cagctgggcg ccactgtgag ctctgtcggc ccttcttcta ccgtgaccca accaaggacc    1500
tgcgggatcc ggctgtgtgc cgctcctgtg attgtgaccc catgggttct caagacggtg    1560
gtcgctgtga ttcccatgat gaccctgcac tgggactggt ctccggccag tgtcgctgca    1620
aagaacatgt ggtgggcact cgctgccagc aatgccgtga tggcttcttt gggctcagca    1680
tcagtgaccg tctgggctgc cggcgatgtc aatgtaatgc acggggcaca gtgcctggga    1740
gcactccttg tgaccccaac agtggatcct gttactgcaa acgtctagtg actggacgtg    1800
gatgtgaccg ctgcctgcct ggccactggg cctgagcca cgacctgctc ggctgccgcc    1860
cctgtgactg cgacgtgggt ggtgctttgg atccccagtg tgatgagggc acaggtcaat    1920
gccactgccg ccagcacatg gttgggcgac gctgtgagca ggtgcaacct ggctacttcc    1980
ggcccttcct ggaccaccta atttggggagg ctgaggacac ccgagggcag gtgctcgatg    2040
tggtggagcg cctggtgacc cccgggggaaa ctccatcctg gactggctca ggcttcgtgc    2100
ggctacagga aggtcagacc ctggagttcc tggtggcctc tgtgccgaag gctatggact    2160
atgacctgct gctgcgctta gagccccagg tccctgagca atgggcagag ttggaactga    2220
ttgtgcagcg tccagggcct gtgcctgccc acagcctgtg tgggcatttg gtgcccaagg    2280
atgatcgcat ccaagggact ctgcaaccac atgccaggta cttgatattt cctaatcctg    2340
tctgccttga gcctggtatc tcctacaagc tgcatctgaa gctggtacgg acaggggaa    2400
gtgcccagcc tgagactccc tactctggac ctggcctgct cattgactcg ctggtgctgc    2460
tgccccgtgt cctggtgcta gagatgttta gtggggggtga tgctgctgcc ctggagcgcc    2520
aggccacctt tgaacgctac caatgccatg aggagggtct ggtgcccagc aagacttctc    2580
cctctgaggc ctgcgcaccc ctcctcatca gcctgtccac cctcatctac aatggtgccc    2640
tgccatgtca gtgcaaccct caaggttcac tgagttctga gtgcaaccct catggtggtc    2700
agtgcctgtg caagcctgga gtggttgggc gccgctgtga cctctgtgcc cctggctact    2760
atggctttgg ccccacaggc tgtcaagcct gccagtgcag ccacgagggg gcactcagca    2820
gtctctgtga aaagaccagt gggcaatgtc tctgtcgaac tggtgccttt gggcttcgct    2880
gtgaccgctg ccagcgtggc cagtggggat tccctagctg ccggccatgt gtctgcaatg    2940
ggcatgcaga tgagtgcaac acccacacag gcgcttgcct gggctgccgt gatcacacag    3000
ggggtgagca ctgtgaaagg tgcattgctg gttttccacgg ggacccacgg ctgccatatg    3060
ggggccagtg ccggccctgt ccctgtcctg aaggccctgg gagccaacgg cactttgcta    3120
cttcttgcca ccaggatgaa tattcccagc agattgtgtg ccactgccgg gcaggctata    3180
cggggctgcg atgtgaagct tgtgcccctg ggcactttgg ggacccatca aggccaggtg    3240
gccggtgcca actgtgtgag tgcagtggga acattgaccc aatggatcct gatgcctgtg    3300
acccccacac ggggcaatgc ctgcgctgtt tacaccacac agagggtcca cactgtgccc    3360
actgcaagcc tggcttccat gggcaggctg cccgacagag ctgtcaccgc tgcacatgca    3420
acctgctggg cacaaatccg cagcagtgcc catctcctga ccagtgccac tgtgatccaa    3480
gcagtgggca gtgcccatgc ctccccaatg tccaggccc tagctgtgac cgctgtgccc    3540
ccaacttctg gaacctcacc agtggccatg gttgccagcc ttgtgcctgc acccaagcc    3600
gggccagagg ccccacctgc aacgagttca caggcagtg ccactgccgt gccggctttg    3660
gagggcggac ttgttctgag tgccaagagc tccactgggg agaccctggg ttgcagtgcc    3720
atgcctgtga ttgtgactct cgtggaatag atacacctca gtgtcaccgc ttcacaggtc    3780
```

```
actgcagctg ccgcccaggg gtgtctggtg tgcgctgtga ccagtgtgcc cgtggcttct    3840
caggaatctt tcctgcctgc catccctgcc atgcatgctt cggggattgg gaccgagtgg    3900
tgcaggactt ggcagcccgt acacagcgcc tagagcagcg ggcgcaggag ttgcaacaga    3960
cgggtgtgct gggtgccttt gagagcagct tctggcacat gcaggagaag ctgggcattg    4020
tgcagggcat cgtaggtgcc cgcaacacct cagccgcctc cactgcacag cttgtggagg    4080
ccacagagga gctgcggcgt gaaattgggg aggccactga gcacctgact cagctcgagg    4140
cagacctgac agatgtgcaa gatgagaact tcaatgccaa ccatgcacta agtggtctgg    4200
agcgagatag gcttgcactt aatctcacac tgccggcagct cgaccagcat cttgacttgc    4260
tcaaacattc aaacttcctg ggtgcctatg acagcatccg gcatgcccat agccagtctg    4320
cagaggcaga acgtcgtgcc aatacctcag ccctggcagt acctagccct gtgagcaact    4380
cggcaagtgc tcggcatcgg acagaggcac tgatggatgc tcagaaggag gacttcaaca    4440
gcaaacacat ggccaaccag cgggcacttg gcaagctctc tgcccatacc cacaccctga    4500
gcctgacaga cataaatgag ctggtgtgtg gggcaccagg ggatgcaccc tgtgctacaa    4560
gcccttgtgg gggtgccggc tgtcgagatg aggatgggca gccgcgctgt gggggcctca    4620
gctgcaatgg ggcagcggct acagcagacc tagcactggg ccgggcccgg cacacacagg    4680
cagagctgca gcgggcactg gcagaaggtg gtagcatcct cagcagagtg gctgagactc    4740
gtcggcaggc aagcgaggca cagcagcggg cccaggcagc cctggacaag gctaatgctt    4800
ccaggggaca ggtggaacag gccaaccagg aacttcaaga acttatccag agtgtgaagg    4860
acttcctcaa ccaggagggg gctgatcctg atagcattga aatggtggcc acacgggtgc    4920
tagagctctc catcccagct tcagctgagc agatccagca cctggcgggt gcgattgcag    4980
agcgagtccg gagcctggca gatgtggatg cgatcctggc acgtactgta ggagatgtgc    5040
gtcgtgccga gcagctactg caggatgcac ggcgggcaag gagctgggct gaggatgaga    5100
aacagaaggc agagacagta caggcagcac tggaggaggc ccagcgggca cagggtattg    5160
cccagggtgc catccggggg gcagtggctg acacacggga cacagagcag accctgtacc    5220
aggtacagga gaggatggca ggtgcagagc gggcactgag ctctgcaggt gaaagggctc    5280
ggcagttgga tgctctcctg gaggctctga aattgaaacg ggcaggaaat agtctggcag    5340
cctctacagc agaagaaacg gcaggcagtg cccaggtcg tgcccaggag ctgagcagc    5400 tgctacgcgg tcctctgggt gatcagtacc agacggtgaa ggccctagct gagcgcaagg    5460
cccaaggtgt gctggctgca caggcaaggg cagaacaact gcgggatgag gctcgggacc    5520
tgttgcaagc cgctcaggac aagctgcagc ggctacagga attggaaggc acctatgagg    5580
aaaatgagcg ggcactggag agtaaggcag cccagttgga cgggttggag gccaggatgc    5640
gcagcgtgct tcaagccatc aacttgcagg tgcagatcta caacacctgc cagtgacccc    5700
tgcccaaggc ctaccccagt tcctagcact gccccacatg catgtctgcc tatgcactga    5760
agagctcttg gcccggcagg gcccccaata aaccagtgtg aaccccaaa aaaaaaa      5817
```

<210> SEQ ID NO 6
<211> LENGTH: 1798
<212> TYPE: PRT
<213> ORGANISM: Homo sapiens

<400> SEQUENCE: 6

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Gly Asp Leu Leu Val Gly Arg Ala Asp Arg Leu Thr Ala
50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
        115                 120                 125

Gly Ile Pro Ala Val Thr Ile Gln Leu Asp Leu Glu Ala Glu Phe His
130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
            180                 185                 190

Pro Pro Arg His Trp Asp Asp Val Val Cys Glu Ser Arg Tyr Ser Glu
        195                 200                 205

Ile Glu Pro Ser Thr Glu Gly Glu Val Ile Tyr Arg Val Leu Asp Pro
210                 215                 220

Ala Ile Pro Ile Pro Asp Pro Tyr Ser Ser Arg Ile Gln Asn Leu Leu
225                 230                 235                 240

Lys Ile Thr Asn Leu Arg Val Asn Leu Thr Arg Leu His Thr Leu Gly
                245                 250                 255

Asp Asn Leu Leu Asp Pro Arg Arg Glu Ile Arg Glu Lys Tyr Tyr Tyr
            260                 265                 270

Ala Leu Tyr Glu Leu Val Val Arg Gly Asn Cys Phe Cys Tyr Gly His
        275                 280                 285

Ala Ser Glu Cys Ala Pro Ala Pro Gly Ala Pro Ala His Ala Glu Gly
290                 295                 300

Met Val His Gly Ala Cys Ile Cys Lys His Asn Thr Arg Gly Leu Asn
305                 310                 315                 320

Cys Glu Gln Cys Gln Asp Phe Tyr Arg Asp Leu Pro Trp Arg Pro Ala
                325                 330                 335

Glu Asp Gly His Ser His Ala Cys Arg Lys Cys Glu Cys His Gly His
            340                 345                 350

Thr His Ser Cys His Phe Asp Met Ala Val Tyr Leu Ala Ser Gly Asn
        355                 360                 365

Val Ser Gly Gly Val Cys Asp Gly Cys Gln His Asn Thr Ala Gly Arg
370                 375                 380

His Cys Glu Leu Cys Arg Pro Phe Phe Tyr Arg Asp Pro Thr Lys Asp
385                 390                 395                 400

Leu Arg Asp Pro Ala Val Cys Arg Ser Cys Asp Cys Asp Pro Met Gly
                405                 410                 415

Ser Gln Asp Gly Gly Arg Cys Asp Ser His Asp Pro Ala Leu Gly
            420                 425                 430

```
Leu Val Ser Gly Gln Cys Arg Cys Lys Glu His Val Gly Thr Arg
            435                 440                 445

Cys Gln Gln Cys Arg Asp Gly Phe Phe Gly Leu Ser Ile Ser Asp Arg
450                 455                 460

Leu Gly Cys Arg Arg Cys Gln Cys Asn Ala Arg Gly Thr Val Pro Gly
465                 470                 475                 480

Ser Thr Pro Cys Asp Pro Asn Ser Gly Ser Cys Tyr Cys Lys Arg Leu
                485                 490                 495

Val Thr Gly Arg Gly Cys Asp Arg Cys Leu Pro Gly His Trp Gly Leu
            500                 505                 510

Ser His Asp Leu Leu Gly Cys Arg Pro Cys Asp Cys Asp Val Gly Gly
        515                 520                 525

Ala Leu Asp Pro Gln Cys Asp Glu Gly Thr Gly Gln Cys His Cys Arg
530                 535                 540

Gln His Met Val Gly Arg Arg Cys Glu Gln Val Gln Pro Gly Tyr Phe
545                 550                 555                 560

Arg Pro Phe Leu Asp His Leu Ile Trp Glu Ala Glu Asp Thr Arg Gly
                565                 570                 575

Gln Val Leu Asp Val Val Glu Arg Leu Val Thr Pro Gly Glu Thr Pro
            580                 585                 590

Ser Trp Thr Gly Ser Gly Phe Val Arg Leu Gln Glu Gly Gln Thr Leu
        595                 600                 605

Glu Phe Leu Val Ala Ser Val Pro Lys Ala Met Asp Tyr Asp Leu Leu
610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
            660                 665                 670

Arg Tyr Leu Ile Phe Pro Asn Pro Val Cys Leu Glu Pro Gly Ile Ser
        675                 680                 685

Tyr Lys Leu His Leu Lys Leu Val Arg Thr Gly Gly Ser Ala Gln Pro
690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
            740                 745                 750

Gly Leu Val Pro Ser Lys Thr Ser Pro Ser Glu Ala Cys Ala Pro Leu
        755                 760                 765

Leu Ile Ser Leu Ser Thr Leu Ile Tyr Asn Gly Ala Leu Pro Cys Gln
770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Gly Arg Arg Cys Asp Leu Cys
                805                 810                 815

Ala Pro Gly Tyr Tyr Gly Phe Gly Pro Thr Gly Cys Gln Ala Cys Gln
            820                 825                 830

Cys Ser His Glu Gly Ala Leu Ser Ser Leu Cys Glu Lys Thr Ser Gly
        835                 840                 845
```

Gln Cys Leu Cys Arg Thr Gly Ala Phe Gly Leu Arg Cys Asp Arg Cys
850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                    885                 890                 895

Arg Asp His Thr Gly Gly Glu His Cys Glu Arg Cys Ile Ala Gly Phe
                900                 905                 910

His Gly Asp Pro Arg Leu Pro Tyr Gly Gly Gln Cys Arg Pro Cys Pro
            915                 920                 925

Cys Pro Glu Gly Pro Gly Ser Gln Arg His Phe Ala Thr Ser Cys His
930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
                965                 970                 975

Ser Arg Pro Gly Gly Arg Cys Gln Leu Cys Glu Cys Ser Gly Asn Ile
            980                 985                 990

Asp Pro Met Asp Pro Asp Ala Cys Asp Pro His Thr Gly Gln Cys Leu
        995                 1000                1005

Arg Cys Leu His His Thr Glu Gly Pro His Cys Ala His Cys Lys
    1010                1015                1020

Pro Gly Phe His Gly Gln Ala Ala Arg Gln Ser Cys His Arg Cys
    1025                1030                1035

Thr Cys Asn Leu Leu Gly Thr Asn Pro Gln Gln Cys Pro Ser Pro
    1040                1045                1050

Asp Gln Cys His Cys Asp Pro Ser Ser Gly Gln Cys Pro Cys Leu
    1055                1060                1065

Pro Asn Val Gln Gly Pro Ser Cys Asp Arg Cys Ala Pro Asn Phe
    1070                1075                1080

Trp Asn Leu Thr Ser Gly His Gly Cys Gln Pro Cys Ala Cys His
    1085                1090                1095

Pro Ser Arg Ala Arg Gly Pro Thr Cys Asn Glu Phe Thr Gly Gln
    1100                1105                1110

Cys His Cys Arg Ala Gly Phe Gly Gly Arg Thr Cys Ser Glu Cys
    1115                1120                1125

Gln Glu Leu His Trp Gly Asp Pro Gly Leu Gln Cys His Ala Cys
    1130                1135                1140

Asp Cys Asp Ser Arg Gly Ile Asp Thr Pro Gln Cys His Arg Phe
    1145                1150                1155

Thr Gly His Cys Ser Cys Arg Pro Gly Val Ser Gly Val Arg Cys
    1160                1165                1170

Asp Gln Cys Ala Arg Gly Phe Ser Gly Ile Phe Pro Ala Cys His
    1175                1180                1185

Pro Cys His Ala Cys Phe Gly Asp Trp Asp Arg Val Val Gln Asp
    1190                1195                1200

Leu Ala Ala Arg Thr Gln Arg Leu Glu Gln Arg Ala Gln Glu Leu
    1205                1210                1215

Gln Gln Thr Gly Val Leu Gly Ala Phe Glu Ser Ser Phe Trp His
    1220                1225                1230

Met Gln Glu Lys Leu Gly Ile Val Gln Gly Ile Val Gly Ala Arg
    1235                1240                1245

```
Asn Thr Ser Ala Ala Ser Thr Ala Gln Leu Val Glu Ala Thr Glu
    1250                1255                1260

Glu Leu Arg Arg Glu Ile Gly Glu Ala Thr Glu His Leu Thr Gln
    1265                1270                1275

Leu Glu Ala Asp Leu Thr Asp Val Gln Asp Glu Asn Phe Asn Ala
    1280                1285                1290

Asn His Ala Leu Ser Gly Leu Glu Arg Asp Arg Leu Ala Leu Asn
    1295                1300                1305

Leu Thr Leu Arg Gln Leu Gln His Leu Asp Leu Leu Lys His
    1310                1315                1320

Ser Asn Phe Leu Gly Ala Tyr Asp Ser Ile Arg His Ala His Ser
    1325                1330                1335

Gln Ser Ala Glu Ala Glu Arg Arg Ala Asn Thr Ser Ala Leu Ala
    1340                1345                1350

Val Pro Ser Pro Val Ser Asn Ser Ala Ser Ala Arg His Arg Thr
    1355                1360                1365

Glu Ala Leu Met Asp Ala Gln Lys Glu Asp Phe Asn Ser Lys His
    1370                1375                1380

Met Ala Asn Gln Arg Ala Leu Gly Lys Leu Ser Ala His Thr His
    1385                1390                1395

Thr Leu Ser Leu Thr Asp Ile Asn Glu Leu Val Cys Gly Ala Pro
    1400                1405                1410

Gly Asp Ala Pro Cys Ala Thr Ser Pro Cys Gly Gly Ala Gly Cys
    1415                1420                1425

Arg Asp Glu Asp Gly Gln Pro Arg Cys Gly Gly Leu Ser Cys Asn
    1430                1435                1440

Gly Ala Ala Thr Ala Asp Leu Ala Leu Gly Arg Ala Arg His
    1445                1450                1455

Thr Gln Ala Glu Leu Gln Arg Ala Leu Ala Glu Gly Gly Ser Ile
    1460                1465                1470

Leu Ser Arg Val Ala Glu Thr Arg Arg Gln Ala Ser Glu Ala Gln
    1475                1480                1485

Gln Arg Ala Gln Ala Ala Leu Asp Lys Ala Asn Ala Ser Arg Gly
    1490                1495                1500

Gln Val Glu Gln Ala Asn Gln Glu Leu Gln Glu Leu Ile Gln Ser
    1505                1510                1515

Val Lys Asp Phe Leu Asn Gln Glu Gly Ala Asp Pro Asp Ser Ile
    1520                1525                1530

Glu Met Val Ala Thr Arg Val Leu Glu Leu Ser Ile Pro Ala Ser
    1535                1540                1545

Ala Glu Gln Ile Gln His Leu Ala Gly Ala Ile Ala Glu Arg Val
    1550                1555                1560

Arg Ser Leu Ala Asp Val Asp Ala Ile Leu Ala Arg Thr Val Gly
    1565                1570                1575

Asp Val Arg Arg Ala Glu Gln Leu Leu Gln Asp Ala Arg Arg Ala
    1580                1585                1590

Arg Ser Trp Ala Glu Asp Glu Lys Gln Lys Ala Glu Thr Val Gln
    1595                1600                1605

Ala Ala Leu Glu Glu Ala Gln Arg Ala Gln Gly Ile Ala Gln Gly
    1610                1615                1620

Ala Ile Arg Gly Ala Val Ala Asp Thr Arg Asp Thr Glu Gln Thr
    1625                1630                1635
```

```
Leu Tyr Gln Val Gln Glu Arg Met Ala Gly Ala Glu Arg Ala Leu
        1640                1645                1650
Ser Ser Ala Gly Glu Arg Ala Arg Gln Leu Asp Ala Leu Leu Glu
    1655                1660                1665
Ala Leu Lys Leu Lys Arg Ala Gly Asn Ser Leu Ala Ala Ser Thr
1670                1675                1680
Ala Glu Glu Thr Ala Gly Ser Ala Gln Gly Arg Ala Gln Glu Ala
    1685                1690                1695
Glu Gln Leu Leu Arg Gly Pro Leu Gly Asp Gln Tyr Gln Thr Val
        1700                1705                1710
Lys Ala Leu Ala Glu Arg Lys Ala Gln Gly Val Leu Ala Ala Gln
    1715                1720                1725
Ala Arg Ala Glu Gln Leu Arg Asp Glu Ala Arg Asp Leu Leu Gln
1730                1735                1740
Ala Ala Gln Asp Lys Leu Gln Arg Leu Gln Glu Leu Glu Gly Thr
    1745                1750                1755
Tyr Glu Glu Asn Glu Arg Ala Leu Glu Ser Lys Ala Ala Gln Leu
        1760                1765                1770
Asp Gly Leu Glu Ala Arg Met Arg Ser Val Leu Gln Ala Ile Asn
    1775                1780                1785
Leu Gln Val Gln Ile Tyr Asn Thr Cys Gln
        1790                1795

<210> SEQ ID NO 7
<211> LENGTH: 7889
<212> TYPE: DNA
<213> ORGANISM: Homo sapiens

<400> SEQUENCE: 7
gtgcaggctg ctcccggggt aggtgaggga agcgcggagg cggcgcgcgg gggcagtggt      60
cggcgagcag cgcggtcctc gctaggggcg cccacccgtc agtctctccg gcgcgagccg     120
ccgccaccgc ccgcgccgga gtcaggcccc tgggccccca ggctcaagca gcgaagcggc     180
ctccggggga cgccgctagg cgagaggaac gcgccggtgc ccttgccttc gccgtgaccc     240
agcgtgcggg cggcgggatg agagggagcc atcgggccgc gccggccctg cggccccggg     300
ggcggctctg gccgtgctg gccgtgctgg cggcggccgc cgcggcgggc tgtgcccagg     360
cagccatgga cgagtgcacg gacgagggcg ggcggccgca gcgctgcatg cccgagttcg     420
tcaacgccgc cttcaacgtg actgtggtgg ccaccaacac gtgtgggact ccgcccgagg     480
aatactgtgt gcagaccggg gtgaccgggg tcaccaagtc ctgtcacctg tgcgacgccg     540
ggcagcccca cctgcagcac ggggcagcct tcctgaccga ctacaacaac caggccgaca     600
ccacctggtg gcaaagccag accatgctgg ccggggtgca gtaccccagc tccatcaacc     660
tcacgctgca cctgggaaaa gcttttgaca tcacctatgt gcgtctcaag ttccacacca     720
gccgcccgga gagctttgcc atttacaagc gcacacggga agacgggccc tggattcctt     780
accagtacta cagtggttcc tgtgagaaca cctactccaa ggcaaaccgc ggcttcatca     840
ggacaggagg ggacgagcag caggccttgt gtactgatga attcagtgac atttctcccc     900
tcactggggg caacgtggcc ttttctaccc tggaaggaag gcccagcgcc tataactttg     960
acaatagccc tgtgctgcag gaatgggtaa ctgccactga catcagagta actcttaatc    1020
gcctgaacac ttttgagat gaagtgttta acgatcccaa agttctcaag tcctattatt    1080
atgccatctc tgattttgct gtaggtggca gatgtaaatg taatggacac gcaagcgagt    1140
```

```
gtatgaagaa cgaatttgat aagctggtgt gtaattgcaa acataacaca tatggagtag   1200
actgtgaaaa gtgtcttcct ttcttcaatg accggccgtg gaggagggca actgcggaaa   1260
gtgccagtga atgcctgccc tgtgattgca atggtcgatc ccaggaatgc tacttcgacc   1320
ctgaactcta tcgttccact ggccatgggg ccactgtac caactgccag ataacacag    1380 atggcgccca ctgtgagagg tgccgagaga acttcttccg ccttggcaac aatgaagcct   1440
gctcttcatg ccactgtagt cctgtgggct ctctaagcac acagtgtgat agttacggca   1500
gatgcagctg taagccagga gtgatggggg acaaatgtga ccgttgccag cctggattcc   1560
attctctcac tgaagcagga tgcaggccat gctcttgtga tccctctggc agcatagatg   1620
aatgtaatat tgaaacagga agatgtgttt gcaaagacaa tgtcgaaggc ttcaattgtg   1680
aaagatgcaa acctggattt tttaatctgg aatcatctaa tcctcggggt tgcacaccct   1740
gcttctgctt tgggcattct tctgtctgta caaacgctgt tggctacagt gtttattcta   1800
tctcctctac ctttcagatt gatgaggatg ggtggcgtgc ggaacagaga gatggctctg   1860
aagcatctct cgagtggtcc tctgagaggc aagatatcgc cgtgatctca gacagctact   1920
ttcctcggta cttcattgct cctgcaaagt tcttgggcaa gcaggtgttg agttatggtc   1980
agaacctctc cttctccttt cgagtggaca ggcgagatac tcgcctctct gcagaagacc   2040
ttgtgcttga gggagctggc ttaagagtat ctgtacccct tgatcgctcag ggcaattcct   2100 atccaagtga ccactgtg aagtatgtct tcaggctcca tgaagcaaca gattacccttt   2160 ggaggcctgc tcttacccct tttgaatttc agaagctcct aaacaacttg acctctatca   2220
agatacgtgg gacatacagt gagagaagtg ctggatattt ggatgatgtc accctggcaa   2280
gtgctcgtcc tgggcctgga gtccctgcaa cttgggtgga gtcctgcacc tgtcctgtgg   2340
gatatggagg gcagttttgt gagatgtgcc tctcaggtta cagaagagaa actcctaatc   2400
ttggaccata cagtccatgt gtgctttgcg cctgcaatgg acacagcgag acctgtgatc   2460
ctgagacagg tgtttgtaac tgcagagaca atacggctgg cccgcactgt gagaagtgca   2520
gtgatgggta ctatggagat tcaactgcag gcacctcctc cgattgccaa ccctgtccgt   2580
gtcctggagg ttcaagttgt gctgttgttc ccaagacaaa ggaggtggtg tgcaccaact   2640
gtcctactgg caccactggt aagagatgtg agctctgtga tgatggctac tttgagacc    2700 ccctgggtag aaacggccct gtgagacttt gccgcctgtg ccagtgcagt gacaacatcg   2760
atcccaatgc agttggaaat tgcaatcgct tgacgggaga atgcctgaag tgcatctata   2820
acactgctgg cttctattgt gaccggtgca aagacgaatt tttggaaat ccctggctc     2880 ccaatccagc agacaaatgc aaagcctgca ttgcaatct gtatgggacc atgaagcagc    2940
agagcagctg taacccgtg acggggcagt gtgaatgttt gcctcacgtg actggccagg   3000
actgtggtgc ttgtgaccct ggattctaca atctgcagag tgggcaaggc tgtgagaggt   3060
gtgactgcca tgcctgggc tccaccaatg ggcagtgtga catccgcacc ggccagtgtg    3120
agtgccagcc cggcatcact ggtcagcact gtgagcgctg tgaggtcaac cactttgggt   3180
ttggacctga aggctgcaaa ccctgtgact gtcatcctga gggatctctt tcacttcagt   3240
gcaaagatga tggtcgctgt gaatgcagag aaggctttgt gggaaatcgc tgtgaccagt   3300
gtgaagaaaa ctatttctac aatcggtctt ggcctggctg ccaggaatgt ccagcttgtt   3360
accggctggt aaaggataag gttgctgatc atagagtgaa gctccaggaa ttagagagtc   3420
tcatagcaaa ccttggaact ggggatgaga tggtgacaga tcaagccttc gaggatagac   3480
```

```
taaaggaagc agagagggaa gttatggacc tccttcgtga ggcccaggat gtcaaagatg    3540
ttgaccagaa tttgatggat cgcctacaga gagtgaataa cactctgtcc agccaaatta    3600
gccgtttaca gaatatccgg aataccattg aagagactgg aaacttggct gaacaagcgc    3660
gtgcccatgt agagaacaca gagcggttga ttgaaatcgc atccagagaa cttgagaaag    3720
caaaagtcgc tgctgccaat gtgtcagtca ctcagccaga atctacaggg gacccaaaca    3780
acatgactct tttggcagaa gaggctcgaa agcttgctga acgtcataaa caggaagctg    3840
atgacattgt tcgagtggca aagacagcca atgatacgtc aactgaggca tacaacctgc    3900
ttctgaggac actggcagga gaaaatcaaa cagcatttga gattgaagag cttaatagga    3960
agtatgaaca agcgaagaac atctcacagg atctggaaaa acaagctgcc cgagtacatg    4020
aggaggccaa aagggccggt gacaaagctg tggagatcta tgccagcgtg gctcagctga    4080 gcccttttgga ctctgagaca ctggagaatg aagcaaataa cataaagatg gaagctgaga    4140
atctggaaca actgattgac cagaaattaa aagattatga ggacctcaga gaagatatga    4200
gagggaagga acttgaagtc aagaaccttc tggagaaagg caagactgaa cagcagaccg    4260
cagaccaact cctagcccga gctgatgctg ccaaggccct cgctgaagaa gctgcaaaga    4320
agggacggga taccttacaa gaagctaatg acattctcaa caacctgaaa gattttgata    4380
ggcgtgtgaa cgataacaag acggccgcag aggaggcact aaggaagatt cctgccatca    4440
accagaccat cactgaagcc aatgaaaaga ccagagaagc ccagcaggcc ctgggcagtg    4500
ctgcggcgga tgccacagag gccaagaaca aggcccatga ggcggagagg atcgcgagcg    4560
ctgtccaaaa gaatgccacc agcaccaagg cagaagctga agaactttt gcagaagtta    4620 cagatctgga taatgaggtg aacaatatgt tgaagcaact gcaggaagca gaaaaagagc    4680
taaagagaaa acaagatgac gctgaccagg acatgatgat ggcagggatg gcttcacagg    4740
ctgctcaaga agccgagatc aatgccagaa aagccaaaaa ctctgttact agcctcctca    4800
gcattattaa tgacctcttg gagcagctgg ggcagctgga tacagtggac ctgaataagc    4860
taaacgagat tgaaggcacc ctaaacaaag ccaaagatga aatgaaggtc agcgatcttg    4920
ataggaaagt gtctgacctg gagaatgaag ccaagaagca ggaggctgcc atcatggact    4980
ataaccgaga tatcgaggag atcatgaagg acattcgcaa tctggaggac atcaggaaga    5040
ccttaccatc tggctgcttc aacaccccgt ccattgaaaa gcctagtgt ctttagggct    5100 ggaaggcagc atccctctga caggggggca gttgtgaggc cacagagtgc cttgacacaa    5160
agattacatt tttcagaccc ccactcctct gctgctgtcc atgactgtcc ttttgaacca    5220
ggaaaagtca cagagtttaa agagaagcaa attaaacatc ctgaatcggg aacaaagggt    5280
tttatctaat aaagtgtctc ttccattcac gttgctacct tacccacact ttcccttctg    5340
atttgcgtga ggacgtggca tcctacgtta ctgtacagtg gcataagcac atcgtgtgag    5400
cccatgtatg ctgggtaga gcaagtagcc ctcccctgtc tcatcgatac cagcagaacc    5460
tcctcagtct cagtactctt gtttctatga aggaaaagtt tggctactaa cagtagcatt    5520
gtgatggcca gtatatccag tccatggata aagaaaatgc atctgcatct cctaccctc    5580 ttccttctaa gcaaaggaa ataaacatcc tgtgccaaag gtattggtca tttagaatgt    5640
cggtagccat ccatcagtgc ttttagttat tatgagtgta ggacactgag ccatccgtgg    5700
gtcaggatgc aattatttat aaaagtctcc aggtgaacat ggctgaagat ttttctagta    5760
tattaataat tgactaggaa gatgaacttt ttttcagatc tttgggcagc tgataattta    5820
aatctggatg ggcagcttgc actcaccaat agaccaaaag acatctttg atattcttat    5880
```

| | | | | |
|---|---|---|---|---|
| aaatggaact | tacacagaag | aaatagggat | atgataacca | ctaaaatttt gttttcaaaa | 5940 |
| tcaaactaat | tcttacagct | tttttattag | ttagtcttgg | aactagtgtt aagtatctgg | 6000 |
| cagagaacag | ttaatcccta | aggtcttgac | aaaacagaag | aaaaacaagc ctcctcgtcc | 6060 |
| tagtcttttc | tagcaaaggg | ataaaactta | gatggcagct | tgtactgtca gaatcccgtg | 6120 |
| tatccatttg | ttcttctgtt | ggagagatga | gacatttgac | ccttagctcc agttttcttc | 6180 |
| tgatgtttcc | atcttccaga | atccctcaaa | aacattgtt | tgccaaatcc tggtggcaaa | 6240 |
| tacttgcact | cagtatttca | cacagctgcc | aacgctatcg | agttcctgca ctttgtgatt | 6300 |
| taaatccact | ctaaaccttc | cctctaagtg | tagagggaag | acccttacgt ggagtttcct | 6360 |
| agtgggcttc | tcaactttg | atcctcagct | ctgtggtttt | aagaccacag tgtgacagtt | 6420 |
| ccctgccaca | caccccttc | ctcctaccaa | cccacctttg | agattcatat atagccttta | 6480 |
| acactatgca | actttgtact | tgcgtagca | ggggcgggt | gggggaaag aaactattat | 6540 |
| ctgacacact | ggtgctatta | attatttcaa | atttatattt | tgtgtgaat gttttgtgtt | 6600 |
| ttgtttatca | tgattataga | ataaggaatt | tatgtaaata | tacttagtcc tatttctaga | 6660 |
| atgcacactct | gttcactttg | ctcaatttt | cctcttcact | ggcacaatgt atctgaatac | 6720 |
| ctccttccct | cccttctaga | attctttgga | ttgtactcca | aagaattgtg ccttgtgttt | 6780 |
| gcagcatctc | cattctctaa | aattaatata | attgctttcc | tccacaccca gccactgtaa | 6840 |
| agaggtaact | tgggtcctct | tccattgcag | tcctgatgat | cctaacctgc agcacggtgg | 6900 |
| ttttacaatg | ttccagagca | ggaacgccag | gttgacaagc | tatggtagga ttaggaaagt | 6960 |
| ttgctgaaga | ggatctttga | cgccacagtg | ggactagcca | ggaatgaggg agaaatgccc | 7020 |
| tttctggcaa | ttgttggagc | tggataggta | agttttataa | gggagtacat tttgactgag | 7080 |
| cacttagggc | atcaggaaca | gtgctactta | ctgatgggta | gactgggaga ggtggtgtaa | 7140 |
| cttagttctt | gatgatccca | cttcctgttt | ccatctgctt | gggatatacc agagtttacc | 7200 |
| acaagtgttt | tgacgatata | ctcctgagct | ttcactctgc | tgcttctccc aggcctcttc | 7260 |
| tactatggca | ggagatgtgg | cgtgctgttg | caaagttttc | acgtcattgt ttcctggcta | 7320 |
| gttcatttca | ttaagtggct | acatcctaac | atatgcattt | ggtcaaggtt gcagaagagg | 7380 |
| actgaagatt | gactgccaag | ctagtttggg | tgaagttcac | tccagcaagt ctcaggccac | 7440 |
| aatggggtgg | tttggtttgg | tttccttta | actttctttt | tgttatttgc ttttctcctc | 7500 |
| cacctgtgtg | gtatattttt | taagcagaat | ttattttttt | aaaataaaag gttctttaca | 7560 |
| agatgatacc | ttaattacac | tcccgcaaca | cagccattat | tttattgtct agctccagtt | 7620 |
| atctgtattt | tatgtaatgt | aattgacagg | atggctgctg | cagaatgctg gttgacacag | 7680 |
| ggattattat | actgctattt | ttccctgaat | tttttttcctt | tgaattccaa ctgtggacct | 7740 |
| tttatatgtg | ccttcacttt | agctgtttgc | cttaatctct | acagccttgc tctccggggt | 7800 |
| ggttaataaa | atgcaacact | tggcattttt | atgttttaag | aaaaacagta ttttatttat | 7860 |
| aataaaatct | gaatatttgt | aaccctttta | | | 7889 |

<210> SEQ ID NO 8
<211> LENGTH: 1609
<212> TYPE: PRT
<213> ORGANISM: Homo sapiens

<400> SEQUENCE: 8

Met Arg Gly Ser His Arg Ala Ala Pro Ala Leu Arg Pro Arg Gly Arg
1               5                   10                  15

-continued

```
Leu Trp Pro Val Leu Ala Val Leu Ala Ala Ala Ala Gly Cys
            20                  25                  30

Ala Gln Ala Ala Met Asp Glu Cys Thr Asp Glu Gly Arg Pro Gln
        35                  40                  45

Arg Cys Met Pro Glu Phe Val Asn Ala Ala Phe Asn Val Thr Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                    85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                    165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
        195                 200                 205

Phe Ser Asp Ile Ser Pro Leu Thr Gly Gly Asn Val Ala Phe Ser Thr
    210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                    245                 250                 255

Asn Thr Phe Gly Asp Glu Val Phe Asn Asp Pro Lys Val Leu Lys Ser
            260                 265                 270

Tyr Tyr Tyr Ala Ile Ser Asp Phe Ala Val Gly Gly Arg Cys Lys Cys
        275                 280                 285

Asn Gly His Ala Ser Glu Cys Met Lys Asn Glu Phe Asp Lys Leu Val
    290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                    325                 330                 335

Ser Glu Cys Leu Pro Cys Asp Cys Asn Gly Arg Ser Gln Glu Cys Tyr
            340                 345                 350

Phe Asp Pro Glu Leu Tyr Arg Ser Thr Gly His Gly Gly His Cys Thr
        355                 360                 365

Asn Cys Gln Asp Asn Thr Asp Gly Ala His Cys Glu Arg Cys Arg Glu
    370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                    405                 410                 415

Ser Cys Lys Pro Gly Val Met Gly Asp Lys Cys Asp Arg Cys Gln Pro
            420                 425                 430
```

```
Gly Phe His Ser Leu Thr Glu Ala Gly Cys Arg Pro Cys Ser Cys Asp
            435                 440                 445
Pro Ser Gly Ser Ile Asp Glu Cys Asn Ile Glu Thr Gly Arg Cys Val
450                 455                 460
Cys Lys Asp Asn Val Glu Gly Phe Asn Cys Glu Arg Cys Lys Pro Gly
465                 470                 475                 480
Phe Phe Asn Leu Glu Ser Ser Asn Pro Arg Gly Cys Thr Pro Cys Phe
            485                 490                 495
Cys Phe Gly His Ser Ser Val Cys Thr Asn Ala Val Gly Tyr Ser Val
            500                 505                 510
Tyr Ser Ile Ser Ser Thr Phe Gln Ile Asp Glu Asp Gly Trp Arg Ala
            515                 520                 525
Glu Gln Arg Asp Gly Ser Glu Ala Ser Leu Glu Trp Ser Ser Glu Arg
            530                 535                 540
Gln Asp Ile Ala Val Ile Ser Asp Ser Tyr Phe Pro Arg Tyr Phe Ile
545                 550                 555                 560
Ala Pro Ala Lys Phe Leu Gly Lys Gln Val Leu Ser Tyr Gly Gln Asn
                565                 570                 575
Leu Ser Phe Ser Phe Arg Val Asp Arg Arg Asp Thr Arg Leu Ser Ala
            580                 585                 590
Glu Asp Leu Val Leu Glu Gly Ala Gly Leu Arg Val Ser Val Pro Leu
            595                 600                 605
Ile Ala Gln Gly Asn Ser Tyr Pro Ser Glu Thr Thr Val Lys Tyr Val
            610                 615                 620
Phe Arg Leu His Glu Ala Thr Asp Tyr Pro Trp Arg Pro Ala Leu Thr
625                 630                 635                 640
Pro Phe Glu Phe Gln Lys Leu Leu Asn Asn Leu Thr Ser Ile Lys Ile
                645                 650                 655
Arg Gly Thr Tyr Ser Glu Arg Ser Ala Gly Tyr Leu Asp Asp Val Thr
            660                 665                 670
Leu Ala Ser Ala Arg Pro Gly Pro Gly Val Pro Ala Thr Trp Val Glu
            675                 680                 685
Ser Cys Thr Cys Pro Val Gly Tyr Gly Gly Gln Phe Cys Glu Met Cys
            690                 695                 700
Leu Ser Gly Tyr Arg Arg Glu Thr Pro Asn Leu Gly Pro Tyr Ser Pro
705                 710                 715                 720
Cys Val Leu Cys Ala Cys Asn Gly His Ser Glu Thr Cys Asp Pro Glu
                725                 730                 735
Thr Gly Val Cys Asn Cys Arg Asp Asn Thr Ala Gly Pro His Cys Glu
            740                 745                 750
Lys Cys Ser Asp Gly Tyr Tyr Gly Asp Ser Thr Ala Gly Thr Ser Ser
            755                 760                 765
Asp Cys Gln Pro Cys Pro Cys Pro Gly Gly Ser Ser Cys Ala Val Val
            770                 775                 780
Pro Lys Thr Lys Glu Val Val Cys Thr Asn Cys Pro Thr Gly Thr Thr
785                 790                 795                 800
Gly Lys Arg Cys Glu Leu Cys Asp Asp Gly Tyr Phe Gly Asp Pro Leu
                805                 810                 815
Gly Arg Asn Gly Pro Val Arg Leu Cys Arg Leu Cys Gln Cys Ser Asp
            820                 825                 830
Asn Ile Asp Pro Asn Ala Val Gly Asn Cys Asn Arg Leu Thr Gly Glu
            835                 840                 845
```

```
Cys Leu Lys Cys Ile Tyr Asn Thr Ala Gly Phe Tyr Cys Asp Arg Cys
850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
                885                 890                 895

Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
    930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
                965                 970                 975

Pro Glu Gly Cys Lys Pro Cys Asp Cys His Pro Glu Gly Ser Leu Ser
            980                 985                 990

Leu Gln Cys Lys Asp Asp Gly Arg Cys Glu Cys Arg Glu Gly Phe Val
        995                 1000                1005

Gly Asn Arg Cys Asp Gln Cys Glu Glu Asn Tyr Phe Tyr Asn Arg
    1010                1015                1020

Ser Trp Pro Gly Cys Gln Glu Cys Pro Ala Cys Tyr Arg Leu Val
    1025                1030                1035

Lys Asp Lys Val Ala Asp His Arg Val Lys Leu Gln Glu Leu Glu
    1040                1045                1050

Ser Leu Ile Ala Asn Leu Gly Thr Gly Asp Glu Met Val Thr Asp
    1055                1060                1065

Gln Ala Phe Glu Asp Arg Leu Lys Glu Ala Glu Arg Glu Val Met
    1070                1075                1080

Asp Leu Leu Arg Glu Ala Gln Asp Val Lys Asp Val Asp Gln Asn
    1085                1090                1095

Leu Met Asp Arg Leu Gln Arg Val Asn Asn Thr Leu Ser Ser Gln
    1100                1105                1110

Ile Ser Arg Leu Gln Asn Ile Arg Asn Thr Ile Glu Glu Thr Gly
    1115                1120                1125

Asn Leu Ala Glu Gln Ala Arg Ala His Val Glu Asn Thr Glu Arg
    1130                1135                1140

Leu Ile Glu Ile Ala Ser Arg Glu Leu Glu Lys Ala Lys Val Ala
    1145                1150                1155

Ala Ala Asn Val Ser Val Thr Gln Pro Glu Ser Thr Gly Asp Pro
    1160                1165                1170

Asn Asn Met Thr Leu Leu Ala Glu Glu Ala Arg Lys Leu Ala Glu
    1175                1180                1185

Arg His Lys Gln Glu Ala Asp Asp Ile Val Arg Val Ala Lys Thr
    1190                1195                1200

Ala Asn Asp Thr Ser Thr Glu Ala Tyr Asn Leu Leu Leu Arg Thr
    1205                1210                1215

Leu Ala Gly Glu Asn Gln Thr Ala Phe Glu Ile Glu Glu Leu Asn
    1220                1225                1230

Arg Lys Tyr Glu Gln Ala Lys Asn Ile Ser Gln Asp Leu Glu Lys
    1235                1240                1245
```

Gln Ala Arg Val His Glu Glu Ala Lys Arg Ala Gly Asp Lys
1250              1255             1260

Ala Val Glu Ile Tyr Ala Ser Val Ala Gln Leu Ser Pro Leu Asp
1265              1270             1275

Ser Glu Thr Leu Glu Asn Glu Ala Asn Asn Ile Lys Met Glu Ala
1280              1285             1290

Glu Asn Leu Glu Gln Leu Ile Asp Gln Lys Leu Lys Asp Tyr Glu
1295              1300             1305

Asp Leu Arg Glu Asp Met Arg Gly Lys Glu Leu Glu Val Lys Asn
1310              1315             1320

Leu Leu Glu Lys Gly Lys Thr Glu Gln Gln Thr Ala Asp Gln Leu
1325              1330             1335

Leu Ala Arg Ala Asp Ala Ala Lys Ala Leu Ala Glu Glu Ala Ala
1340              1345             1350

Lys Lys Gly Arg Asp Thr Leu Gln Glu Ala Asn Asp Ile Leu Asn
1355              1360             1365

Asn Leu Lys Asp Phe Asp Arg Arg Val Asn Asp Asn Lys Thr Ala
1370              1375             1380

Ala Glu Glu Ala Leu Arg Lys Ile Pro Ala Ile Asn Gln Thr Ile
1385              1390             1395

Thr Glu Ala Asn Glu Lys Thr Arg Glu Ala Gln Gln Ala Leu Gly
1400              1405             1410

Ser Ala Ala Asp Ala Thr Glu Ala Lys Asn Lys Ala His Glu
1415              1420             1425

Ala Glu Arg Ile Ala Ser Ala Val Gln Lys Asn Ala Thr Ser Thr
1430              1435             1440

Lys Ala Glu Ala Glu Arg Thr Phe Ala Glu Val Thr Asp Leu Asp
1445              1450             1455

Asn Glu Val Asn Asn Met Leu Lys Gln Leu Gln Glu Ala Glu Lys
1460              1465             1470

Glu Leu Lys Arg Lys Gln Asp Asp Ala Asp Gln Asp Met Met Met
1475              1480             1485

Ala Gly Met Ala Ser Gln Ala Ala Gln Glu Ala Glu Ile Asn Ala
1490              1495             1500

Arg Lys Ala Lys Asn Ser Val Thr Ser Leu Leu Ser Ile Ile Asn
1505              1510             1515

Asp Leu Leu Glu Gln Leu Gly Gln Leu Asp Thr Val Asp Leu Asn
1520              1525             1530

Lys Leu Asn Glu Ile Glu Gly Thr Leu Asn Lys Ala Lys Asp Glu
1535              1540             1545

Met Lys Val Ser Asp Leu Asp Arg Lys Val Ser Asp Leu Glu Asn
1550              1555             1560

Glu Ala Lys Lys Gln Glu Ala Ala Ile Met Asp Tyr Asn Arg Asp
1565              1570             1575

Ile Glu Glu Ile Met Lys Asp Ile Arg Asn Leu Glu Asp Ile Arg
1580              1585             1590

Lys Thr Leu Pro Ser Gly Cys Phe Asn Thr Pro Ser Ile Glu Lys
1595              1600             1605

Pro

<210> SEQ ID NO 9
<211> LENGTH: 22
<212> TYPE: DNA
<213> ORGANISM: Artificial sequence

```
<220> FEATURE:
<223> OTHER INFORMATION: Synthetic laminin alpha 1 chain sense primer
      sequence

<400> SEQUENCE: 9
gagtccgtct ctctggacat ag                                            22

<210> SEQ ID NO 10
<211> LENGTH: 21
<212> TYPE: DNA
<213> ORGANISM: Artificial sequence
<220> FEATURE:
<223> OTHER INFORMATION: Synthetic laminin alpha 1 chain antisense
      primer sequence

<400> SEQUENCE: 10
cgtggcattc acagggttga c                                             21

<210> SEQ ID NO 11
<211> LENGTH: 22
<212> TYPE: DNA
<213> ORGANISM: Artificial sequence
<220> FEATURE:
<223> OTHER INFORMATION: Synthetic laminin alpha 2 chain sense primer
      sequence

<400> SEQUENCE: 11
tgctagaatt tacctccgct cg                                            22

<210> SEQ ID NO 12
<211> LENGTH: 20
<212> TYPE: DNA
<213> ORGANISM: Artificial sequence
<220> FEATURE:
<223> OTHER INFORMATION: Synthetic laminin alpha 2 chain antisense
      primer sequence

<400> SEQUENCE: 12
gatcaagtgg acaagccctg                                               20

<210> SEQ ID NO 13
<211> LENGTH: 20
<212> TYPE: DNA
<213> ORGANISM: Artificial sequence
<220> FEATURE:
<223> OTHER INFORMATION: Synthetic laminin alpha 3 chain sense primer
      sequence

<400> SEQUENCE: 13
ctccaaaggc ccaactcaag                                               20

<210> SEQ ID NO 14
<211> LENGTH: 22
<212> TYPE: DNA
<213> ORGANISM: Artificial sequence
<220> FEATURE:
<223> OTHER INFORMATION: Synthetic laminin alpha 3 chain antisense
      primer sequence

<400> SEQUENCE: 14
ccataactgc ctccttagtc tc                                            22

<210> SEQ ID NO 15
<211> LENGTH: 22
<212> TYPE: DNA
<213> ORGANISM: Artificial sequence
<220> FEATURE:
```

```
<223> OTHER INFORMATION: Synthetic laminin alpha 4 chain sense primer
      sequence

<400> SEQUENCE: 15
cttacgcaac accaccggat tc                                              22

<210> SEQ ID NO 16
<211> LENGTH: 21
<212> TYPE: DNA
<213> ORGANISM: Artificial sequence
<220> FEATURE:
<223> OTHER INFORMATION: Synthetic laminin alpha 4 chain antisense
      primer sequence

<400> SEQUENCE: 16
ccttcttcca agcattctcc g                                               21

<210> SEQ ID NO 17
<211> LENGTH: 22
<212> TYPE: DNA
<213> ORGANISM: Artificial sequence
<220> FEATURE:
<223> OTHER INFORMATION: Synthetic laminin alpha 5 chain sense primer
      sequence

<400> SEQUENCE: 17
gaggactgaa gtgaaaactc aa                                              22

<210> SEQ ID NO 18
<211> LENGTH: 21
<212> TYPE: DNA
<213> ORGANISM: Artificial sequence
<220> FEATURE:
<223> OTHER INFORMATION: Synthetic laminin alpha 5 chain antisense
      primer sequence

<400> SEQUENCE: 18
ccactgaagt tgtaaatggt g                                               21

<210> SEQ ID NO 19
<211> LENGTH: 22
<212> TYPE: DNA
<213> ORGANISM: Artificial sequence
<220> FEATURE:
<223> OTHER INFORMATION: Synthetic laminin beta 1 chain sense primer
      sequence

<400> SEQUENCE: 19
gatggtgaac ttgatgaaaa gt                                              22

<210> SEQ ID NO 20
<211> LENGTH: 22
<212> TYPE: DNA
<213> ORGANISM: Artificial sequence
<220> FEATURE:
<223> OTHER INFORMATION: Synthetic laminin beta 1 chain antisense primer
      sequence

<400> SEQUENCE: 20
ggcttatatc ctttaggagt ga                                              22

<210> SEQ ID NO 21
<211> LENGTH: 20
<212> TYPE: DNA
<213> ORGANISM: Artificial sequence
```

```
<220> FEATURE:
<223> OTHER INFORMATION: Synthetic laminin beta 2 chain sense primer
      sequence

<400> SEQUENCE: 21
gatgatcgca tccaagggac                                                   20

<210> SEQ ID NO 22
<211> LENGTH: 21
<212> TYPE: DNA
<213> ORGANISM: Artificial sequence
<220> FEATURE:
<223> OTHER INFORMATION: Synthetic laminin beta 2 chain antisense primer
      sequence

<400> SEQUENCE: 22
gtccagagta gggagtctca g                                                 21

<210> SEQ ID NO 23
<211> LENGTH: 20
<212> TYPE: DNA
<213> ORGANISM: Artificial sequence
<220> FEATURE:
<223> OTHER INFORMATION: Synthetic laminin beta 3 chain sense primer
      sequence

<400> SEQUENCE: 23
cccagatgga ggaagatgtc                                                   20

<210> SEQ ID NO 24
<211> LENGTH: 20
<212> TYPE: DNA
<213> ORGANISM: Artificial sequence
<220> FEATURE:
<223> OTHER INFORMATION: Synthetic laminin beta 3 chain antisense primer
      sequence

<400> SEQUENCE: 24
gtagctgagt ctgtgggcag                                                   20

<210> SEQ ID NO 25
<211> LENGTH: 20
<212> TYPE: DNA
<213> ORGANISM: Artificial sequence
<220> FEATURE:
<223> OTHER INFORMATION: Synthetic laminin beta 4 chain sense primer
      sequence

<400> SEQUENCE: 25
ggcaggctac tttggatttc                                                   20

<210> SEQ ID NO 26
<211> LENGTH: 20
<212> TYPE: DNA
<213> ORGANISM: Artificial sequence
<220> FEATURE:
<223> OTHER INFORMATION: Synthetic laminin beta 4 chain antisense primer
      sequence

<400> SEQUENCE: 26
gcttgaggga tcatctggac                                                   20

<210> SEQ ID NO 27
<211> LENGTH: 22
<212> TYPE: DNA
<213> ORGANISM: Artificial sequence
<220> FEATURE:
```

```
<223> OTHER INFORMATION: Synthetic laminin gamma 1 chain sense primer
      sequence

<400> SEQUENCE: 27
gatgagatgg tgacagatca ag                                              22

<210> SEQ ID NO 28
<211> LENGTH: 22
<212> TYPE: DNA
<213> ORGANISM: Artificial sequence
<220> FEATURE:
<223> OTHER INFORMATION: Synthetic laminin gamma 1 chain antisense
      primer sequence

<400> SEQUENCE: 28
tttccagtct cttcaatggt at                                              22

<210> SEQ ID NO 29
<211> LENGTH: 21
<212> TYPE: DNA
<213> ORGANISM: Artificial sequence
<220> FEATURE:
<223> OTHER INFORMATION: Synthetic laminin gamma 2 chain sense primer
      sequence

<400> SEQUENCE: 29
atcgaaggtt actgcggaat c                                               21

<210> SEQ ID NO 30
<211> LENGTH: 21
<212> TYPE: DNA
<213> ORGANISM: Artificial sequence
<220> FEATURE:
<223> OTHER INFORMATION: Synthetic laminin gamma 2 chain antisense
      primer sequence

<400> SEQUENCE: 30
gtagccagaa gcacaatcct g                                               21

<210> SEQ ID NO 31
<211> LENGTH: 20
<212> TYPE: DNA
<213> ORGANISM: Artificial sequence
<220> FEATURE:
<223> OTHER INFORMATION: Synthetic laminin gamma 3 chain sense primer
      sequence

<400> SEQUENCE: 31
gggatacaag agggagatgc                                                 20

<210> SEQ ID NO 32
<211> LENGTH: 21
<212> TYPE: DNA
<213> ORGANISM: Artificial sequence
<220> FEATURE:
<223> OTHER INFORMATION: Synthetic laminin gamma 3 chain antisense
      primer sequence

<400> SEQUENCE: 32
catagaaacc tggcaaacag c                                               21

<210> SEQ ID NO 33
<211> LENGTH: 22
<212> TYPE: DNA
<213> ORGANISM: Artificial sequence
<220> FEATURE:
```

```
<223> OTHER INFORMATION: Synthetic integrin alpha 1 chain sense primer
      sequence

<400> SEQUENCE: 33
gaagaacctc ctgaaaccct tt                                                22

<210> SEQ ID NO 34
<211> LENGTH: 22
<212> TYPE: DNA
<213> ORGANISM: Artificial sequence
<220> FEATURE:
<223> OTHER INFORMATION: Synthetic integrin alpha 1 chain antisense
      primer sequence

<400> SEQUENCE: 34
tgatgtcata ttggggaatg aa                                                22

<210> SEQ ID NO 35
<211> LENGTH: 22
<212> TYPE: DNA
<213> ORGANISM: Artificial sequence
<220> FEATURE:
<223> OTHER INFORMATION: Synthetic integrin alpha 2 chain sense primer
      sequence

<400> SEQUENCE: 35
tgatgggaca gaagtaacat gc                                                22

<210> SEQ ID NO 36
<211> LENGTH: 22
<212> TYPE: DNA
<213> ORGANISM: Artificial sequence
<220> FEATURE:
<223> OTHER INFORMATION: Synthetic integrin alpha 2 chain antisense
      primer sequence

<400> SEQUENCE: 36
tggaccaaca tcttcaaaac tg                                                22

<210> SEQ ID NO 37
<211> LENGTH: 22
<212> TYPE: DNA
<213> ORGANISM: Artificial sequence
<220> FEATURE:
<223> OTHER INFORMATION: Synthetic integrin alpha 3 chain sense primer
      sequence

<400> SEQUENCE: 37
gctctgcctt tggtttatct gt                                                22

<210> SEQ ID NO 38
<211> LENGTH: 22
<212> TYPE: DNA
<213> ORGANISM: Artificial sequence
<220> FEATURE:
<223> OTHER INFORMATION: Synthetic integrin alpha 3 chain antisense
      primer sequence

<400> SEQUENCE: 38
ttcccactag aaggtctggg ta                                                22

<210> SEQ ID NO 39
<211> LENGTH: 22
<212> TYPE: DNA
<213> ORGANISM: Artificial sequence
<220> FEATURE:
```

```
<223> OTHER INFORMATION: Synthetic integrin alpha 4 chain sense primer
      sequence

<400> SEQUENCE: 39
atattcagtc ggagctggtc at                                            22

<210> SEQ ID NO 40
<211> LENGTH: 22
<212> TYPE: DNA
<213> ORGANISM: Artificial sequence
<220> FEATURE:
<223> OTHER INFORMATION: Synthetic integrin alpha 4 chain antisense
      primer sequence

<400> SEQUENCE: 40
gcatatttgt cacttccaac ga                                            22

<210> SEQ ID NO 41
<211> LENGTH: 22
<212> TYPE: DNA
<213> ORGANISM: Artificial sequence
<220> FEATURE:
<223> OTHER INFORMATION: Synthetic integrin alpha 5 chain sense primer
      sequence

<400> SEQUENCE: 41
tcctcagcaa gaatctcaac aa                                            22

<210> SEQ ID NO 42
<211> LENGTH: 22
<212> TYPE: DNA
<213> ORGANISM: Artificial sequence
<220> FEATURE:
<223> OTHER INFORMATION: Synthetic integrin alpha 5 chain antisense
      primer sequence

<400> SEQUENCE: 42
gttgagtccc gtaactctgg tc                                            22

<210> SEQ ID NO 43
<211> LENGTH: 22
<212> TYPE: DNA
<213> ORGANISM: Artificial sequence
<220> FEATURE:
<223> OTHER INFORMATION: Synthetic integrin alpha 6 chain sense primer
      sequence

<400> SEQUENCE: 43
agcaaggcag atggaataat gt                                            22

<210> SEQ ID NO 44
<211> LENGTH: 22
<212> TYPE: DNA
<213> ORGANISM: Artificial sequence
<220> FEATURE:
<223> OTHER INFORMATION: Synthetic integrin alpha 6 chain antisense
      primer sequence

<400> SEQUENCE: 44
cagggtagga atttcgatca ag                                            22

<210> SEQ ID NO 45
<211> LENGTH: 22
<212> TYPE: DNA
<213> ORGANISM: Artificial sequence
<220> FEATURE:
```

<223> OTHER INFORMATION: Synthetic integrin alpha 7 chain sense primer
      sequence

<400> SEQUENCE: 45
caggtcacct tctacctcat cc                                          22

<210> SEQ ID NO 46
<211> LENGTH: 22
<212> TYPE: DNA
<213> ORGANISM: Artificial sequence
<220> FEATURE:
<223> OTHER INFORMATION: Synthetic integrin alpha 7 chain antisense
      primer sequence

<400> SEQUENCE: 46
accgtgacct catacttgac ct                                          22

<210> SEQ ID NO 47
<211> LENGTH: 22
<212> TYPE: DNA
<213> ORGANISM: Artificial sequence
<220> FEATURE:
<223> OTHER INFORMATION: Synthetic integrin alpha 8 chain sense primer
      sequence

<400> SEQUENCE: 47
atggaaaatg taaccaggat gg                                          22

<210> SEQ ID NO 48
<211> LENGTH: 22
<212> TYPE: DNA
<213> ORGANISM: Artificial sequence
<220> FEATURE:
<223> OTHER INFORMATION: Synthetic integrin alpha 8 chain antisense
      primer sequence

<400> SEQUENCE: 48
cagttatgaa tgggcagaac aa                                          22

<210> SEQ ID NO 49
<211> LENGTH: 22
<212> TYPE: DNA
<213> ORGANISM: Artificial sequence
<220> FEATURE:
<223> OTHER INFORMATION: Synthetic integrin alpha 9 chain sense primer
      sequence

<400> SEQUENCE: 49
cactttcagc ccatcaatat ca                                          22

<210> SEQ ID NO 50
<211> LENGTH: 22
<212> TYPE: DNA
<213> ORGANISM: Artificial sequence
<220> FEATURE:
<223> OTHER INFORMATION: Synthetic integrin alpha 9 chain antisense
      primer sequence

<400> SEQUENCE: 50
acagtgtgct gttaggcaag aa                                          22

<210> SEQ ID NO 51
<211> LENGTH: 22
<212> TYPE: DNA
<213> ORGANISM: Artificial sequence
<220> FEATURE:

```
<223> OTHER INFORMATION: Synthetic integrin alpha 10 chain sense primer
      sequence

<400> SEQUENCE: 51
atcagtgtgg ttcagaggga ct                                              22

<210> SEQ ID NO 52
<211> LENGTH: 22
<212> TYPE: DNA
<213> ORGANISM: Artificial sequence
<220> FEATURE:
<223> OTHER INFORMATION: Synthetic integrin alpha 10 chain antisense
      primer sequence

<400> SEQUENCE: 52
gccctggctt tgtagtattg tc                                              22

<210> SEQ ID NO 53
<211> LENGTH: 22
<212> TYPE: DNA
<213> ORGANISM: Artificial sequence
<220> FEATURE:
<223> OTHER INFORMATION: Synthetic integrin alpha 11 chain sense primer
      sequence

<400> SEQUENCE: 53
ggacactgct gactacgtga ag                                              22

<210> SEQ ID NO 54
<211> LENGTH: 22
<212> TYPE: DNA
<213> ORGANISM: Artificial sequence
<220> FEATURE:
<223> OTHER INFORMATION: Synthetic integrin alpha 11 chain antisense
      primer sequence

<400> SEQUENCE: 54
gcgtgtgctc tctatgatga ag                                              22

<210> SEQ ID NO 55
<211> LENGTH: 22
<212> TYPE: DNA
<213> ORGANISM: Artificial sequence
<220> FEATURE:
<223> OTHER INFORMATION: Synthetic integrin alpha-E chain sense primer
      sequence

<400> SEQUENCE: 55
tagcagtgaa gaagctgacg ag                                              22

<210> SEQ ID NO 56
<211> LENGTH: 22
<212> TYPE: DNA
<213> ORGANISM: Artificial sequence
<220> FEATURE:
<223> OTHER INFORMATION: Synthetic integrin alpha-E chain antisense
      primer sequence

<400> SEQUENCE: 56
tctttcagga agacgacagt ga                                              22

<210> SEQ ID NO 57
<211> LENGTH: 22
<212> TYPE: DNA
<213> ORGANISM: Artificial sequence
<220> FEATURE:
```

```
<223> OTHER INFORMATION: Synthetic integrin alpha-V chain sense primer
      sequence

<400> SEQUENCE: 57
atctgtgagg tcgaaacagg at                                              22

<210> SEQ ID NO 58
<211> LENGTH: 22
<212> TYPE: DNA
<213> ORGANISM: Artificial sequence
<220> FEATURE:
<223> OTHER INFORMATION: Synthetic integrin alpha-V chain antisense
      primer sequence

<400> SEQUENCE: 58
accttgccaa taaaagctac ca                                              22

<210> SEQ ID NO 59
<211> LENGTH: 22
<212> TYPE: DNA
<213> ORGANISM: Artificial sequence
<220> FEATURE:
<223> OTHER INFORMATION: Synthetic integrin alpha-L chain sense primer
      sequence

<400> SEQUENCE: 59
gaaccattga caccagaagt ga                                              22

<210> SEQ ID NO 60
<211> LENGTH: 22
<212> TYPE: DNA
<213> ORGANISM: Artificial sequence
<220> FEATURE:
<223> OTHER INFORMATION: Synthetic integrin alpha-L chain antisense
      primer sequence

<400> SEQUENCE: 60
ttcttcaaac cccaactgtc tt                                              22

<210> SEQ ID NO 61
<211> LENGTH: 22
<212> TYPE: DNA
<213> ORGANISM: Artificial sequence
<220> FEATURE:
<223> OTHER INFORMATION: Synthetic integrin alpha-M chain sense primer
      sequence

<400> SEQUENCE: 61
gatcggctaa gagaaggaca ga                                              22

<210> SEQ ID NO 62
<211> LENGTH: 22
<212> TYPE: DNA
<213> ORGANISM: Artificial sequence
<220> FEATURE:
<223> OTHER INFORMATION: Synthetic integrin alpha-M chain antisense
      primer sequence

<400> SEQUENCE: 62
cattgccaca attcttctca aa                                              22

<210> SEQ ID NO 63
<211> LENGTH: 22
<212> TYPE: DNA
<213> ORGANISM: Artificial sequence
<220> FEATURE:
```

<223> OTHER INFORMATION: Synthetic integrin alpha-X chain sense primer
      sequence

<400> SEQUENCE: 63
ccaacatctg cctttacatt ga                                              22

<210> SEQ ID NO 64
<211> LENGTH: 22
<212> TYPE: DNA
<213> ORGANISM: Artificial sequence
<220> FEATURE:
<223> OTHER INFORMATION: Synthetic integrin alpha-X chain antisense
      primer sequence

<400> SEQUENCE: 64
cgtgaagtat ctctgagcat cg                                              22

<210> SEQ ID NO 65
<211> LENGTH: 22
<212> TYPE: DNA
<213> ORGANISM: Artificial sequence
<220> FEATURE:
<223> OTHER INFORMATION: Synthetic integrin alpha-D chain sense primer
      sequence

<400> SEQUENCE: 65
ttaaccagat gaagggcttt gt                                              22

<210> SEQ ID NO 66
<211> LENGTH: 22
<212> TYPE: DNA
<213> ORGANISM: Artificial sequence
<220> FEATURE:
<223> OTHER INFORMATION: Synthetic integrin alpha-D chain antisense
      primer sequence

<400> SEQUENCE: 66
ggtctttgta cttctgccca tc                                              22

<210> SEQ ID NO 67
<211> LENGTH: 22
<212> TYPE: DNA
<213> ORGANISM: Artificial sequence
<220> FEATURE:
<223> OTHER INFORMATION: Synthetic integrin alpha-IIb chain sense primer
      sequence

<400> SEQUENCE: 67
gaaaagactg aggaggctga ga                                              22

<210> SEQ ID NO 68
<211> LENGTH: 22
<212> TYPE: DNA
<213> ORGANISM: Artificial sequence
<220> FEATURE:
<223> OTHER INFORMATION: Synthetic integrin alpha-IIb chain antisense
      primer sequence

<400> SEQUENCE: 68
gagaaaatat ccgcaactgg ag                                              22

<210> SEQ ID NO 69
<211> LENGTH: 22
<212> TYPE: DNA
<213> ORGANISM: Artificial sequence
<220> FEATURE:

-continued

```
<223> OTHER INFORMATION: Synthetic integrin beta 1 chain sense primer
      sequence

<400> SEQUENCE: 69
gctgaagact atcccattga cc                                             22

<210> SEQ ID NO 70
<211> LENGTH: 22
<212> TYPE: DNA
<213> ORGANISM: Artificial sequence
<220> FEATURE:
<223> OTHER INFORMATION: Synthetic integrin beta 1 chain antisense
      primer sequence

<400> SEQUENCE: 70
atttccagat atgcgctgtt tt                                             22

<210> SEQ ID NO 71
<211> LENGTH: 22
<212> TYPE: DNA
<213> ORGANISM: Artificial sequence
<220> FEATURE:
<223> OTHER INFORMATION: Synthetic integrin beta 2 chain sense primer
      sequence

<400> SEQUENCE: 71
tgatggacct ctcctactcc at                                             22

<210> SEQ ID NO 72
<211> LENGTH: 22
<212> TYPE: DNA
<213> ORGANISM: Artificial sequence
<220> FEATURE:
<223> OTHER INFORMATION: Synthetic integrin beta 2 chain antisense
      primer sequence

<400> SEQUENCE: 72
gaaactggtt ggagttgttg gt                                             22

<210> SEQ ID NO 73
<211> LENGTH: 22
<212> TYPE: DNA
<213> ORGANISM: Artificial sequence
<220> FEATURE:
<223> OTHER INFORMATION: Synthetic integrin beta 3 chain sense primer
      sequence

<400> SEQUENCE: 73
tgtttaccac tgatgccaag ac                                             22

<210> SEQ ID NO 74
<211> LENGTH: 22
<212> TYPE: DNA
<213> ORGANISM: Artificial sequence
<220> FEATURE:
<223> OTHER INFORMATION: Synthetic integrin beta 3 chain antisense
      primer sequence

<400> SEQUENCE: 74
tcccataagc atcaacaatg ag                                             22

<210> SEQ ID NO 75
<211> LENGTH: 22
<212> TYPE: DNA
<213> ORGANISM: Artificial sequence
<220> FEATURE:
```

-continued

<223> OTHER INFORMATION: Synthetic integrin beta 4 chain sense primer
      sequence

<400> SEQUENCE: 75
gcttcacacc tatttccctg tc					22

<210> SEQ ID NO 76
<211> LENGTH: 22
<212> TYPE: DNA
<213> ORGANISM: Artificial sequence
<220> FEATURE:
<223> OTHER INFORMATION: Synthetic integrin beta 4 chain antisense
      primer sequence

<400> SEQUENCE: 76
gaaggaaggt ttcagatgga tg					22

<210> SEQ ID NO 77
<211> LENGTH: 22
<212> TYPE: DNA
<213> ORGANISM: Artificial sequence
<220> FEATURE:
<223> OTHER INFORMATION: Synthetic integrin beta 5 chain sense primer
      sequence

<400> SEQUENCE: 77
gctggtgttc acaacagatg at					22

<210> SEQ ID NO 78
<211> LENGTH: 22
<212> TYPE: DNA
<213> ORGANISM: Artificial sequence
<220> FEATURE:
<223> OTHER INFORMATION: Synthetic integrin beta 5 chain antisense
      primer sequence

<400> SEQUENCE: 78
atcccagact gacaactcca ct					22

<210> SEQ ID NO 79
<211> LENGTH: 22
<212> TYPE: DNA
<213> ORGANISM: Artificial sequence
<220> FEATURE:
<223> OTHER INFORMATION: Synthetic integrin beta 6 chain sense primer
      sequence

<400> SEQUENCE: 79
tgtgactgtg gtgaatgtgt gt					22

<210> SEQ ID NO 80
<211> LENGTH: 22
<212> TYPE: DNA
<213> ORGANISM: Artificial sequence
<220> FEATURE:
<223> OTHER INFORMATION: Synthetic integrin beta 6 chain antisense
      primer sequence

<400> SEQUENCE: 80
caccagctag tttgcacttg tc					22

<210> SEQ ID NO 81
<211> LENGTH: 22
<212> TYPE: DNA
<213> ORGANISM: Artificial sequence
<220> FEATURE:

```
<223> OTHER INFORMATION: Synthetic integrin beta 7 chain sense primer
      sequence

<400> SEQUENCE: 81
cacttcagac gacacattcc at                                              22

<210> SEQ ID NO 82
<211> LENGTH: 22
<212> TYPE: DNA
<213> ORGANISM: Artificial sequence
<220> FEATURE:
<223> OTHER INFORMATION: Synthetic integrin beta 7 chain antisense
      primer sequence

<400> SEQUENCE: 82
cccaactgca gacttaggaa tc                                              22

<210> SEQ ID NO 83
<211> LENGTH: 22
<212> TYPE: DNA
<213> ORGANISM: Artificial sequence
<220> FEATURE:
<223> OTHER INFORMATION: Synthetic integrin beta 8 chain sense primer
      sequence

<400> SEQUENCE: 83
gcattatgtc gaccaaactt ca                                              22

<210> SEQ ID NO 84
<211> LENGTH: 22
<212> TYPE: DNA
<213> ORGANISM: Artificial sequence
<220> FEATURE:
<223> OTHER INFORMATION: Synthetic integrin beta 8 chain antisense
      primer sequence

<400> SEQUENCE: 84
atttcttcag gcttctcacg tc                                              22

<210> SEQ ID NO 85
<211> LENGTH: 20
<212> TYPE: DNA
<213> ORGANISM: Artificial sequence
<220> FEATURE:
<223> OTHER INFORMATION: Synthetic GAPDH-F primer

<400> SEQUENCE: 85
gagtcaacgg atttggtcgt                                                 20

<210> SEQ ID NO 86
<211> LENGTH: 20
<212> TYPE: DNA
<213> ORGANISM: Artificial sequence
<220> FEATURE:
<223> OTHER INFORMATION: Synthetic GADPH-R primer

<400> SEQUENCE: 86
ttgattttgg agggatctcg                                                 20
```

APPLICATION OF LAMININ TO CORNEAL ENDOTHELIAL CELL CULTURE

CROSS-REFERENCE TO RELATED APPLICATIONS

This patent application is the U.S. national phase of International Patent Application No. PCT/JP2014/081917, filed Nov. 26, 2014, which claims the benefit of Japanese Patent Application No. 2013-244972, filed on Nov. 27, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 136,801 bytes ASCII (Text) file named "724340Sequence-Listing.txt," created May 23, 2016.

DETAILED DESCRIPTION OF INVENTION

Technical Field

The present invention relates to use of laminin as a component for culturing or growing corneal endothelial cells culture. Specifically, the present invention is related to a composition, container, culturing method and the like for culturing or growing of corneal endothelial cells comprising laminin.

Background Art

Human corneal endothelial cells are present at a density of about 3000 cells per square millimeter at birth. However, once impaired, human corneal endothelial cells do not have an ability to regenerate. As such, corneal endothelial cells are deemed difficult to culture. Due to the current state where it is difficult to culture or grow corneal endothelial cells in transplant techniques, a treatment or surgery on a corneal endothelium is practically impossible. There is a shortage of donation of corneas in Japan, where approximately 1700 cases of corneal transplants are annually performed domestically in comparison to about 2600 patients awaiting a corneal transplant.

CITATION LIST

Patent Literature

[PTL 1] Japanese Laid-Open Publication No. 2011-78370
[PTL 2] WO 2013/047763
[PTL 3] WO 2011/024070
[PTL 4] WO 2010/140464

Non-Patent Literature

[NPTL 1] Journal of the Medical Society of Toho University Vol. 56, No. 1, Page. 39 (Jan. 1, 2009)
[NPTL 2] Nippon Ganka Gakkai Zasshi [Journal of Japanese Ophthalmological Society] Vol. 105, extra edition, Page. 196 (Mar. 15, 2001)
[NPTL 3] J Biol Chem. Sep. 13, 2013. [Epub ahead of print]
[NPTL 4] PLoS One. 2013; 8(1):e53648. doi: 10.1371/journal.pone.0053648. Epub Jan. 7, 2013
[NPTL 5] Cell Adh Migr. January-February 2013; 7(1):142-9. doi: 10.4161/cam.22125. Epub Oct. 17, 2012
[NPTL 6] J Cell Biochem. Feb. 15, 2007; 100(3):545-56.

SUMMARY OF INVENTION

Solution to Problem

The inventors of the present application have consummated the present invention by discovering that a specific laminin is useful in culturing and growing corneal endotheliums. Thus, the present invention provides the following representative items:

(1) A composition for culturing or growing corneal endothelial cells, comprising at least one agent consisting of laminins and fragments thereof which express in corneal endothelial cells.

(2) The composition according to item 1, wherein the laminins comprise laminin 511 (alpha5 beta1 gamma1) and laminin 512 (alpha5 beta2 gamma 1).

(3) The composition according to item 1 or 2, wherein the fragments has cell adhesion capability of corneal endothelial cells.

(4) The composition according to any one of items 1-3, wherein the agent is laminin 511, laminin 521 or laminin 511-E8 fragment.

(5) The composition according to any one of items 1-4, wherein the corneal endothelial cells are from human.

(6) A medium for culturing corneal endothelial cells, comprising the composition according to any one of items 1-5.

(7) A culture container for corneal endothelial cells, which is coated with the composition according to item 1.

(8) A method for culturing corneal endothelial cells comprising the step of using the composition according to any one of items 1-5.

(9) A method for culturing corneal endothelial cells comprising the step of using the medium according to item 6.

(10) A method for culturing corneal endothelial cells comprising the step of using the container according to item 7.

It is understood that the above mentioned feature(s) may be used in combination. Further embodiments and advantages of the present invention will be appreciated by the skilled in the art upon reading and understanding the detailed description of the invention as provided below as necessary.

Advantageous Effects of Invention

The present invention provides a component that enables culture, maintenance, and growth of corneal endothelial cells (in particular, human corneal endothelial cells).

BRIEF DESCRIPTION OF DRAWINGS

FIG. 3A-FIG. 3C collectively show the expression analysis of various integrin chains in human corneal endothelial cells by flow cytometry. FIG. 3A shows the expression analysis of various integrin chains in human corneal endothelial cells by flow cytometry. The top row, from the left, shows integrin α1, α2, and α3. The bottom row, from the left, shows integrin α4, α5, and α6.

FIG. 3B also shows the expression analysis of various integrin chains in human corneal endothelial cells by flow cytometry. The top row, from the left, shows integrin αE, αV, and αL. The bottom row, from the left, shows integrin αM, αX, and αIIb (CD41a).

FIG. 3C also shows the expression analysis of various integrin chains in human corneal endothelial cells by flow cytometry. The top row, from the left, shows integrin αIIb (CD41b), β1, and β2. The bottom row, from the left, shows integrin β3, β4, and β7.

FIG. 4 is a picture showing that laminin 511 and laminin 521 promote cell adhesion of human corneal endothelial cells. The top row, from the left, shows laminin 511, laminin 521, and laminin 211. The bottom row, from the left, shows no coating, FNC coating, and gelatin coating. The scale is 50 μm.

FIG. 8 is a picture from a phase-contrast microscope on day 2 of culture, showing that laminin 511 and laminin 521 enhance the efficiency of culturing human corneal endothelial cells. The top left shows laminin 511, top right shows laminin 521, bottom left shows laminin 211, and bottom right shows no coating. The bar indicates 100 μm.

FIG. 10 is a picture showing that laminin 511 and laminin 521 enable culturing human corneal endothelial cells at a high cellular density. The red dye indicates Na$^+$/K$^+$-ATPase and the blue dye indicates DAPI. The top left shows laminin 511, top right shows laminin 521, bottom left shows laminin 211, and bottom right shows no coating. The bar indicates 100 μm.

DESCRIPTION OF EMBODIMENTS

Figure 1:
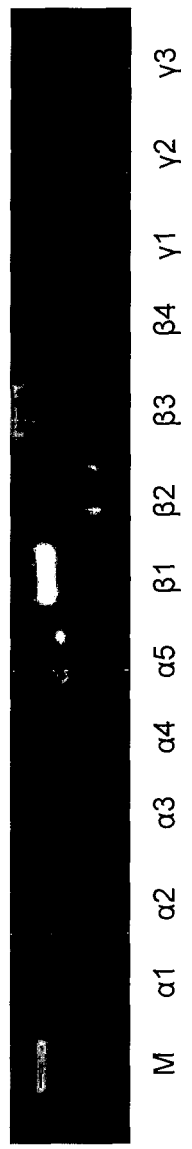
FIG. 1 is a diagram showing mRNA expression of various laminin chains in human corneal endothelial cells. The diagram, from the left, shows a molecular weight marker, a laminin α1 chain, α2 chain, α3 chain, α4 chain, α5 chain, β1 chain, β2 chain, β3 chain, β4 chain, γ1 chain, γ2 chain, and γ3 chain.

The present invention is described below. Throughout the present specification, an expression in a singular form should be understood as encompassing the plural form of the concept unless specifically stated otherwise. Thus, a singular article (e.g., "a", "an", "the" and the like in English) should be understood as encompassing the plural form of the concept unless specifically stated otherwise. Further, the terms used herein should be understood as being used in the meaning as conventionally used in the art unless specifically stated otherwise. Thus, unless defined otherwise, all the specific technical terms and scientific terminology used herein bears the same meaning as generally understood by those skilled in the art to which the present invention belongs. In a case of a contradiction, the present specification (including the definitions) takes precedence.

(Definition)

As used herein, "corneal endothelial cell" is used in the meaning as conventionally used in the art. A cornea is one of the laminar tissues constituting an eye. A cornea is transparent and is located at the closest part to the outside environment. In humans, a cornea is considered as consisting of five layers, in order from the outside (body surface), a corneal epithelium, a Bowman's membrane, a substantia propia, a Descemet's membrane (corneal endothelial basement membrane), and a corneal endothelium. In particular, unless otherwise specified, the portions other than the epithelium and the endothelium may be referred together as the "corneal stroma" and is called as such herein. As used herein, "HCEC" is an abbreviation of human corneal endothelial cells. It is understood that for corneal endothelial cells used in the present invention, naturally occurring cells, as well as cells differentiated from a stem cell, i.e., differentiation-induced cells from iPS or the like, can be used.

As used herein, "isolated" refers to a state where the amount of materials that naturally come together with the cells in a normal environment is at least reduced, and preferably a state of being substantially free of such materials. Thus, an isolated cell, tissue or the like refers to a cell that is substantially free of other materials (e.g., other cells, protein, or nucleic acid) that comes together in the cell in a natural environment.

As used herein, "corneal endothelial formulation" refers to any formulation or medicinal agent comprising a corneal endothelium or a corneal endothelium cell. Since corneal endothelial cells that are produced and cultured with a method of the present invention can be formulated, a corneal endothelial formulation/agent can be manufactured using corneal endothelial cells that are cultured and produced with a method of the present invention.

As used herein, "extracellular matrix" is also called (ECM) and refers to a material that exists between somatic cells, regardless of whether the cell is an epithelial cell or a non-epithelial cell. Since an extracellular matrix is generally produced by cells, an extracellular matrix is a biological material. An extracellular domain is involved not only in supporting tissue but also in constituting the internal environment needed for the survival of all somatic cells. An extracellular matrix is generally produced from connective tissue cells. However, some are secreted from the cells themselves that have a basement membrane, such as an epithelial cell or an endothelial cell. An extracellular matrix is roughly divided into fibrous components and a matrix that fills the space between the fibrous components. The fibrous components include collagenous fibers and elastic fibers. The basic constituent of the matrix is glucosaminoglycan (acid mucopolysaccharide), the majority of which forms a macromolecule of proteoclycans (acid mucopolysaccharide-protein complex) by binding with a non-collagenous protein. In addition, a matrix comprises laminin in the basement membrane, microfibril in the periphery of elastic fibers, fibers, and a glycoprotein such as fibronectin on the cell surface. The base structure is the same in specialized tissue. For example, in hyaline cartilage, a cartilage matrix comprising a characteristically large amount of proteoglycans is produced by a chondroblast, and in bone, a bone matrix where calcinosis takes place is produced by an osteoblast. In this regard, representative materials constituting an extracellular matrix include, but not limited to, collagen I, collagen III, collagen IV, collagen V, elastin, collagen VIII, vitronectin, fibronectin, laminin, thrombospondin, and proteoglycans (e.g., decorin, biglycan, fibromodulin, lumican, hyaluronic acid, aggrecan and the like). Various extracellular matrices having a role in cell adhesion can be utilized in the present invention.

As used herein, "laminin" is a protein constituting a basement membrane of an extracellular matrix. Laminin promotes multicellularity/tissue construction and maintenance thereof, cell adhesion, cell migration, and cell growth and has a close relationship with cancer cells. A laminin is considered to be expressed in the early stage (2-cell stage) of blastogenesis. Laminin is a heterotrimer consisting of each one of an α chain, a β chain and a γ chain. For the naming of a laminin, the nomenclature in the order of discovery (laminin-1, laminin-2, etc) is known. However, since correspondence to subunits is not considered, a newer naming method, in which the name of the subclasses α, β, or γ (a three digit number, the digit of the hundred indicates α, the digit of ten indicates β, and the digit of one indicates γ) is described together, is employed herein. In case of α1, β1 and γ1, such a laminin is called laminin 111. For a laminin, five types of α chains, 3 types of β chains, and three types of γ chains have been discovered. Thus, the theoretic maximum number of combinations is 5×3×3=45, and 45 types of laminin molecules are possible. However, it is believed that not all of the combinations exist in nature. Each subunit is called LAMA1, LAMA2, LAMA3, LAMA4, or LAMA5 for an α chain, LAMB1, LAMB2, or LAMB5 for a β chain, and LAMC1, LAMC2, or LAMC3 for a γ chain. Laminin proteins used in the present invention may be those in a natural form or those in a modified form where one or more amino acid residues are modified while retaining the biological activity, especially the cell adhesion promoting activity. Further, the laminin proteins in the present invention are not limited in the origin, production method thereof or the like, as long as the laminin protein has the features described herein. Thus, the laminin proteins used in the present invention may be of any naturally occurring proteins, proteins expressed from a recombinant DNA by a genetic engineering method, or chemically synthesized proteins. The origin of the laminin proteins used in the present invention is not particularly limited, but is preferably derived from a human. When culturing a human cell for the purpose of obtaining a medical material, it is preferable, but is not limited to, using a laminin derived from a human in order to avoid the use of a material derived from another animal.

Binding molecules of a laminin are known. α1β1, α2β1, α2β2, α3β1, α6β1, α6β4, α7β1, α9β1, αvβ3, αvβ5, αvβ8 are integrins known as laminin receptor.

The following Table describes representative laminins and the explanation therefor.

| trimer composition (name) | main expression site | integrin binding specificity |
|---|---|---|
| α1β1γ1(laminin-1) | Fetal tissue | α5β1 |
| α1β2γ1(laminin-3) | | |
| α2β1γ1(laminin-2) | Muscles, nerves | α7β1, α5β1, α3β1 |
| α2β2γ1(laminin-4) | (Schwann cell) | |
| α2β1γ3(laminin-12) | | |
| α3β3γ2(laminin-5) | Skin, lung, and other epithelial tissue | α3β1, α5β4 |
| α3β1γ1(laminin-6) | | |
| α3β2γ1(laminin-7) | | |
| α4β1γ1(laminin-8) | Blood vessel | α5β1, α3β1 |
| α4β2γ1(laminin-9) | | |
| α5β1γ1(laminin-10) | Blood vessel, liver, lung, and other epithelial tissue | α3β1, α5β1 |
| α5β2γ1(laminin-11) | | |

As used herein, "α1 chain" (LAMA1) is a subunit of a laminin•protein of a cell adhesion molecule in an extracellular matrix, and is called LAMA1, LAMA, S-LAM-alpha, or the like. For human LAMA1, the sequences of the gene and protein are registered as NCBI registration numbers NM_005559 and NP_005550, respectively. OMIM is identified with an accession number 150320. When used for the purpose herein, it is understood that "α1 chain" or "LAMA1" means not only a protein having an amino acid sequence described in the specific sequence number or accession number (or a nucleic acid encoding the protein), but also a functionally active derivative, a functionally active fragment, or a homologue thereof, or a mutant encoded by a nucleic acid that hybridizes to a nucleic acid encoding a protein under high or low stringency condition.

As used herein, "α2 chain" (LAMA2) is a subunit of a laminin•protein of a cell adhesion molecule in an extracellular matrix, and is called LAMA2, LAMM, or the like. For human LAMA2, the sequences of the gene and protein are registered as NCBI registration numbers NM_000426 and NP_000417, respectively. OMIM is identified with an accession number 156225. When used for the purpose herein, it is understood that "α2 chain" or "LAMA2" means not only a protein having an amino acid sequence described in the specific sequence number or accession number (or a nucleic acid encoding the protein), but also a functionally active derivative, a functionally active fragment, or a homologue thereof, or a mutant encoded by a nucleic acid that hybridizes to a nucleic acid encoding a protein under high or low stringency condition.

As used herein, "α3 chain" (LAMA3) is a subunit of a laminin•protein of a cell adhesion molecule in an extracellular matrix, and is called LAMA3, BM600, E170, LAMNA, LOCS, lama3a, or the like. For human LAMA3, the sequences of the gene and protein are registered as NCBI registration numbers NM_000227 and NP_000218, respectively. OMIM is identified with an accession number 600805. When used for the purpose herein, it is understood that "α3 chain" or "LAMA3" means not only a protein having an amino acid sequence described in the specific sequence number or accession number (or a nucleic acid encoding the protein), but also a functionally active derivative, a functionally active fragment, or a homologue thereof, or a mutant encoded by a nucleic acid that hybridizes to a nucleic acid encoding a protein under high or low stringency condition.

As used herein, "α4 chain" (LAMA4) is a subunit of a laminin•protein of a cell adhesion molecule in an extracellular matrix, and is called LAMA4, LAMA3, LAMA4*-1, CMD1JJ or the like. For human LAMA4, the sequences of the gene and protein are registered as NCBI registration numbers NM_001105206 and NP_001098676, respectively. OMIM is identified with an accession number 600133. When used for the purpose herein, it is understood that "α4 chain" or "LAMA4" means not only a protein having an amino acid sequence described in the specific sequence number or accession number (or a nucleic acid encoding the protein), but also a functionally active derivative, a functionally active fragment, or a homologue thereof, or a mutant encoded by a nucleic acid that hybridizes to a nucleic acid encoding a protein under high or low stringency condition.

As used herein, "α5 chain" (LAMA5) is a subunit of a laminin•protein of a cell adhesion molecule in an extracellular matrix, and is called LAMA5, KIAA1907, or the like. For human LAMA5, the sequences of the gene and protein are registered as NCBI registration numbers NM_005560 and NP_005551, respectively. OMIM is identified with an accession number 601033. When used for the purpose herein, it is understood that "α5 chain" or "LAMA5" means not only a protein having an amino acid sequence described in the specific sequence number or accession number (or a nucleic acid encoding the protein), but also a functionally active, a functionally active fragment, or a homologue thereof, or a mutant encoded by a nucleic acid that hybridizes to a nucleic acid encoding a protein under high or low stringency condition.

As used herein, "β1 chain" (LAMB1) is a subunit of a laminin•protein of a cell adhesion molecule in an extracellular matrix, and is called LAMB1, CLM, LIS5, or the like. For human LAMB1, the sequences of the gene and protein are registered as NCBI registration numbers NM_002291 and NP_002282, respectively. OMIM is identified with an accession number 150240. When used for the purpose herein, it is understood that "β1 chain" or "LAMB1" means not only a protein having an amino acid sequence described in the specific sequence number or accession number (or a nucleic acid encoding the protein), but also a functionally active derivative, a functionally active fragment, or a homologue thereof, or a mutant encoded by a nucleic acid that hybridizes to a nucleic acid encoding a protein under high or low stringency condition.

As used herein, "β2 chain" (LAMB2) (laminin S) is a subunit of a laminin•protein of a cell adhesion molecule in an extracellular matrix, and is called LAMB2, LAMS, NPHS5, or the like. For human LAMB2, the sequences of the gene and protein are registered as NCBI registration numbers NM_002292 and NP_002283, respectively. OMIM is identified with an accession number 150325. When used for the purpose herein, it is understood that "β2 chain" or "LAMB2" means not only a protein having an amino acid sequence described in the specific sequence number or accession number (or a nucleic acid encoding the protein), but also a functionally active derivative, a functionally active fragment, or a homologue thereof, or a mutant encoded by a nucleic acid that hybridizes to a nucleic acid encoding a protein under high or low stringency condition.

As used herein, "β3 chain" (LAMB3) is a subunit of a laminin•protein of a cell adhesion molecule in an extracellular matrix, and is called LAMB3, BM600-125KDA, LAM5, LAMNB1, or the like. For human LAMB3, the sequences of the gene and protein are registered as NCBI registration numbers NM_000228 and NP_000219, respectively. OMIM is identified with an accession number 150310. When used for the purpose herein, it is understood that "β3 chain" or "LAMB3" means not only a protein having an amino acid sequence described in the specific sequence number or accession number (or a nucleic acid encoding the protein), but also a functionally active derivative, a functionally active fragment, a homologue thereof, or a mutant encoded by a nucleic acid that hybridizes to a nucleic acid encoding a protein under high or low stringency condition.

As used herein, "γ1 chain" (LAMC1) is a subunit of a laminin•protein of a cell adhesion molecule in an extracellular matrix, and is called LAMC1, LAMB2, or the like. For human LAMC1, the sequences of the gene and protein are registered as NCBI registration numbers NM_002293 and NP_002284, respectively. OMIM is identified with an accession number 150290. When used for the purpose herein, it is understood that "γ1 chain" or "LAMC1" means not only a protein having an amino acid sequence described in the specific sequence number or accession number (or a nucleic acid encoding the protein), but also a functionally active derivative, a functionally active fragment, a homologue thereof, or a mutant encoded by a nucleic acid that hybridizes to a nucleic acid encoding a protein under high or low stringency condition.

As used herein, "γ2 chain" (LAMC2) is a subunit of a laminin•protein of a cell adhesion molecule in an extracellular matrix, and is called LAMC2, B2T, BM600, CSF, EBR2, EBR2A, LAMB2T, LAMNB2, or the like. For human LAMC2, the sequences of the gene and protein are registered as NCBI registration numbers NM_005562 and NP_005553, respectively. OMIM is identified with an accession number 150292. When used for the purpose herein, it is understood that "γ2 chain" or "LAMC2" means not only a protein having an amino acid sequence described in the specific sequence number or accession (or a nucleic acid encoding the protein), but also a functionally active derivative, a functionally active fragment, a homologue thereof, or a mutant encoded by a nucleic acid that hybridizes to a nucleic acid encoding a protein under high or low stringency condition.

As used herein, "γ3 chain" (LAMC3) is a subunit of a laminin•protein of a cell adhesion molecule in an extracellular matrix, and is called LAMC3, OCCM, or the like. For human LAMC3, the sequences of the gene and protein are registered as NCBI registration numbers NM_006059 and NP_006050, respectively. OMIM is identified with an accession number 604349. When used for the purpose herein, it is understood that "γ3 chain" or "LAMC3" means not only a protein having an amino acid sequence described in the specific sequence number or accession number (or a nucleic acid encoding the protein), but also a functionally active derivative, a functionally active fragment, a homologue thereof, or a mutant encoded by a nucleic acid that hybridizes to a nucleic acid encoding a protein under high or low stringency condition.

Figure 2:
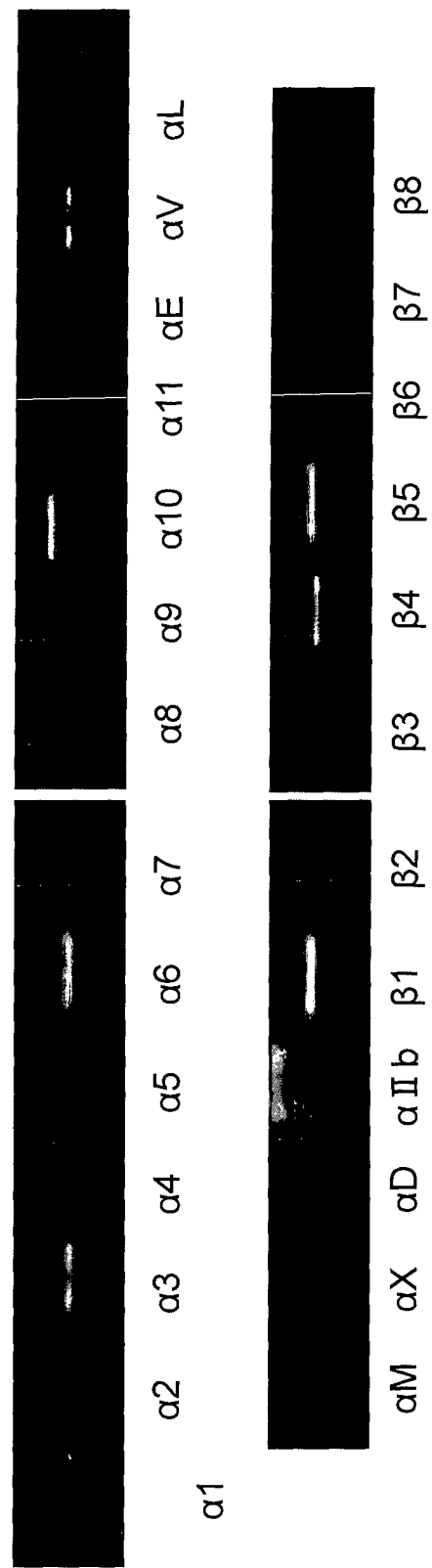
FIG. 2 shows mRNA expression of various integrin chains in human corneal endothelial cells. The top row, from the left, shows integrin α1 chain, α2 chain, α3 chain, α4 chain, α5 chain, α6 chain, α7 chain, α8 chain, α9 chain, α10 chain, α11 chain, αE chain, αV chain, and αL chain. The bottom row, from the left, shows integrin αM chain, αX chain, αD chain, αIIb chain, β1 chain, β2 chain, β3 chain, β4 chain, β5 chain, β6 chain, β7 chain, and β8 chain.

As used herein, "laminin expressed in corneal endothelial cells" refers to a type of laminin gene which is expressed in a normal state, or preferably significantly expressed at the protein level, in corneal endothelial cells. α5, β1, β2, and γ1 are confirmed as being expressed by the analysis herein (FIG. 2). Thus, at least laminin 511 and laminin 521 are confirmed as being expressed in corneal endothelial cells. Dev. Dyn. 218, 213-234, 2000, and J. Biol. Chem. 277(15), 12741-12748, 2002 have detailed description for laminin 511. Thus, the content disclosed in these documents is incorporated by reference. For laminin 511 or the like, it is possible to utilize those that are commercially available. For example, recombinant proteins of laminin 511 and laminin 521 are commercially available and obtainable from Bio-Lamina AB.

As used herein, "expression" of a gene, polynucleotide, polypeptide or the like refers to the gene or the like being subjected to a certain effect in vivo to be in another form. Preferably, the term refers to a gene, polynucleotide or the like being transcribed and translated to be in a form of a polypeptide. However, the gene, polynucleotide or the like being transcribed to result in mRNA can be one form of expression. Still preferably, such a polypeptide form can be those receiving processing after translation (referred to as a derivative herein). For example, the expression level of each laminin chain can be determined by any method. Specifically, the expression level of each laminin chain can be found by evaluating the amount of mRNA of each laminin chain, amount of protein of each laminin chain and biological activity of the protein of each laminin chain. The amount of mRNA or protein of each laminin chain can be determined by a method as described herein.

As used herein, "functional equivalent" refers to anything that has the same target function but a different structure with respect to the original subject entity. Thus, it is understood that when referring to a "group consisting of a laminin or each laminin chain, or a functional equivalent thereof" or a "group consisting of a laminin, each laminin chain, and a functional equivalent thereof", the following is encompassed therein: a laminin or each laminin chain itself, as well as fragments, mutants or variants of the laminin or each laminin chain (e.g., amino acid sequence variant or the like) having one or more capabilities of cellular adhesion, differentiation regulation and/or growth promoting action on an eye cell or the like; and substances that can change into a laminin or each laminin chain itself, or a fragment, mutant or variant of the laminin or each laminin chain at the time of action (including, for example, a nucleic acid encoding a laminin or each laminin chain itself, or a fragment, mutant or variant of laminin or each laminin chain and a vector, cell or the like comprising such a nucleic acid). A representative example of the "group consisting of a laminin or each laminin chain, or a functional equivalent thereof" or "group consisting of a laminin, each laminin chain, and a functional equivalent thereof" includes at least one agent selected from the group consisting of lamini and fragments thereof. In the present invention, it is understood that a functional equivalent of a laminin or each laminin chain can be used similarly to a laminin or each laminin chain without any specific mention thereof.

As used herein, "fragment" refers to a polypeptide or polynucleotide with a sequence length of 1 to n−1 with respect to the entire length of a polypeptide or polynucleotide (length n). The length of a fragment can be appropriately changed in accordance with the objective. For example, for a polypeptide, the lower limit of the length thereof includes 3, 4, 5, 6, 7, 8, 9, 10, 15, 20, 25, 30, 40, 50 and more amino acids. In addition, lengths represented by an integer that is not specifically listed herein (e.g. 11 and the like) can also be appropriate as the lower limit. Further, for a polynucleotide, the lower limit of the length thereof includes 5, 6, 7, 8, 9, 10, 15, 20, 25, 30, 40, 50, 75, 100 and more nucleotides. In addition, lengths represented by an integer that is not specifically listed herein (e.g. 11 and the like) can also be appropriate as the lower limit. It is understood herein that fragments themselves of such a laminin chain, when functioning as a factor of activity, e.g., growth promotion or maintenance, are within the scope of the present invention. According to the present invention, as used herein, the term "activity" refers to a function of a molecule in the broadest meaning. Activity generally encompasses, but is not intended to be limited to, biological function, biochemical function, physical function, or chemical function of a molecule. Activity encompasses, for example, enzymatic activity, ability to interact with another molecule and ability to activate, promote, stabilize, inhibit, suppress, or destabilize a function of another molecule, stability, and ability to localize at a specific position in a cell. When applicable, the term is directed to a function of a protein complex in the broadest meaning. As used herein, "biological function", when a reference is made to a gene or a nucleic acid or polypeptide related thereto, refers to a specific function that the gene, nucleic acid or polypeptide can have in a living organism. "Biological function" includes, but is not limited to, creation of a specific antibody, enzymatic activity, giving resistance and the like. As used herein, biological function can be exerted by "biological activity". As used herein "biological activity" refers to activity that a factor (e.g., polynucleotide and protein) can have in a living organism, and activity exerting a variety of functions (e.g., transcription promoting activity) is encompassed therein. For example, activity of activating or deactivating a molecule from interaction with another molecule is also encompassed. When two factors interact, the biological activity thereof can be thought of as the binding of the two molecules and the biological change resulting therefrom, e.g., in a case when two molecules are bound, e.g., the two molecules are bound if they co-precipitate when using an antibody against either one of the molecules. Thus, a method of determination includes observing such co-precipitation. For example, when a factor is an enzyme, the biological activity thereof encompasses the enzymatic activity thereof. In another example, when a factor is a ligand, the binding to a receptor to which the ligand matches is encompassed. Such biological activity can be measured by a well-known technique in the art. Thus, "activity" refers to various measurable indicators that indicate or reveal the binding (either directly or indirectly) or an elicited response (i.e., having a measurable effect in response to some exposure or stimulation). For example, "activity" includes a compound that binds to a polypeptide or polynucleotide of the present invention, the amount of proteins affected upstream or downstream after some exposure or stimulation, or a measure of another analogous function.

"Functionally active" as used herein refers to a polypeptide, a fragment or a derivative, having biochemical function, regulation function, or structural function of a protein such as biological activity in accordance with the embodiment associated with the polypeptide, a fragment or derivative, of the present invention.

As used herein, a "fragment" of a laminin refers to any fragment of a laminin. As an agent used in the present invention, it is understood that not only the entire length of a laminin, but also a fragment of the laminin can be used as long as the fragment has the function of the entire length of the laminin, particularly the cell adhesion capability of an endothelial cell. Thus, a fragment of a laminin used in the present invention generally has at least one feature of the laminin. Such a feature can encompass cell adhesion capability of an endothelial cell in particular.

The sequence of a laminin found to be expressed in corneal endothelial cells in the present invention will be described below. It is understood that these laminins indicate preferred representative examples of the present invention and the present invention is not limited to these specific laminin subtypes.

A representative nucleotide sequence of a laminin α5 chain can be (a) a polynucleotide having the base sequence described in SEQ ID NO: 1 or a fragment sequence thereof;

(b) a polynucleotide encoding a polypeptide consisting of the amino acid sequence described in SEQ ID NO: 2 or a fragment thereof;

(c) a polynucleotide encoding a variant polypeptide or a fragment thereof in which one or more amino acids have a mutation selected from the group consisting of substitution, addition and deletion in the amino acid sequence described in SEQ ID NO: 2, wherein the variant polypeptide has biological activity;

(d) a polynucleotide which is an allele or a splice mutant of the base sequence described in SEQ ID NO: 1 or a fragment thereof;

(e) a polynucleotide encoding a species homolog of a polypeptide consisting of the amino acid sequence described in SEQ ID NO: 2 or a fragment thereof;

(f) a polynucleotide which hybridizes with a polynucleotide of one of (a)-(e) under a stringent condition and encodes a polypeptide having biological activity; or (g) a polynucleotide consisting of a base sequence with identity of at least 70%, 80%, 90%, 95%, 96%, 97%, 98%, or 99% to a polynucleotide of one of (a) to (e) or a complementary sequence thereof and encodes a polypeptide having biological activity. In this regard, biological activity typically refers to activity of a laminin α5 chain. Doi M et al., J. Biol. Chem. 277(15), 12741-12748, 2002 and U.S. Pat. No. 6,933,273 can be referenced for α5 chains.

An amino acid sequence of a laminin α5 chain can be (a) a polypeptide consisting of the amino acid sequence described in SEQ ID NO: 2 or a fragment thereof;

(b) a polypeptide having biological activity and one or more amino acids with a mutation selected from the group consisting of substitution, addition and deletion in the amino acid sequence described in SEQ ID NO: 2;

(c) a polypeptide encoded by an allele or a splice mutant of the base sequence described in SEQ ID NO: 1;

(d) a polypeptide which is a species homolog of the amino acid sequence described in SEQ ID NO: 2; or (e) a polypeptide having an amino acid sequence with identity of at least 70%, 80%, 90%, 95%, 96%, 97%, 98%, or 99% to a polypeptide of one of (a) to (d). In this regard, biological activity typically refers to the activity of a laminin α5 chain. Doi M et al., J. Biol. Chem. 277(15), 12741-12748, 2002 and U.S. Pat. No. 6,933,273 can be referenced for α5 chains.

A representative nucleotide sequence of a laminin β1 chain can be (a) a polynucleotide having the base sequence described in SEQ ID NO: 3 or a fragment sequence thereof;

(b) a polynucleotide encoding a polypeptide consisting of the amino acid sequence described in SEQ ID NO: 4 or a fragment thereof;

(c) a polynucleotide encoding a variant polypeptide or a fragment thereof in which one or more amino acids have a mutation selected from the group consisting of substitution, addition and deletion in the amino acid sequence described in SEQ ID NO: 4, wherein the variant polypeptide has biological activity;

(d) a polynucleotide which is an allele or a splice mutant of the base sequence described in SEQ ID NO: 3 or a fragment thereof;

(e) a polynucleotide encoding a species homolog of a polypeptide consisting of the amino acid sequence described in SEQ ID NO: 4 or a fragment thereof;

(f) a polynucleotide which hybridizes with a polynucleotide of one of (a)-(e) under a stringent condition and encodes a polypeptide having biological activity; or (g) a polynucleotide consisting of a base sequence with identity of at least 70%, 80%, 90%, 95%, 96%, 97%, 98%, or 99% to a polynucleotide of one of (a) to (e) or a complementary sequence thereof and encodes a polypeptide having biological activity. In this regard, biological activity typically refers to activity of a laminin β1 chain. Pillarainen et al., J. Biol. Chem. 262(22), 10454-10462, 1987 and U.S. Pat. No. 6,933,273 can be referenced for β1 chains.

An amino acid sequence of a laminin β1 chain can be (a) a polypeptide consisting of the amino acid sequence described in SEQ ID NO: 4 or a fragment thereof;

(b) a polypeptide having biological activity and one or more amino acids with a mutation selected from the group consisting of substitution, addition and deletion in the amino acid sequence described in SEQ ID NO: 4;

(c) a polypeptide encoded by an allele or a splice mutant of the base sequence described in SEQ ID NO: 3;

(d) a polypeptide which is a species homolog of the amino acid sequence described in SEQ ID NO: 4; or (e) a polypeptide having an amino acid sequence with identity of at least 70%, 80%, 90%, 95%, 96%, 97%, 98%, or 99% to a polypeptide of one of (a) to (d). Pillarainen et al., J. Biol. Chem. 262(22), 10454-10462, 1987 and U.S. Pat. No. 6,933,273 can be referenced for β1 chains.

A representative nucleotide sequence of a laminin β2 chain can be (a) a polynucleotide having the base sequence described in SEQ ID NO: 5 or a fragment sequence thereof;

(b) a polynucleotide encoding a polypeptide consisting of the amino acid sequence described in SEQ ID NO: 6 or a fragment thereof;

(c) a polynucleotide encoding a variant polypeptide or a fragment thereof in which one or more amino acids have a mutation selected from the group consisting of substitution, addition and deletion in the amino acid sequence described in SEQ ID NO: 6, wherein the variant polypeptide has biological activity;

(d) a polynucleotide which is an allele or a splice mutant of the base sequence described in SEQ ID NO: 5 or a fragment thereof;

(e) a polynucleotide encoding a species homolog of a polypeptide consisting of the amino acid sequence described in SEQ ID NO: 6 or a fragment thereof;

(f) a polynucleotide which hybridizes with a polynucleotide of one of (a)-(e) under a stringent condition and encodes a polypeptide having biological activity; or (g) a polynucleotide consisting of a base sequence with identity of at least 70%, 80%, 90%, 95%, 96%, 97%, 98%, or 99% to a polynucleotide of one of (a) to (e) or a complementary sequence thereof and encodes a polypeptide having biological activity. In this regard, biological activity typically refers to the activity of a laminin β2 chain. Wewer U M et al., Genomics. Nov. 15, 1994; 24(2):243-52., 1987 and U.S. Pat. No. 6,933,273 can be referenced for β2 chains.

An amino acid sequence of a laminin β2 chain can be (a) a polypeptide consisting of the amino acid sequence described in SEQ ID NO: 6 or a fragment thereof;

(b) a polypeptide having biological activity and one or more amino acids with a mutation selected from the group consisting of substitution, addition and deletion in the amino acid sequence described in SEQ ID NO: 6;

(c) a polypeptide encoded by an allele or a splice mutant of the base sequence described in SEQ ID NO: 5;

(d) a polypeptide which is a species homolog of the amino acid sequence described in SEQ ID NO: 6; or (e) a polypeptide having an amino acid sequence with identity of at least 70%, 80%, 90%, 95%, 96%, 97%, 98%, or 99% to a polypeptide of one of (a) to (d). In this regard, biological activity typically refers to the activity of a laminin β2 chain. Wewer U M et al., Genomics. Nov. 15, 1994; 24(2):243-52, 1987 and U.S. Pat. No. 6,933,273 can be referenced for α5 chains.

A representative nucleotide sequence of a laminin γ1 chain can be (a) a polynucleotide having the base sequence described in SEQ ID NO: 7 or a fragment sequence thereof;

(b) a polynucleotide encoding a polypeptide consisting of the amino acid sequence described in SEQ ID NO: 8 or a fragment thereof;

(c) a polynucleotide encoding a variant polypeptide or a fragment thereof in which one or more amino acids have a mutation selected from the group consisting of substitution, addition and deletion in the amino acid sequence described in SEQ ID NO: 8, wherein the variant polypeptide has biological activity;

(d) a polynucleotide which is an allele or a splice mutant of the base sequence described in SEQ ID NO: 7 or a fragment thereof;

(e) a polynucleotide encoding a species homolog of a polypeptide consisting of the amino acid sequence described in SEQ ID NO: 8 or a fragment thereof;

(f) a polynucleotide which hybridizes with a polynucleotide of one of (a)-(e) under a stringent condition and encodes a polypeptide having biological activity; or (g) a polynucleotide consisting of a base sequence with identity of at least 70%, 80%, 90%, 95%, 96%, 97%, 98%, or 99% to a polynucleotide of one of (a) to (e) or a complementary sequence thereof and encodes a polypeptide having biological activity. In this regard, biological activity typically refers to activity of a laminin γ1 chain. Pillarainen et al., J. Biol. Chem. 263(14), 6751-6758, 1988 and U.S. Pat. No. 6,933,273 can be referenced for γ1 chains.

An amino acid sequence of a laminin γ1 chain can be (a) a polypeptide consisting of the amino acid sequence described in SEQ ID NO: 8 or a fragment thereof;

(b) a polypeptide having biological activity and one or more amino acids with a mutation selected from the group consisting of substitution, addition and deletion in the amino acid sequence described in SEQ ID NO: 8;

(c) a polypeptide encoded by an allele or a splice mutant of the base sequence described in SEQ ID NO: 7;

(d) a polypeptide which is a species homolog of the amino acid sequence described in SEQ ID NO: 8; or (e) a polypeptide having an amino acid sequence with identity of at least 70%, 80%, 90%, 95%, 96%, 97%, 98%, or 99% to a polypeptide of one of (a) to (d). In this regard, biological activity typically refers to the activity of a laminin γ1 chain. Pillarainen et al., J. Biol. Chem. 263(14), 6751-6758, 1988 and U.S. Pat. No. 6,933,273 can be referenced for γ1 chains.

As used herein, "protein", "polypeptide", "oligopeptide" and "peptide" are interchangeably used with the same meaning, and they refer to a polymer of an amino acid sequence of any length. This polymer may be a linear chain or a branched chain, or a cyclic chain. Amino acids may be natural or non-natural, or may be altered amino acids. This term may also encompass those assembled into a complex of a plurality of polypeptide chains. This term also encompasses naturally or artificially-altered amino acid polymer. Such alteration encompasses, for example, disulfide bond formation, glycosylation, lipidation, acetylation, phosphorylation or any other operation or alteration (e.g., conjugation with a labelled component). This definition also encompasses, for example, polypeptide comprising one or more analogs of amino acids (e.g., including non-natural amino acid), peptide-like compounds (e.g., peptoid) and other alteration publicly known in the subject field. With regard to the protein of the present invention (e.g., each chain of laminin), a DNA encoding each targeted chain gene is incorporated into an appropriate vector, which is introduced into an eukaryote or prokaryotic cell using an expression vector which can express in either host, and a respective chain is allowed to be expressed, thus obtaining a desired protein. Host cells that can be used to express laminin include, without particular limitation, prokaryotic host cells such as *E. coli* and *Bacillus subtilis*, and eukaryotic host cells such as yeast, fungus, insect cell, plant and plant cell, and mammalian cell. Vectors constructed to express a targeted laminin chain or the like can be introduced into the above-mentioned host cell, using transformation, transfection, conjugation, protoplast fusion, electroporation, particle gun technique, calcium phosphate precipitation, *Agrobacterium* method, direct microinjection or the like. Cells comprising vectors are grown in an appropriate culture medium to produce laminin chains used in the present invention, and the laminin chains are purified from the cells or culture medium, thus obtaining laminin chains or the like. The purification can be performed using size exclusion chromatography, HPLC, ion exchange chromatography, immunoaffinity chromatography or the like.

As used herein, "amino acid" may be natural or non-natural as long as the objective of the present invention is fulfilled.

As used herein, "polynucleotide", "oligonucleotide" and "nucleic acid" are interchangeably used with the same meaning, and they refer to polymer of nucleotide of any length. These terms also include "oligonucleotide derivative" or "polynucleotide derivative". The "oligonucleotide derivative" or "polynucleotide derivative" refers to oligonucleotide or polynucleotide which includes a derivative of nucleotide or in which the bonding between nucleotides is different from the normal bonding, and they are used interchangeably. As for such oligonucleotide, the following are specifically exemplified: 2'-O-methyl-ribonucleotide; an oligonucleotide derivative in which phosphodiester bonding in an oligonucleotide is converted into phosphorothioate bonding; an oligonucleotide derivative in which phosphodiester bonding in an oligonucleotide is converted into N3'-P5' phosphoramidate bonding; an oligonucleotide derivative in which ribose and phosphodiester bonding in an oligonucleotide are converted into peptide nucleic acid bonding; an oligonucleotide derivative in which uracil in an oligonucleotide is substituted by C-5 propynyl uracil; an oligonucleotide derivative in which uracil in an oligonucleotide is substituted by C-5 thiazole uracil; an oligonucleotide derivative in which cytosine in an oligonucleotide is substituted by C-5 propynyl cytosine; an oligonucleotide derivative in which cytosine in an oligonucleotide is substituted by phenoxazine-modified cytosine; an oligonucleotide derivative in which ribose in DNA is substituted by 2'-O-propylribose; and an oligonucleotide derivative in which ribose in an oligonucleotide is substituted by 2'-methoxyethoxy ribose. Unless indicated otherwise, specific nucleic acid sequences are intended to encompass a conservatively altered variant (e.g., degenerate codon substitute) and a complementary sequence thereof, as similar to explicitly indicated sequences. Specifically, a degenerate codon substitute can be achieved by creating a sequence in which the third position of one or more selected (or all the) codons are substituted by a mixed base and/or deoxyinosine residue (Batzer et al., Nucleic Acid Res. 19:5081(1991); Ohtsuka et al., J. Biol. Chem. 260: 2605-2608(1985); Rossolini et al., Mol. Cell. Probes 8:91-98(1994)). As used herein, "nucleic acid" is interchangeably used with gene, cDNA, mRNA, oligonucleotide, and polynucleotide. As used herein, "nucleotide" may be natural or non-natural.

As used herein, "gene" refers to an agent that defines a genetic trait. Normally, a gene is sequenced in a given order on a chromosome. A gene that defines a primary structure of protein is referred to as a structural gene, and a gene that influences the expression thereof is referred to as a regulator gene. Herein, "gene" may refer to "polynucleotide", "oligonucleotide" and "nucleic acid".

Amino acids may be referred herein by publicly known three-letter codes thereof, or one-letter codes recommended by IUPAC-IUB Biochemical Nomenclature Commission. Similarly, nucleotides may be referred by generally recognized one-letter codes. Herein, the comparison of the similarity, identity and homology of amino acid sequences and base sequences is calculated with default parameters, and with a sequence analysis tool, BLAST. Identity searches are conducted with, for example, BLAST 2.2.26 (issued on Oct. 30, 2011) of NCBI. Values of identity used herein normally refer to values aligned under default conditions using the BLAST. However, if higher values are obtained due to changes in parameters, the highest value will be defined to be the value for identity. If identity is evaluated in a plurality of regions, the highest value in the regions is defined to be the value for identity. Similarity is a numerical value in which similar amino acids are taken into consideration for calculation in addition to identity.

As used herein, "polynucleotide hybridizing under stringent conditions" refers to well-known conditions commonly used in the subject field. It is understood, with regard to laminin used in the present invention, that those encoded by "polynucleotide hybridizing under stringent conditions" with respect to nucleic acid sequences of respective specifically-disclosed laminins may also be used. With a polynucleotide selected from the polynucleotides of the present invention used as a probe, the use of a colony hybridization technique, a plaque hybridization technique or a southern blot hybridization technique allows such a polynucleotide to be obtained. Specifically, it means a polynucleotide obtained by conducting hybridization at 65° C. in the presence of NaCl of 0.7 to 1.0M using a filter to which a colony or plaque-derived DNA is immobilized, and then by washing the filter under the condition of 65° C. with a SSC (saline-sodium citrate) solution of 0.1 to 2 fold concentration (wherein the composition of the SSC solution of one fold concentration is 150 mM sodium chloride and 15 mM sodium citrate). Hybridization can be conducted according to methods described in experimental documents such as Molecular Cloning 2nd ed., Current Protocols in Molecular Biology, Supplement 1-38, DNA Cloning 1: Core Techniques, A Practical Approach, Second Edition, Oxford University Press (1995). Here, sequences comprising only an A sequence or a T sequence is preferably excluded from sequences that hybridize under stringent conditions. Therefore, the polypeptides (e.g., transthyretin) used in the present invention also encompass a polypeptide encoded by a nucleic acid molecule that hybridizes under stringent conditions to a nucleic acid molecule encoding the polypeptide specifically described in the present invention. These low stringency conditions include conducting hybridization for 18 to 20 hours at 40° C. in a buffer comprising 35% formamide, 5×SSC, 50 mM Tris-HCl (pH 7.5), 5 mM EDTA, 0.02% PVP, 0.02% BSA, 100 μg/ml denatured salmon sperm DNA, and 10% (weight/volume) dextran sulfate; washing 1 to 5 hours at 55° C. in a buffer consisting of 2×SSC, 25 mM Tris-HCl (pH 7.4), 5 m MEDTA, and 0.1% SDS; and washing for 1.5 hours at 60° C. in a buffer consisting of 2×SSC, 25 mM Tris-HCl (pH 7.4), 5 mM EDTA, and 0.1% SDS.

As for functional equivalents of the present invention, those in which one or a plurality of amino acids are inserted, substituted or deleted, or added to one or both ends in an amino acid sequence, can be used. Herein, "one or a plurality of amino acids are inserted, substituted or deleted, or added to one or both ends in an amino acid sequence" means that alteration is made by substitution or the like of a plurality of amino acids that could naturally occur, by a well-known technical method such as site-directed mutagenesis, or naturally-occurring mutation.

Altered amino acid sequences such as each chain of laminin used in the present invention can be those in which, for example, 1 to 30, preferably 1 to 20, more preferably 1 to 9, still more preferably 1 to 5, particularly preferably 1 to 2 amino acids are inserted, substituted, or deleted, or added to one or both ends thereof. The altered amino acid sequences may be preferably such amino acid sequences having one or a plurality (preferably, 1 or several, or 1, 2, 3, or 4) of conservative substitutions in an amino acid sequence of each chain or the like of laminin. Herein, "conservative substitution" means to substitute one or a plurality of amino acid residues with different chemically similar amino acid residues so that the functions of protein will not be substantially altered. For example, such cases can be mentioned when a given hydrophobic residue is substituted with another hydrophobic residue, or when a given polar residue is substituted with another polar residue having the same electric charge. Functionally similar amino acids capable of making such a substitution are publicly known in the subject field for each amino acid. Specific examples of non-polar (hydrophobic) amino acids include alanine, valine, isoleucine, leucine, proline, triptophan, phenylalanine, methionine and the like. Specific examples of polar (neutral) amino acids include glycine, serine, threonine, tyrosine, glutamine, asparagine, cysteine and the like. Specific examples of (basic) amino acids having a positive electric charge include arginine, histidine, lysine and the like. Further, specific examples of (acidic) amino acids having a negative electric charge include asparagine acid, glutamic acid and the like.

As used herein, "agent" may be, in a broad sense, any substance or any other elements (e.g., energy such as light, radioactivity, heat and electricity) as long as the substance can be exchangeably used and can achieve an intended objective. Such substances include, without limitation, for example, protein, polypeptide, oligopeptide, peptide, polynucleotide, oligonucleotide, nucleotide, nucleic acid (including, for example, DNA such as genome DNA and cDNA, RNA such as mRNA), polysaccharide, oligosaccharide, lipid, organic low molecule (e.g., hormone, ligand, messenger, organic low molecule, molecule synthesized by combinatorial chemistry, low molecule that can be used as a medicament (e.g., low molecular ligand) and the like), and complex molecules thereof. Agents specific to polynucleotide typically include, without limitation, polynucleotide having complementarity with given sequence homology to a sequence of the aforementioned polynucleotide (e.g., 70% or more sequence identity), polypeptide like a transcription factor binding to a promoter region, and the like. Agents specific to polypeptide typically include, without limitation, an antibody specifically directed to the polypeptide, or a derivative thereof or an analog thereof (e.g., single-stranded antibody), a specific ligand or receptor in a case when the polypeptide is a receptor or a ligand, a matrix thereof in a case when the polypeptide is enzyme, and the like.

As used herein, "culture" refers to growing subject cells, and in a limited sense, it refers to a state where the condition of subject cells is maintained, which would otherwise be worsened (e.g., where the number of cells will not substantially decrease). In a limited sense, the term is used to mean the same meaning as maintenance of culture or maintenance.

As used herein, "growth" refers to a state where the number of cells increases.

As used herein, "growth capability" refers to a cell's capability to grow. Unless specifically stated herein, a state of growth refers to a possibility of growth in a steady state. The "steady state" refers to a normal condition for a living organism where the homeostasis of the living organism is maintained. Such a state can be readily determined by those skilled in the art. For example, such can be confirmed through cellular density analysis, where cellular density is almost constant with no change, or expression of a cellular growth marker is recognized, or the like. As used herein, "promotion of growth" refers to a growth state of a given cell. If a target cell was not growing at the beginning, the start of even a little growth would correspond to promotion of growth. If a cell was already growing and the growth level was maintained or was increased, and preferably increased, then it would correspond to promotion of growth.

As used herein, "stem cell" refers to a cell which has both a capability to differentiate into a plurality of systems of cells (multilineage potential) and a capability to maintain multilineage potential even after cellular division (self-renewal capability). Stem cells include embryonic stem cell, germ cell, iPS cell, tissue stem cell and the like. The corneal endothelial cell aimed by the present invention may be such cells that are differentiated from stem cells. The differentiation from stem cells to corneal endothelial cells can be achieved using methods publicly known in the subject field.

As used herein, "normal cellular function" of cell refers to a function which a cell originally possesses when a specific cell such as corneal endothelial cells is referred. With regard to the corneal endothelial cell, such a function includes, without limitation, ZO-1 and Na$^+$/K$^+$-ATPase, adaptive capability to corneal transplant (Matsubara M, Tanishima T: Wound-healing of the corneal endothelium in the monkey: a morphometric study, J pn J Ophthalmol 1982, 26:264-273; Matsubara M, Tanishima T: Wound-healing of corneal endothelium in monkey: an autoradiographic study, Jpn J Ophthalmol 1983, 27:444-450; Van Horn D L, Hyndiuk R A: Endothelial wound repair in primate cornea, Exp Eye Res 1975, 21:113-124 and Van Horn D L, Sendele D D, Seideman S, Buco P J: Regenerative capability of the corneal endothelium in rabbit and cat, Invest Ophthalmol Vis Sci 1977, 16:597-613), and the like.

ZO-1 and Na$^+$/K$^+$-ATPase can be evaluated by observing the expression of proteins by immunological means or at an mRNA level such as RT-PCR. Confirmation of Na$^+$/K$^+$-ATPase and ZO-1 expression and/or function at the same level as normal cells allows for confirmation as to whether or not subject cells have a normal function.

As to adaptive capability to corneal transplant, implantation tests of cultured cells can be conducted by mechanically curetting corneal endothelium as a bullous keratopathy model with experimental animals such as rabbits. However, since corneal endothelial cells of rabbits grow in vivo, it is not possible to deny the possibility of natural healing due to growth of corneal endothelial cells of hosts (Matsubara M, et al., Jpn J Ophthalmol 1982, 26:264-273; Matsubara M, et al., Jpn J Ophthalmol 1983, 27:444-450; Van Horn D L, et al., Exp Eye Res 1975, 21:113-124 and Van Horn D L, et al., Invest Ophthalmol Vis Sci 1977, 16:597-613). Therefore, in order to evaluate more accurate transplant adaptive capability, it is preferable to evaluate engraftment to primates. When transplant adaptive capability to humans is evaluated, adaptivity is evaluated in primates, such as crab-eating monkeys, after at least one month, preferably at least two months, more preferably at least three months, still more preferably at least six months, and further still more preferably at least twelve months, for example. Confirmation of transplant adaptive capability in primates such as monkeys is important in application to humans, in particular.

As used herein, "BrdU" is an abbreviation of bromodeoxyuridine. Since BrdU is incorporated as an analog of dTTP in DNA synthesis, the DNA (cell nucleus) in which BrdU is incorporated can be detected by an antibody specific to BrdU that is incorporated into DNA. Thus, BrdU is used as an index to show high growth capability/differentiation capability.

As used herein, "BrdU positive" refers to a state where a cell marker, BrdU, is expressed in a target cell.

As used herein, "cultures" refers to those produced by culturing cells such as corneal endothelium. Thus, "corneal endothelium cultures" refers to the cultures of corneal endothelium, and the term normally refers to those present in a different state from those present in vivo. The corneal endothelium cultures obtained by conventional methods were problematic in that such cultures had low growth capability and would be easily become transformed and lose functions (Peh G S, Beuerman R W, Colman A, Tan D T, Mehta J S (2011) Human corneal endothelial cell expansion for corneal endothelium transplantation: an overview. Transplantation 91: 811-819, Okumura N, Kay E, Nakahara M, Hamuro J, Kinoshita S, et al. (2013) Inhibition of TGF-β signaling enables human corneal endothelial cell expansion in vitro for use in regenerative medicine. PLoS One 8:e58000). Therefore, from the viewpoint of cultures, such a cellular density could not be achieved for those that were cultured for a particularly long period of time or those that were subcultured. Specifically, the density of corneal endothelial cells is easily decreased through culturing. Corneal endothelial density is one of the most clinically important indices for the degree of health. Thus, the culturing to high density is important from the point of regeneration medicine. Further, it is possible to increase the endothelial density in advance and then conduct administration in vivo, which can be an extremely important therapeutic agent. In that sense, it is an important fact that the cellular density that was used to decrease through a normal culturing method can now be increase. The normal level of human corneal endothelium in vivo is within the range of about 2500-3000/mm$^2$. The present invention is advantageous in that the present invention has provided a technique to bring the cellular density of the cultures to the above-mentioned level or to exceed the level.

As used herein, "medium" refers to any medium capable of culturing or growing corneal endothelial cells, and the medium can take any form, such as liquid medium (culture medium), suspension medium and solid medium, as needs arise and as appropriate. Components for the medium used for such corneal endothelial cells include, for example, DMEM (GIBCO BRL), OptiMEM (Life Technologies), serum (e.g., fetal bovine serum (FBS), human serum), proliferation factor/growth factor (e.g., b-FGF), antibiotic substance (e.g., penicillin, streptomycin, gentamicin) and the like.

As used herein, "(culture) container" refers to a container for culturing corneal endothelial cells. The type of the culture containers is not particularly limited, and any containers can be used that are sterilized to prevent contamination by bacteria and that are of any material and any shape suitable for culturing cells. Examples of such culture containers include, without limitation, culture dishes, culture flasks, culture Schales, culture plates such as 96-well, 48-well, 12-well, 6-well and 4-well, culture bottles, generally used in the subject field.

(General Techniques)

The molecular biological technique, biochemical technique, microbiological process used herein are well-known and commonly used in the subject field, which are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999) PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, and Bessatsu Jikken Igaku "Idenshi Dounyu & Hatsugen Kaiseki Jikken Hou" Yodosha Co., Ltd., 1997. With regard to corneal endothelial cells, the report by Nancy Joyce et al., (Joyce, 2004 #161) (Joyce, 2003 #7) is well-known; however, as mentioned earlier, transformation of fibroblast cells is due to long-term culture or subculture. Thus, studies for effective culture methods are still continued today. Associated portions (which may be the entire portions) thereof are incorporated by reference herein.

Description of Embodiments

The description of the preferred embodiments will be described below. However, it should be understood that the embodiments are examples of the present invention and the scope of the present invention is not limited to such preferred embodiments. Further, it should be understood that those skilled in the art can readily practice modification, alteration or the like within the scope of the present invention while referring to the following preferred embodiments. Further, it should be understood that any embodiment may be combined.

(Composition and Culturing Container for Culturing or Growing Corneal Endothelial Cells)

In one aspect, the present invention provides a composition for culturing or growing corneal endothelial cells, comprising at least one agent consisting of laminins and fragments thereof which express in corneal endothelial cells.

Although an agent (laminin or the like) of the present invention can be included in a culture medium for use, the agent may be coated onto (or may cover) a culture dish for use. In order to conduct a primary culture and/or a subculture of a target cell, an appropriate medium (e.g., DMEM (Dulbecco's modified Eagle's medium) or OptiMEM) is used and the cells, which are collected and separated, are seeded for the primary culture and subculture in a culture dish for culturing. In the present invention, a good growth result can be obtained even with an amount of serum added to a medium that is 10% of less. Furthermore, in the present invention, in addition to a laminin or in addition to a coating of a laminin, a cytokine (e.g., fibroblast growth factor (FGF)) can be added to a medium as an additive. An agent of the present invention is useful in an isolated cell as described in the Examples and in an endothelial cell induced from iPS or ES cells. Further, it is understood that such a agent is effective for the induction itself.

The concentration of a laminin that is used includes, for example, about 0.1 μg to about 500 μg/ml in a culture medium solution (e.g. PBS). For coating, an amount of about 0.75 μg/cm$^2$ per unit area (e.g. cm$^2$) may be used for the coating. For use in the treatment of a culture container, the amount of laminins of the present invention or fragments thereof is not particularly limited. A favorable result can be obtained when treated with a solution of laminin or fragments thereof, preferably in the amount of about 0.01 μg/ml or more, preferably about 0.01 to 10 μg/ml, still preferably about 0.01 to about 2 μg/ml. About 0.01 to 10 μg/ml or about 0.01 to about 2 μg/ml of laminin or fragments thereof corresponds to about 0.0015 to 1.5 μg/cm$^2$ or about 0.0015 to 0.3 μg/cm$^2$ as an amount of laminin or fragments thereof in a solid phase per area of a culture container.

In a preferred embodiment, the laminin includes laminin 511 and laminin 521. Thus, in the present embodiment, an agent of the present invention can be laminin 511, laminin 521 or a fragment thereof. Any fragment may be used as a fragment of laminin 511 or a fragment of laminin 521 of the present invention, as long as the fragment can be used in culturing (may be referred to as "maintaining" or "maintaining a culture" herein, but is used in the same meaning as culturing) or growing corneal endothelial cells. Such fragments include but are not limited to a laminin 511-E8 fragment and a laminin 521-fragment (respectively, sequence numbers 9, 10 (nucleic acid sequence, amino acid sequence) and sequence numbers 11, 12 (nucleic acid sequence, amino acid sequence)) (see Taniguchi Y, Ido H, Sanzen N, Hayashi M, Sato-Nishiuchi R, Futaki S, Sekiguchi K. The C-terminal region of laminin beta chains modulates the integrin binding affinities of laminins. J Biol Chem. 284:7820-7831, 2009. Available from Nippi, Incorporated). A laminin 511-E8 fragment and laminin 521 fragment are fragments obtained by elastase treatment and are comprised of a portion of a coiled-coil domain and three LG domains (LG1 to LG3) in the α chain C-terminal region of a heterotrimer. An E8 fragment is regarded as corresponding to an integrin binding site of a heterotrimer molecule in which an α chain, β chain and γ chain of a laminin assemble via a coiled-coil domain with one another. Thus, as a preferred fragment, those in which an integrin binding site is substantially retained in the entire length of a laminin can be used. It is understood that such a fragment can be made by an appropriate alteration based on information on laminin 511-E8 and laminin 521 fragments.

In this regard, an E8 fragment of human laminin α5β1γ1 (also referred to as "human laminin 511-E8" herein) means a fragment of human laminin α5β1γ1 (also referred to as "human laminin 511" herein) corresponding to an E8 fragment of murine laminin α1β1γ1 (also referred to as "murine laminin 111-E8" herein). An E8 fragment of a laminin has been identified as a fragment with strong cell adhesion activity among fragments that are obtained by digesting murine laminin α1β1γ1 (hereinafter, described as "murine laminin 111") with elastase (Edgar D., Timpl R., Thoenen H. The heparin-binding domain of laminin is responsible for its effects on neurite outgrowth and neuronal survival. EMBO J., 3:1463-1468, 1984, Goodman S L., Deutzmann R., von der Mark K. Two distinct cell-binding domains in laminin can independently promote nonneuronal cell adhesion and spreading. J. Cell Biol., 105: 589-598, 1987). For human laminin 511 and human laminin 332, the presence of a fragment corresponding to murine laminin 111-E8 is presumed upon digestion with elastase. Human laminin 511-E8 used in the present invention is not required to be an elastase digestion product of human laminin 511. Human laminin 511-E8 used in the present invention may be a fragment of human laminin 511 having similar cell adhesion activity, similar structure, and approximately the same molecular weight as murine laminin 111-E8. A method of manufacturing human laminin 511-E8 is not particularly limited. For example, such a method includes a method of allowing the digestion of the entire length of human laminin 511 by a proteolytic enzyme such as elastase to fractionate and purify a target fragment, a method of manufacturing as a recombinant protein and the like. Manufacturing as a recombinant protein is preferred from the viewpoint of quantity of manufacture, uniformity of quality, manufacturing cost and the like. Recombinant human laminin 511-E8 can be manufactured by appropriately using a known gene recombination technique. A method of manufacturing recombinant human laminin 511-E8, for example, can manufacture recombinant human laminin 511-E8 by obtaining DNA encoding the protein of each of α chain, β chain and γ chain of human laminin 511-E8, inserting each obtained DNA into an expression vector, expressing the resulting three kinds of expression vectors by cotransfecting into the appropriate host cells, and purifying the trimeric proteins by a known method (for example, see Hiroyuki Ido, et al, "The requirement of the glutamic acid residue at the third position from the carboxyl termini of the laminin γ chains in integrin binding by laminins" The Journal of Biological Chemistry, 282, 11144-11154, 2007). JP 2011-78370 can be referred to for a specific method for manufacturing. Similar fragments may be produced by using human laminin 521, which is referred to as "laminin 521-E8 fragment." It is understood that such a fragment may be produced in a similar manner as laminin 511-E8, and that such retains similar activity to that of laminin 511-E8.

In a preferred embodiment, the agent is laminin 511, laminin 521, laminin 511-E8 fragment or laminin 521-E8 fragment.

In a preferred embodiment, the corneal endothelial cells are from human.

Endothelial cells targeted by the present invention can be prepared from an exfoliated cornea by removing the corneal endothelium native to a donor cornea without harming the integrity of a Descemet's membrane and the structure and function of a stromal layer (e.g., WO 2005/038015). An exfoliated cornea can be used as human corneal endothelial culturing cells.

In another aspect, the present invention provides a culture container for corneal endothelium cells, coated with an agent or composition of the present invention.

Preparation of a covered container or a culture plate for a laminin or the like for culturing corneal endothelial cells can be carried out by referring to a known method in the art. The preparation (coating) of a culture container can be performed as follows: For example, after a laminin solution diluted with phosphate buffer to 20 μg/mL is added to a culture dish and incubated for two hours at 37° C. (5% $CO_2$), the solution can be removed and washed twice each with the phosphate buffer in a medium for use.

Thus, in another aspect, the present invention is related to a composition for solid-phasing (coating) a cell culture container for culturing a cell in corneal endothelial cells with a system comprising at least one agent selected from the group consisting of laminins expressed in corneal endothelial cells or a fragment thereof (e.g., laminin 511, laminin 521 or a fragment thereof), or an agent for solid-phasing (coating) a cell culture container. In one embodiment, a composition or an agent of the present invention is a coating composition or a coating agent. A treatment technique of solid-phasing laminins on a surface of a culture container is known in the art. Thus, those skilled in the art can use any culture container in accordance with the objective of the present invention and apply a treatment to the container to use the container in a method of the present invention.

In another aspect, the present invention is further related to a kit comprising the above-described composition oragent. A kit of the present invention may further comprise a cell culture medium, a cell culture container or the like. A cell culture container may be, for example, a precoated culture dish or a precoated culture plate. Alternatively, a cell culture container of a kit may be in a state where at least one agent selected from a group consisting of laminins expressed in corneal endothelial cells or a fragment thereof (e.g., laminin 511, laminin 521 or a fragment thereof) is in a solid-phase. A cell culture container, composition, agent, and kit of the present invention can be used in a method of culturing a mammalian cell in a system comprising at least one factor selected from a group consisting of laminins expressed in corneal endothelial cells or a fragment thereof (e.g., laminin 511, laminin 521 or a fragment thereof).

(Method of Culturing a Corneal Endothelial Cell)

In another aspect, the present invention provides a method of culturing corneal endothelial cells, which uses a composition of the present invention. That is, the present invention provides a method of culturing or growing corneal endothelial cells, comprising a step of culturing the corneal endothelial cells by using an agent (laminin, a fragment thereof or the like) of the present invention. An agent (laminin, a fragment thereof, or the like) used in a method of present invention is understood to be able to use any form described herein. Further, any culture component can be used in a method of the present invention as long as the component can be used in culturing the corneal endothelium, and a culture component of any form described herein can be exemplified.

In one embodiment, corneal endothelial cells cultured in the present invention are from primates. In a preferred embodiment, corneal endothelial cells cultured in the present invention are from a human.

In a preferred embodiment, culturing target cells by a method of the present invention is for preventing or treating a corneal endothelial disorder, and can be used particularly for producing cells, tissues or the like for a transplant.

The temperature condition upon culturing corneal endothelial cells are not particularly limited insofar as growing a corneal endothelial cells. However, for example, the temperature condition is about 25° C. to about 45° C., or preferably about 30° C. to about 40° C. considering growth efficiency, or still preferably about 37° C. A culturing method is performed in a common cell culturing incubator under humidified environment with a $CO_2$ concentration of about 5 to 10%.

Any component that can be used in culturing a corneal endothelium can be used as a culture component that may be used in the present invention. In addition, the culture component may be a medium component that has been conventionally sold and used or a component developed separately for corneal endothelium. Examples of such a medium component include but are not limited to OptiMEM, DMEM, M199, MEM and the like (they are available from INVITROGEN or the like).

The present invention is characterized in elevating activity of a variety of specific laminins or fragments thereof by using a specific polypeptide and/or peptide in a cell culturing system comprising an agent (e.g., specific laminin or a fragment thereof) of the present invention in cell culturing. The polypeptide is selected from the group consisting of blood proteins other than an extracellular matrix protein, which is serum, serum albumin, prealbumin, immunoglobulin, α-globulin, β-globulin, α1-antitrypsin (α1-AT), haptoglobin (Hp), α2-macroglobulin (α2-M), α-fetoprotein (AFP), transferrin, retinol-binding protein (RBP) or adiponectin, and gelatin, protein of the tumor necrosis factor (TNF) family, and peptone. In one embodiment of the present invention, a polypeptide and/or peptide that can be used as an additional component is, but not limited to, serum albumin, protein of the tumor necrosis factor (TNF) family or peptone, or the polypeptide and/or peptide is immunoglobulin or gelatin.

In the present invention, preferably a blood protein and still preferably a blood protein other than an extracellular matrix protein can be used with an agent (specific laminin or a fragment thereof) of the present invention. The blood protein is preferably selected from serum, serum albumin, prealbumin, immunoglobulin, α-globulin, β-globulin, α1-antitrypsin (α1-AT), haptoglobin (Hp), α2-macroglobulin (α2-M), α-fetoprotein (AFP), transferrin, retinol-binding protein (RBP) or adiponectin, which are all blood proteins other than an extracellular matrix protein. "Extracellular matrix" is a substance that fills the extracellular space. At the same time, extracellular matrix has a skeletal role (e.g., cartilage or bone of an animal), a role of a scaffold in cell adhesion (e.g., basement membrane or fibronectin), a role in retaining or providing cell growth factor or the like (e.g., cell growth factor FGF that binds to heparan sulfate) and the like. Many of the individual cells constituting a multicellular organism that are recognized as living are buried in a bed or a nest of an extracellular matrix. Major components of an extracellular matrix of a vertebrate including humans are glycoproteins such as collagen, proteoglycan, fibronectin, and laminin (partially cell adhesion molecules). "Extracellular matrix protein" means a protein constituting such an extracellular matrix.

"Blood proteins other than an extracellular matrix protein" in the present invention means blood proteins other than an extracellular matrix protein involved in cell adhesion or the like. They are all known proteins that those skilled in the art can appropriately obtain. Blood proteins other than an extracellular matrix protein are preferably but not limited to human serum albumin (HSA/e.g. available from Nacalai Tesque), recombinant human serum albumin (rHSA/e.g., available from SIGMA-AlDRICH), or bovine serum albumin (BSA/e.g., available from SIGMA-AlDRICH). Further, "blood proteins other than an extracellular matrix protein" may be immunoglobulin. Immunoglobulins, including IgG, IgA, IgM, IgD, and IgE, are well-known to those skilled in the art. For example, a human immunoglobulin (IgG/e.g., available from Oriental Yeast Col, Ltd.) can be used but is not limited thereto.

"Gelatin" referred to herein is a substance extracted by adding heat to collagen, which is the main component of connective tissue such as skin, bone, or tendon of an animal. The main component of gelatin is protein.

As an additional component, a protein of the tumor necrosis factor (TNF) family can be used herein. "Tumor Necrosis Factor, TNF)" is one type of cytokine. Narrowly defined, there are three types of TNF, i.e., TNF-α, TNF-β (lymphotoxin (LT)-α) and LT-β. "Proteins of the TNF family" includes at least 19 types of molecules such as a receptor activator NFκB ligand (RANKL), Fas ligand and CD40 ligand. Preferably, a receptor activator NFκB ligand (RANKL, sRANKL) can be used as an example of a protein of the TNF family used as an additional component used in the present invention.

In the present invention, a peptone can be utilized as an additional component. "Peptone" is a protein obtained by dissolving a protein with a proteolytic enzyme. A protein is digested by pepsin in the stomach into a peptone in vivo, and the resulting peptone is further digested into amino acid by pancreatic juice secreted by the pancreas and by intestinal juice secreted by the jejunum. Since a peptone is suitable as a nutritional source for microorganisms, it is often added to a medium. A peptone as such a nutritional source for a medium is obtained by hydrolyzing a protein into amino acid and a low molecular weight peptide. In general, a peptone obtained from a protein of milk (milk casein) undergoing enzymolysis (using protease such as pancreatin extracted from the pancreas of a swine) is commonly used. A peptone derived from a plant is preferably used but are not limited thereto. For example, a peptone is selected from the group consisting of a peptone derived from cottonseeds, a peptone derived from soy beans, a peptone derived from wheat, and a peptide derived from peas.

(Corneal Endothelial Cells and Corneal Endothelium Formulation)

The present invention provides corneal endothelial cells cultured and produced by the method according to the present invention. The present invention can be considered as having characteristics that do not exist in conventional cells in that normally cultured or grown cells are obtained even when normal culturing is conducted and also when subculturing is conducted. In addition, the most important characteristic is that the cells have corneal endothelial characteristics that are normal in their functions. Accordingly, the corneal endothelial cells that the present invention provides may be provided as a formulation, which means that the present invention provides a corneal endothelium formulation. Accordingly, the present invention provides a method for manufacturing a corneal endothelium formulation, comprising a step of culturing corneal endothelial cells using a culture solution comprising the agent or composition according to the present invention or a container on which the agent or composition according to the present invention is coated In one aspect, the corneal endothelium formulation according to the present invention contains a base material, and corneal endothelial cells layer on the base material.

The base material used in the present invention is not particularly limited as long as it may support a cultured corneal endothelial cell layer and maintain its shape in vivo for a given period of time, preferably at least three days, after transplantation. Further, the base material used in the present invention may be those having a role as a scaffold in culturing corneal endothelial cells in a test tube, or may be those having only a role to support the corneal endothelial cell layer after the culturing. Preferably, the base material used in the present invention is those having a role as a scaffold used for culturing corneal endothelial cells and directly subjected to transplantation after the completion of the culturing.

The base material used in the present invention include, for example, high-polymer material derived from natural products such as collagen, gelatin and cellulose; synthetic macromolecular material such as polystyrene, polyester, polycarbonate and poly(N-isopropyl acrylamide); biodegradable polymer material such as polylactic acid and polyglycolic acid; hydroxyapatite, amnion and the like.

The shape of the base material used in the present invention is not particularly limited as long as it supports the corneal endothelial cell layer and it is a shape suitable for transplantation. However, the shape is preferably a sheet. When the formulation according to the present invention is in a sheet shape, it can be cut and used into a size in accordance with an application site at transplantation. Further, it is also possible to roll the sheet up tightly and insert it into a wound. As a preferable specific example, a circular shape is exemplified which covers about 80% of the area of an injured corneal endothelium. In addition, it is also preferable to incise the peripheral portion of the circle so as to be closely adhered to an application site.

In a preferable embodiment, the example of the base material used in the present invention is collagen. As to collagen, the collagen sheet described in Japanese Laid-Open Publication No. 2004-24852 can be preferably used. The subject collagen sheet can be prepared from, for example, amnion in accordance with the method described in Japanese Laid-Open Publication No. 2004-24852.

Hereinafter, preparation of corneal endothelial cells layer will be described as an example of a corneal endothelium formulation.

The corneal endothelial cell layer used in the present invention preferably comprises at least one of the following characteristics. More preferably, the corneal endothelial cell layer used in the present invention comprises two or more of the following characteristics. Still more preferably, the corneal endothelial cell layer used in the present invention comprises all of the following characteristics.

(1) The cell layer has a single layer structure. This is one of the characteristics that corneal endothelial cell layers of living organisms comprise.

(2) The cellular density in the cell layer is about 1,000 to about 4,000 cells/mm$^2$. In particular, the cellular density is preferably about 2,000 to about 3,000 cells/mm$^2$ when an adult is a recipient.

(3) The planar shape of cells constituting the cell layer is substantially hexagon. This is one of the characteristics that cells constituting corneal endothelial cells layer in living organisms comprises. The formulation of the present invention is similar to corneal endothelial cell layers of living organisms, which is capable of exerting a similar function as native corneal endothelial cell layers and is also capable of exerting growth capability in vivo.

(4) The cells are regularly arranged in the cell layer. In the corneal endothelial cell layers of living organisms, cells constituting the layers are regularly arranged. Thus, normal functions and high transparency of corneal endothelial cells are considered to be maintained, and the moistening function of the cornea is appropriately exerted. Therefore, by comprising such morphological characteristics, the formulation according to the present invention is expected to exert a function similar to that of corneal endothelial cell layers in living organisms.

The manufacturing method according to the present invention comprises a step of culturing corneal endothelial cells using the agent, composition or container according to the present invention, and can be carried out by, for example, the following method.

<1> Harvesting and Culturing Corneal Endothelial Cells in a Test Tube

Corneal endothelial cells are harvested from the cornea of a recipient himself or an appropriate donor using an ordinary method. In consideration of transplantation conditions in the present invention, corneal endothelial cells derived from the same race may be prepared. For example, the Descemet's membrane and endothelial cell layer of cornea tissues are exfoliated from parenchyma of the cornea, they are transferred to a culture dish and treated with Dispase or the like. Accordingly, corneal endothelial cells will fall off the Descemet's membrane. Corneal endothelial cells remaining on the Descemet's membrane can be fallen off by pipetting or the like. After the removal of the Descemet's membrane, the corneal endothelial cells are cultured in a culture solution according to the present invention. As for the culture or culture solution, for example, the following can be used: FBS (fetal bovine serum) (e.g., BIOWEST, catalogue number: S1820-500), b-FGF (basic fibroblast growth factor) (e.g., INVITROGEN, catalogue number: 13256-029), and an antibiotic substance, such as penicillin and streptomycin, may be appropriately added to commercially available DMEM (Dulbecco's Modified Eagle's Medium) (e.g., INVITROGEN, catalogue number: 12320 or the like), followed by adding components of a culture normalizer according to the present invention. By coating the agent according to the present invention to conduct culturing, the adhesion is promoted for corneal endothelial cells to the surface of a culture container, thereby conducting favorable growth. In addition, when culturing is conducted by adding laminin to the culture solution, it is preferable to use a culture dish, surface of which is coated with type I collagen, type IV collagen, fibronectin, laminin or extracellular matrix of bovine corneal endothelial cells or the like. Alternatively, it is possible to use an ordinary culture container which is treated with a commercially available coating agent such as FNC Coating Mix® (50 ml (AES-0407), ATHENA, catalogue number: 0407). The temperature conditions for culturing corneal endothelial cells are not particularly limited as long as corneal endothelial cells grow. For example, the temperature is within the range of about 25° C. to about 45° C., and when the growth efficiency is taken into consideration, it is preferably about 30° C. to about 40° C., and still preferably about 37° C. The culturing method is conducted in such an environment of about 5 to 10% $CO_2$ concentration under humidification, in a normal cell culturing incubator.

<2> Subculturing

After corneal endothelial cells subjected to culturing are grown, Subculturing may be conducted. Preferably, subculturing is conducted at the time of being sub-confluent or confluent. Subculturing may be conducted as follows. First, cells are treated with trypsin-EDTA or the like so that the cells are removed from the surface of a culture container. Then, the cells are collected. The culture normalizer or medium according to the present invention is added to the collected cells to obtain a cell suspension. It is preferable to conduct a centrifugal treatment when the cells are collected or after the collection. The subject centrifugal treatment allows for preparation of a cell suspension with a high cellular density. Preferable cellular density is about 1 to $2 \times 10^6$ cells/mL. Note that the conditions for the centrifugal treatment include, without limitation, for example, 500 rpm (30 g) to 1000 rpm (70 g), and 1 to 10 minutes.

The cell suspension is seeded to a culture container similar to the above-mentioned initial culture, thus being subjected to culturing. While the dilution rate at subculturing varies in accordance with the state of the cells, but it is about 1:2 to 1:4, and preferably 1:3. Subculturing may be conducted under culture conditions similar to the above-mentioned initial culture. The incubation time varies in accordance with the state of cells to be used or the like, but it is 7 to 30 days, for example. The above-mentioned subculturing may be conducted multiple times as needs arise. When a cell adhesion promoting agent (e.g., ROCK inhibitor or the like) is used in the agent, composition, medium or container according to the present invention, the cell adhesion in an initial period of the culture may be enhanced, making it possible to shorten the culture period.

<3> Preparation of Corneal Endothelial Cell Layer

The cell suspension is seeded onto a base material such as a collagen sheet, to be subjected to culturing. At this stage, the number of cells to be seeded is adjusted so that a desired cellular density of a cell layer is formed in a corneal endothelium formulation that is manufactured in the end. Specifically, the cells are seeded so that a cell layer of a cellular density within the range of about 1,000 to about 4,000 cells/mm$^2$ is formed. The culturing may be conducted under conditions similar to the above-mentioned initial culturing. The incubation time varies in accordance with the state of cells to be used, but it is, for example, 3 to 30 days.

By conducting the culture as described above, a corneal endothelium formulation is obtained, in which corneal endothelial cells layer cultured in the test tube is formed on the base material.

In the present invention, the corneal endothelium formulation may comprise the agent or composition according to the present invention, or a medium comprising any of them, or the corneal endothelium formulation may be maintained in a container containing any of them, in order to culture or grow corneal endothelial cells. The corneal endothelium formulation may comprise the agent or composition according to the present invention, or a medium comprising any of them, or the corneal endothelium formulation may be maintained in a container containing any of them, until being subjected to transplantation. The present invention may comprise a corneal endothelium formulation, the agent or composition according to the present invention, or a medium comprising any of them; and alternatively, the present invention provides a combination with a container comprising any of them.

The corneal endothelium formulation obtained by the manufacture method according to the present invention may be used as a graft in a treatment of diseases which require transplantation of corneal endothelium, such as bullous keratopathy, corneal edema, corneal leukoma, in particular, cornea dystrophy, and bullous keratopathy caused by corneal endothelium disorder due to external injury or internal ophthalmic surgery. The cause of such bullous keratopathy, corneal endothelium disorder or the like includes Fuchs' corneal endothelial dystrophy, pseudoexfoliation syndrome, corneal endotheliitis and the like, in addition to surgery.

The subject for the administration of the corneal endothelium formulation according to the present invention includes mammals (e.g., humans, mice, rats, hamsters, rabbits, cats, dogs, cows, sheep, monkeys and the like), and preferably, primate (e.g., humans).

(Treatment or Prevention of a Corneal Endothelial Disease, Disorder or Condition)

The present invention provides a medicament for treating or preventing a corneal endothelial disease, disorder or condition, comprising corneal endothelial cells produced by a method for culturing or growing a corneal endothelial cell, comprising a step of culturing corneal endothelial cells using an agent, composition, or medium or a container of the present invention. It is understood that an agent, composition, or medium or container of the present invention can be used in any form described herein. For example, the matters described herein, such as (Composition for culturing or growing a corneal endothelial cell), (Method of culturing a corneal endothelial cell) and (Corneal endothelial cell and corneal endothelial formulation) can be considered. Further, it is understood that corneal endothelial cells used as a medicament can take any form used herein. For example, the matter described in (Corneal endothelial cell and corneal endothelial formulation) can be considered.

In one embodiment, a medicament of the present invention is for the purpose of treating or preventing a corneal endothelium of primates. Preferably, the subject of such treatment or prevention is a human corneal endothelium.

In one embodiment, corneal endothelial cells used in a medicament of the present invention are from primates. Preferably, corneal endothelial cells used in a medicament of the present invention are from human.

In one embodiment, a corneal endothelial disease, disorder or condition targeted by a medicament of the present invention is bullous keratopathy, corneal endotheliitis, corneal edema, leukoma and the like.

In one embodiment, a medicament of the present invention is provided in a sheet form or as a suspension.

In one embodiment, a medicament of the present invention further comprises a cell adhesion promoting agent. A cell adhesion promoting agent exerts adhesion promoting action on corneal endothelial cells separated from a corneal tissue or corneal endothelial cells separated and subcultured. Such a cell adhesion promoting agent can be provided together with or separately from corneal endothelial cells provided as a medicament. In a specific embodiment, a cell adhesion promoting agent used in a medicament of the present invention includes a Rho kinase inhibitor. A Rho kinase inhibitor includes compounds disclosed in the following references: U.S. Pat. No. 4,678,783, Japanese Patent No. 3421217, International Publication No. WO 95/28387, International Publication No. WO 99/2062, International Publication No. WO 99/6140, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, and International Publication No. WO 2007/026664. Such compounds can be manufactured by methods described in each of the disclosed references and include, for example, 1-(5-Isoquinolinesulfonyl)homopiperazine or a salt thereof (e.g., fasudil(1-(5-Isoquinolinesulfonyl)homopiperazine)), and (+)-trans-4-(1-aminoethyl)-1-(4-pyridylcarbamoyl) cyclohexanecarboxamide or a salt thereof (e.g., Y-27632((R)-(+)-trans-(4-pyridyl)-4-(1-aminoethyl)-cyclohexanecarboxamide dihydrochloride monohydrate.

Targets of administration (transplant) of a medicament or method of the present invention include mammals (e.g., humans, mice, rats, hamsters, rabbits, cats, dogs, cows, sheep, monkeys and the like). However, primates are preferred and humans are preferred in particular. Satisfactory results have not been achieved in a corneal endothelial treatment for primates. In this sense, the present invention provides a ground-breaking therapeutic method and medicament.

In another aspect, the present invention provides a method for treating or preventing a corneal endothelial disease, disorder or condition, comprising a step of using corneal endothelial cells produced by a method for culturing corneal endothelial cells in a normal manner, comprising a step of culturing corneal endothelial cells using an agent, composition, medium, or a container of the present invention.

The mentioned references cited herein such as scientific publications, patents, and patent applications are incorporated by reference herein in their entirety in the same manner as the contents of each reference are specifically described therein.

As described above, the present invention has been described while presenting preferred embodiments to facilitate understanding. Hereinafter, the present invention will be described based on the Examples. However, the aforementioned description and the following Examples are provided for the sole purpose of exemplification and are not provided for the purpose of limiting the present invention. Thus, the scope of the present invention is limited solely by the Claims, not by the embodiments or the Examples specifically described herein.

EXAMPLES

Hereinafter, an example will be described where cells of corneal endothelial cells according to the present invention are normally cultured. When applicable, the standards set forth by Ministry of Health, Labour and Welfare, Ministry of Education, Culture, Sports, Science and Technology, or the like were observed for the handling of biological samples or the like, and when applicable, the handling was conducted based on Helsinki Declaration or the ethical provision created based on Helsinki Declaration. With regard to donation of eyes for studies, letters of consent were obtained from close relatives of all the deceased donors. The present study was approved by the ethical review of SightLife™ (Seattle, Wash.) eye bank.

(Experimental Method: Human Corneal Tissue of Study Grade)

Twelve human donor corneas were each obtained from the SightLife™ eye bank, and all the corneas were preserved in a preservation medium (Optisol; Chiron Vision Corporation, Irvine, Calif.) at 4° C. for a period of less than 14 days before the primary culture.

(Statistics Analysis)

The statistically-significant difference (P value) in an average value of a comparison of two samples was determined using t-test of Student's t-test. The statistically-significant difference in a comparison of a plurality of sample sets was analyzed using Dunnett's multiple comparison test. The values shown in the graph represent average±SE.

Example 1

Expression of a Laminin Chain and an Integrin Chain in Corneal Endothelial Cells and a Descemet's Membrane In the present Example, expression of a laminin chain in a Descemet's membrane, which is a basement membrane of a corneal endothelial cell, was observed.

(Materials and Methods)

Expression of laminin chain mRNA was conducted using a PCR method. Although data is not shown, expression of proteins is verified by immunostaining.

A secondary antibody was diluted with PBS and the resultant solution was incubated for thirty minutes at room temperature. Alexa™ Fluor 488 labeled (conjugated) Goat Anti-Rabbit IgG (Catalog Number: A11034; 1:1500; Molecular Probe-Invitrogen) was used as the secondary antibody. After shaking and washing twice with 0.15% Triton/PBS and once with PBS, nuclear staining was performed with propidium iodide (Catalog Number: SP29004-41; PI; Nacalai Tesque, Inc. Kyoto, Japan) and the secondary antibody was embedded by covering with a cover glass. The fluorescence-labelled secondary antibody was observed with a confocal laser scanning microscope (Olympus Fluoview, Tokyo, Japan) and a picture thereof was taken.

The sequences of primers of laminin chains used in a PCR method are shown in the following Table 1. The sequences of primers of integrin chains used in a PCR method are shown in the following Table 2. The primers were obtained from Life Technologies Japan Ltd (Catalog Number: 10336022).

TABLE 1

Oligonucleotide sequences for PCR

| Gene | Sense primer | Anti-sense primer | Size (bp) |
|---|---|---|---|
| Laminin α1 | 5'-GAGTCCGTCTCTCTGGACATAG-3' (SEQ ID NO: 9) | 5'-CGTGGCATTCACAGGGTTGAC-3' (SEQ ID NO: 10) | 180 |
| Laminin α2 | 5'-TGCTAGAATTTACCTCCGCTCG-3' (SEQ ID NO: 11) | 5'-GATCAAGTGGACAAGCCCTG-3' (SEQ ID NO: 12) | 203 |
| Laminin α3 | 5'-CTCCAAAGGCCCAACTCAAG-3' (SEQ ID NO: 13) | 5'-CCATAACTGCCTCCTTAGTCTC-3' (SEQ ID NO: 14) | 304 |
| Laminin α4 | 5'-CTTACGCAACACCACCGGATTC-3' (SEQ ID NO: 15) | 5'-CCTTCTTCCAAGCATTCTCCG-3' (SEQ ID NO: 16) | 140 |
| Laminin α5 | 5'-GAGGACTGAAGTGAAAACTCAA-3' (SEQ ID NO: 17) | 5'-CCACTGAAGTTGTAAATGGTG-3' (SEQ ID NO: 18) | 221 |
| Laminin β1 | 5'-GATGGTGAACTTGATGAAAAGT-3' (SEQ ID NO: 19) | 5'-GGCTTATATCCTTTAGGAGTGA-3' (SEQ ID NO: 20) | 258 |
| Laminin β2 | 5'-GATGATCGCATCCAAGGGAC-3' (SEQ ID NO: 21) | 5'-GTCCAGAGTAGGGAGTCTCAG-3' (SEQ ID NO: 22) | 150 |
| Laminin β3 | 5'-CCCAGATGGAGGAAGATGTC-3' (SEQ ID NO: 23) | 5'-GTAGCTGAGTCTGTGGGCAG-3' (SEQ ID NO: 24) | 144 |
| Laminin β4 | 5'-GGCAGGCTACTTTGGATTTC-3' (SEQ ID NO: 25) | 5'-GCTTGAGGGATCATCTGGAC-3' (SEQ ID NO: 26) | 204 |
| Laminin γ1 | 5'-GATGAGATGGTGACAGATCAAG-3' (SEQ ID NO: 27) | 5'-TTTCCAGTCTCTTCAATGGTAT-3' (SEQ ID NO: 28) | 199 |
| Laminin γ2 | 5'-ATCGAAGGTTACTGCGGAATC-3' (SEQ ID NO: 29) | 5'-GTAGCCAGAAGCACAATCCTG-3' (SEQ ID NO: 30) | 193 |
| Laminin γ3 | 5'-GGGATACAAGAGGGAGATGC-3' (SEQ ID NO: 31) | 5'-CATAGAAACCTGGCAAACAGC-3' (SEQ ID NO: 32) | 157 |

TABLE 2

Oligonucleotide sequences for PCR

| Gene | Sense primer | Anti-sense primer | Size (bp) |
|---|---|---|---|
| Integrin α1 | 5'-gaagaacctcctgaaacccttt-3' (SEQ ID NO: 33) | 5'-tgatgtcatattggggaatgaa-3' (SEQ ID NO: 34) | 254 |
| Integrin α2 | 5'-tgatgggacagaagtaacatgc-3' (SEQ ID NO: 35) | 5'-tggaccaacatcttcaaaactg-3' (SEQ ID NO: 36) | 333 |
| Integrin α3 | 5'-gctctgcctttggtttatctgt-3' (SEQ ID NO: 37) | 5'-ttcccactagaaggtctgggta-3' (SEQ ID NO: 38) | 257 |
| Integrin α4 | 5'-atattcagtcggagctggtcat-3' (SEQ ID NO: 39) | 5'-gcatatttgtcacttccaacga-3' (SEQ ID NO: 40) | 338 |
| Integrin α5 | 5'-tcctcagcaagaatctcaacaa-3' (SEQ ID NO: 41) | 5'-gttgagtcccgtaactctggtc-3' (SEQ ID NO: 42) | 304 |
| Integrin α6 | 5'-agcaaggcagatggaataatgt-3' (SEQ ID NO: 43) | 5'-cagggtaggaatttcgatcaag-3' (SEQ ID NO: 44) | 275 |
| Integrin α7 | 5'-caggtcaccttctacctcatcc-3' (SEQ ID NO: 45) | 5'-accgtgacctcatacttgacct-3' (SEQ ID NO: 46) | 262 |
| Integrin α8 | 5'-atggaaaatgtaaccaggatgg-3' (SEQ ID NO: 47) | 5'-cagttatgaatgggcagaacaa-3' (SEQ ID NO: 48) | 265 |
| Integrin α9 | 5'-cactttcagcccatcaatatca-3' (SEQ ID NO: 49) | 5'-acagtgtgctgttaggcaagaa-3' (SEQ ID NO: 50) | 305 |
| Integrin α10 | 5'-atcagtgtggttcagagggact-3' (SEQ ID NO: 51) | 5'-gccctggctttgtagtattgtc-3' (SEQ ID NO: 52) | 330 |

TABLE 2-continued

Oligonucleotide sequences for PCR

| Gene | Sense primer | Anti-sense primer | Size (bp) |
|---|---|---|---|
| Integrin α11 | 5'-ggacactgctgactacgtgaag-3' (SEQ ID NO: 53) | 5'-gcgtgtgctctctatgatgaag-3' (SEQ ID NO: 54) | 294 |
| Integrin αE | 5'-tagcagtgaagaagctgacgag-3' (SEQ ID NO: 55) | 5'-tctttcaggaagacgacagtga-3' (SEQ ID NO: 56) | 300 |
| Integrin αV | 5'-atctgtgaggtcgaaacaggat-3' (SEQ ID NO: 57) | 5'-accttgccaataaaagctacca-3' (SEQ ID NO: 58) | 255 |
| Integrin αL | 5'-gaaccattgacaccagaagtga-3' (SEQ ID NO: 59) | 5'-ttcttcaaaccccaactgtctt-3' (SEQ ID NO: 60) | 341 |
| Integrin αM | 5'-gatcggctaagagaaggacaga-3' (SEQ ID NO: 61) | 5'-cattgccacaattcttctcaaa-3' (SEQ ID NO: 62) | 330 |
| Integrin αX | 5'-ccaacatctgcctttacattga-3' (SEQ ID NO: 63) | 5'-cgtgaagtatctctgagcatcg-3' (SEQ ID NO: 64) | 331 |
| Integrin αD | 5'-ttaaccagatgaagggctttgt-3' (SEQ ID NO: 65) | 5'-ggtctttgtacttctgcccatc-3' (SEQ ID NO: 66) | 296 |
| Integrin αIIb | 5'-gaaaagactgaggaggctgaga-3' (SEQ ID NO: 67) | 5'-gagaaaatatccgcaactggag-3' (SEQ ID NO: 68) | 245 |
| Integrin β1 | 5'-gctgaagactatcccattgacc-3' (SEQ ID NO: 69) | 5'-atttccagatatgcgctgtttt-3' (SEQ ID NO: 70) | 321 |
| Integrin β2 | 5'-tgatggacctctcctactccat-3' (SEQ ID NO: 71) | 5'-gaaactggttggagttgttggt-3' (SEQ ID NO: 72) | 258 |
| Integrin β3 | 5'-tgtttaccactgatgccaagac-3' (SEQ ID NO: 73) | 5'-tcccataagcatcaacaatgag-3' (SEQ ID NO: 74) | 308 |
| Integrin β4 | 5'-gcttcacacctatttccctgtc-3' (SEQ ID NO: 75) | 5'-gaaggaaggtttcagatggatg-3' (SEQ ID NO: 76) | 316 |
| Integrin β5 | 5'-gctggtgttcacaacagatgat-3' (SEQ ID NO: 77) | 5'-atcccagactgacaactccact-3' (SEQ ID NO: 78) | 349 |
| Integrin β6 | 5'-tgtgactgtggtgaatgtgtgt-3' (SEQ ID NO: 79) | 5'-caccagctagtttgcacttgtc-3' (SEQ ID NO: 80) | 289 |
| Integrin β7 | 5'-cacttcagacgacacattccat-3' (SEQ ID NO: 81) | 5'-cccaactgcagacttaggaatc-3' (SEQ ID NO: 82) | 250 |
| Integrin β8 | 5'-gcattatgtcgaccaaacttca-3' (SEQ ID NO: 83) | 5'-atttcttcaggcttctcacgtc-3' (SEQ ID NO: 84) | 255 |

PCR Method: A PCR method was performed on each laminin chain and integrin chain by RT-PCR (semi-quantitative reverse transcription polymerase chain reaction). Primers were purchased from INVITROGEN, which is an oligonucleotide synthesizing company, and those on which a desalination treatment has been performed were used. RNEasy Mini Kit (QIAGEN Gmbh, Catalog Number: 74106) was used for the extraction of total RNA from cells. A Descemet's membrane including corneal endothelial cells was exfoliated from a cornea for research-use that was purchased from the Seattle Eye Bank and the corneal endothelial cells were mechanically exfoliated with the basement membrane to use in RNA extraction from the corneal endothelial cells. A reverse transcription reaction (42° C., sixty minutes) was performed on the RNA with ReverTra Ace (Toyobo Co., Ltd. (Catalog Number: TRT-101)), and CD166 and CD73 were amplified with GAPDH as an internal standard by using a TAKARA Taq HotStart Version of DNA polymerase (Takara Bio Inc. Catalog Number: RR001A). The same amount of cDNA was amplified by a PCR device (GeneAmp 9700; Applied Biosystems) and the following primer pair. In the PCR reaction, primers shown in Table 1, Table 2 and those described below were used.

```
                              (SEQ ID NO: 85)
*GAPDH-F:     GAGTCAACGGATTTGGTCGT (SEQ ID NO: 86)
*GAPDH-R:     TTGATTTTGGAGGGATCTCG
```

An amplified cDNA fragment was electrophoresed with 1.5% agarose gel (Nacalai Tesque, Catalog Number: 01149-76) and detected by staining with ethidium bromide (Nacalai Tesque, Catalog Number: 14603-51).

Flow cytometry: A cultured human corneal endothelium was seeded in a culture dish coated with FNC Coating and cultured for about 14 days until reaching confluent state under the condition of 5% $CO_2$ at 37° C. Cells were exfoliated with TrypLE™ Select and collected. Then, analysis on a surface antigen of an integrin chain was conducted by using a flow cytometer (BD FACSCanto™ II (BD Biosciences, Franklin Lakes, N.J.)) in accordance with the instruction manual while using Human Cell Surface Marker Screening Panel (BD Lyoplate™, BD Bio-sciences, Franklin Lakes, N.J.)).

A human corneal endothelial cell was cultured as described below. A Descemet's membrane including corneal endothelial cells was exfoliated from a cornea for research-use that was purchased from the Seattle Eye Bank and the corneal endothelial cell was mechanically exfoliated with the basement membrane. After detaching (typically, treated for two hours at 37° C. by using 1 mg/mL collagenase A (Roche Applied Science)) and collecting from the base membrane by using collagenase (ROCHE Catalog Number: 10 103 586 001), primary culture was conducted. For a medium, a medium in which the following was conditioned for a 3T3 feeder cell was used: Opti-MEM I Reduced-Serum Medium, Liquid (INVITROGEN, Catalog Number: 31985-070)+8% fetal bovine serum (FBS) (BIOWEST, Catalog Number: S1820-500)+200 mg/ml $CaCl_2.2H_2O$ (SIGMA Catalog Number: C7902-500G)+0.08% chondroitin sulfate (SIGMA Catalog Number: C9819-5G)+20 µg/ml ascorbic acid (SIGMA Catalog Number: A4544-25G)+50 µg/ml gentamicin (INVITROGEN Catalog Number: 15710-064)+5 ng/ml EGF (INVITROGEN Catalog Number: PHG0311). Specifically, after digestion at 37° C., HCEC obtained from individual cornea is resuspended in a culture medium and plated in one well of a 12-well plate coated with FNC Coating Mix™. The culture medium was prepared in accordance of a published protocol to which a partial alteration was added. Briefly explained, a base culture medium was prepared, containing OptiMEM-I (Life Technologies), 8% FBS, 5 ng/mL epidermal growth factor (EGF) (Sigma-Aldrich Co., St. Louis, Mo.), 1 µM SB431542 (Merck Millipore), 20 µg/mL ascorbic acid (Sigma-Aldrich), 200 mg/L calcium chloride (Sigma-Aldrich), 0.08% chondroitin sulfate (Wako Pure Chemical Industries, Ltd., Osaka) and 50 µg/mL gentamicin. Next, a conditioned medium was collected after culturing inactivated 3T3 fibroblasts. Inactivation of the 3T3 fibroblasts was performed as described above. Briefly explained, confluent 3T3 fibroblasts were incubated for two hours at 37° C. under 5% $CO_2$ with 4 µg/mL mitomycin C (MMC) (Kyowa Hakko Kirin Co., Ltd., Tokyo) and then the resultant was treated with trypsin and was plated on a plastic plate at a density of $2\times10^4$ cells/cm². HCEC was cultured under a humidified atmosphere at 37° C. in 5% $CO_2$, and the culture medium was replaced every three days. When HCEC reaches confluent state in 14 to 28 days, HCEC was rinsed in $Ca^{2+}$ and $Mg^{2+}$ free PBS, treated with trypsin with 0.05% trypsin-EDTA for five minutes at 37° C., and then subcultured at a ratio of 1:2.

(Results)

When expression of the laminin chain in the Descemet's membrane (corneal endothelial cell basement membrane) was observed, expression of laminin α5 chain, laminin β1 chain, and laminin γ1 chain was prominent. On the other hand, expression of laminin α1 chain, laminin α2 chain, and laminin α3 chain was not apparent (data not shown).

As shown in FIG. 1, when mRNA expression of laminin chains of human corneal endothelial cells was observed, expression of laminin α5 chain, laminin β1 chain, laminin β2 chain, and laminin γ1 chain was prominent. On the other hand, expression of laminin α1 chain, laminin α2 chain, laminin α3 chain, laminin α4 chain, laminin β3 chain, laminin γ2 chain, and laminin γ3 chain was not apparent.

As shown in FIG. 2, expression was recognized in integrin α1 chain, integrin α2 chain, integrin α3 chain, integrin α6 chain, integrin α10 chain, integrin α11 chain, integrin β1 chain, integrin β5 chain, integrin β8 chain, and integrin αV chain. Slight expression was also recognized in integrin β3 chain, integrin β4 chain, and integrin β6 chain. Thus, the above matter suggests that corneal endothelial cells express at least one of α1β1, α2β1, α1β1, α6β1, α7β1, and α6β4, which are integrins known as a laminin binding integrin.

As shown in FIG. 3 (FIGS. 3A, 3B and 3C), expression of integrin α1 chain, integrin α2 chain, integrin α3 chain, integrin α5 chain, and integrin β1 chain was recognized as an expression as a surface antigen.

Example 2

Promotion of Cell Adhesion of Human Corneal Endothelial Cells

In the present example, a culture container coated with laminin or the like was used to confirm as to whether or not cell adhesion would be made for human corneal endothelial cells.

(Material and Method)
laminin 511 (LN511, VERITAS Corporation)
laminin 521(LN521, VERITAS Corporation)
laminin 511-E8 fragment (382-02413, Nippi. Inc.)
FNC Coating Mix® (50 ml (AES-0407), ATHENA, catalogue number: 0407)
gelatine (G1890-500G, Sigma-Aldrich Co. LLC.)
container (3526, CORNING)

(Method) *Human Corneal Endothelial Cells (HCEC, Source and Culture Method): the culturing of HCEC was conducted as in Example 1 mentioned above. The cultured cells were rinsed in $Ca^{2+}$ and $Mg^{2+}$ free PBS, and trypsinized at 37° C. for five minutes with 0.05% trypsin-EDTA, followed by seeding to 12-well plates coated with FNC Coating Mix®. The culture medium was prepared in accordance with a publicly-released protocol with a partial alteration added thereto. Briefly speaking, a fundamental culture medium was prepared which contained OptiMEM-I (Life Technologies), 8% FBS, 5 ng/mL epidermal growth factor (EGF) (Sigma-Aldrich Co., St. Louis, Mo.), 10 µM SB431542 (Merck Millipore), 20 µg/mL ascorbic acid (Sigma-Aldrich), 200 mg/L calcium chloride (Sigma-Aldrich), 0.08% chondroitin sulfate (Wako Pure Chemical Industries, Ltd., Osaka) and 50 µg/mL gentamicin. Then, after the culturing of inactivated 3T3 fibroblast cells, the conditioned medium was retrieved. Inactivation of the 3T3 fibroblast cells was conducted as described previously. Briefly speaking, confluent 3T3 fibroblast cells were incubated together with 4 µg/mL mitomycin C (MMC) (Kyowa Hakko Kirin Col, Ltd, Tokyo) under 5% $CO_2$ at 37° C. for two hours, followed by trypsin treatment, and plating with the density of $2\times10^4$ cells/cm² on a plastic plate. The HCEC were cultured in 5% $CO_2$ at 37° C. in humidified atmosphere, and the culture medium was replaced every three days.

(Method) The HCEC were seeded to each well of 96-well plates coated with laminin 511, laminin 521, laminin 211, gelatine, FNC Coating Mix®, and the cell formed after 24 hours were observed using a phase-contrast microscope. Seeding was conducted with the seeding density of 5,000 cells/well to 96-well culture plates, and the number of adhered cells was examined at the point 24 hours after the cell seeding using CellTiter-Glo® Luminescent Cell Viability Assay (Promega Corporation, Madison, Wis., USA). In addition, the cell adhesion was evaluated for culture plates coated with laminin 511-E8 fragment (0.001-1.5 µg/cm$^2$). Further, various concentrations of laminin 521 and laminin 511-E8 fragments were added to media for seeding and the number of cells after 24 hours were similarly evaluated.

(Measurement of Cell Growth by BrdU Uptake)

Similarly, BrdU uptake of HCEC coated with various matrices was evaluated by ELISA. Seeding was conducted to 96-well culture plates with 5,000 cells/well seeding density, followed by culturing overnight. Then, 5-bromo-2'-deoxyuridine (BrdU) was added to the medium, followed by culturing overnight. The medium was removed, and fixative solution (Amersham cell proliferation biotrak ELISA system, version 2) was added for incubation for 30 minutes at a room temperature. Then, the fixative solution was removed, and a blocking solution (Amersham cell proliferation biotrak ELISA system, version 2) was added, followed by an incubation of 30 minutes at a room temperature. Then, the blocking solution was removed, and peroxidase conjugated anti-BrdU antibody was added, followed by an incubation of 90 minutes at a room temperature. The plates were washed three times with washing buffer, and TMB (3,3',5,5'-tetramethyl benzidine) matrix (Amersham cell proliferation biotrak ELISA system, version 2) was added, followed by an incubation of 5 to 30 minutes. The reaction was stopped using 1M sulfuric acid, and absorbance at 450 nm was measured using a plate reader. The result was shown as an average value of five measurements±standard error.

(Result)) As shown in FIG. 4, in the presence of laminin 511 and laminin 521, the adhesion and extension of corneal endothelial cells were favorable, while the growth was not favorable under other conditions.

Figure 5:
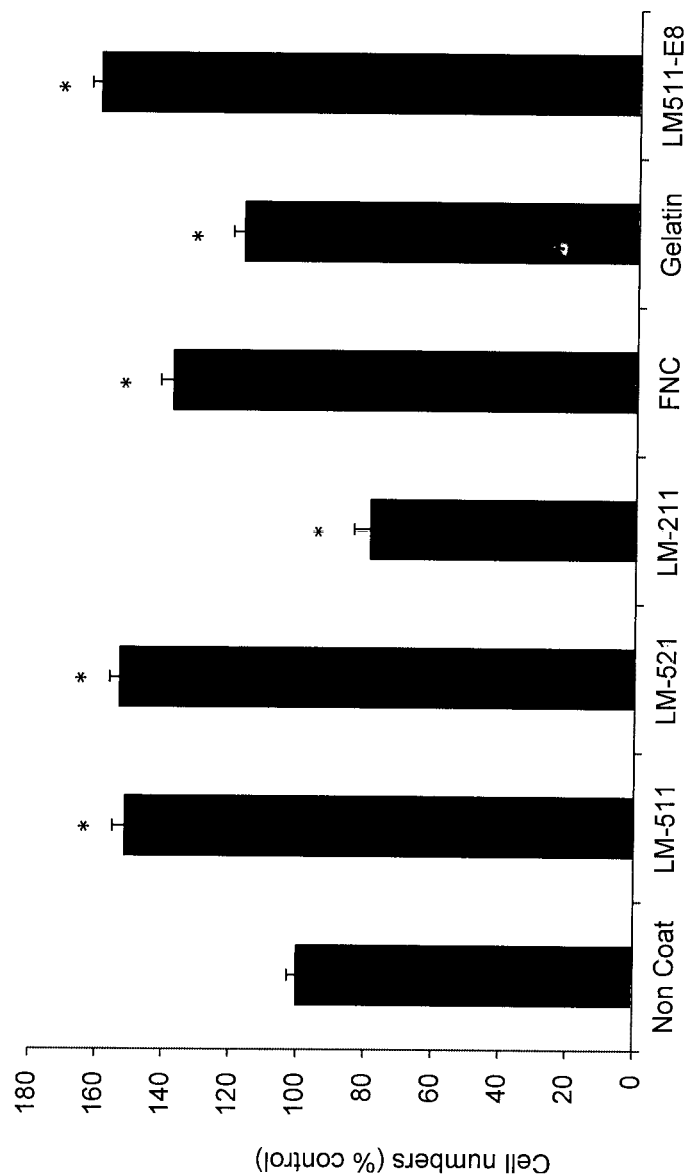
FIG. 5 is a graph showing that laminin 511 and laminin 521 promote cell adhesion of human corneal endothelial cells. The y-axis indicates the cell numbers (% control). The x-axis, from the left, indicates no coating (control), laminin 511, laminin 521, laminin 211, FNC coating, gelatin coating, and laminin 511-E8 fragment.

As shown in FIG. 5, in the presence of laminin 511 and laminin 521, the cell adhesion of corneal endothelial cells was shown to be favorable compared to other conditions.

Figure 6:
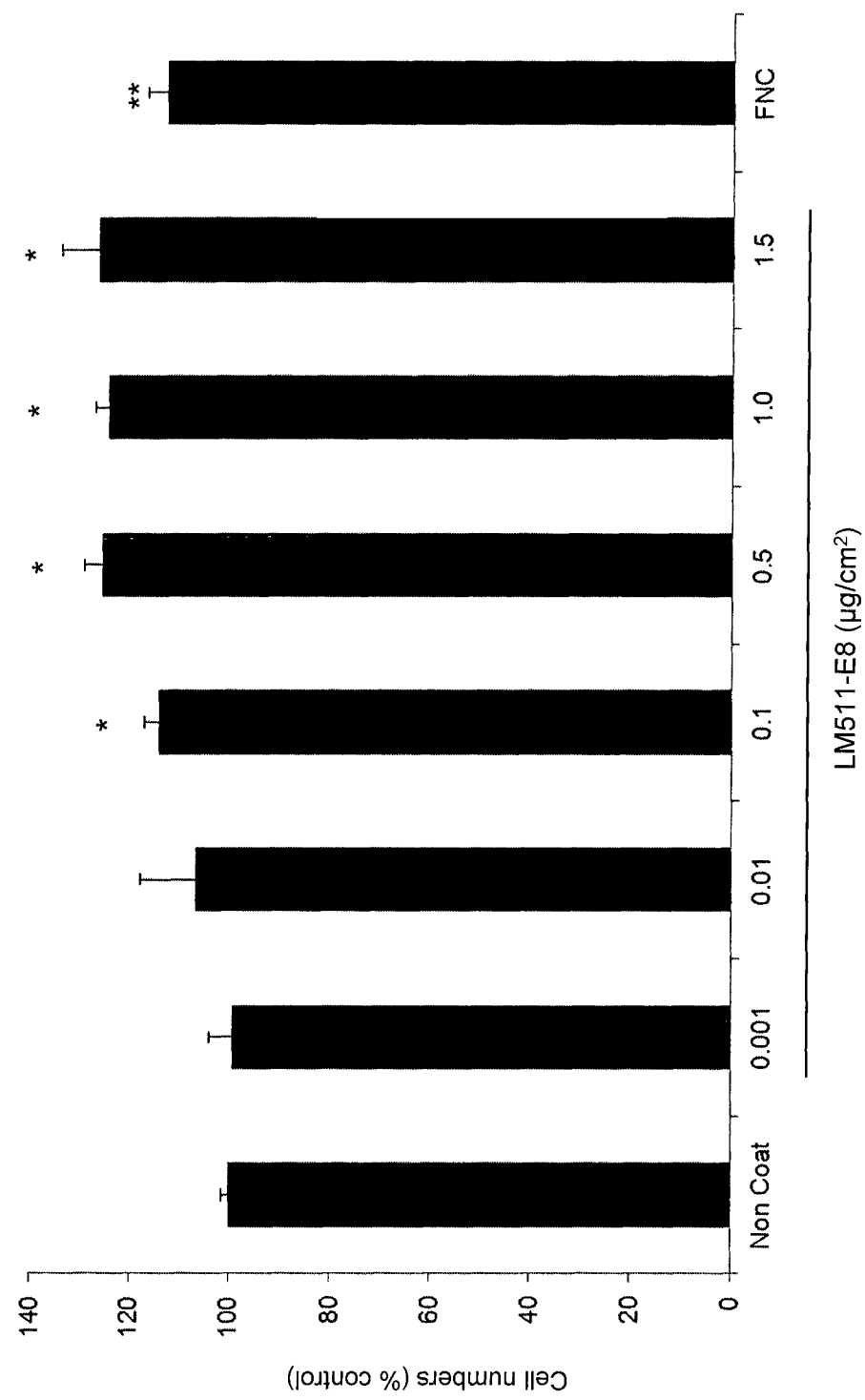
FIG. 6 is a graph showing that a laminin 511-E8 fragment promotes cell adhesion of human corneal endothelial cells. The y-axis indicates the number of cells (% control). The x-axis, from the left, indicates no coating (control), each concentration of laminin 511-E8 fragments (in order: 0.001 μg/cm$^2$, 0.01 μg/cm$^2$, 0.1 μg/cm$^2$, 0.5 μg/cm$^2$, 1.0 μg/cm$^2$, and 1.5 μg/cm$^2$), and FNC coating mix.

As shown in FIG. 6, in the presence of laminin 511-E8 fragment, the cell growth of corneal endothelial cells was shown to be favorable compared to other conditions. In particular, the cell adhesion was favorably promoted in the concentration of 0.1 to 1.5 µg/cm$^2$.

Figure 7:
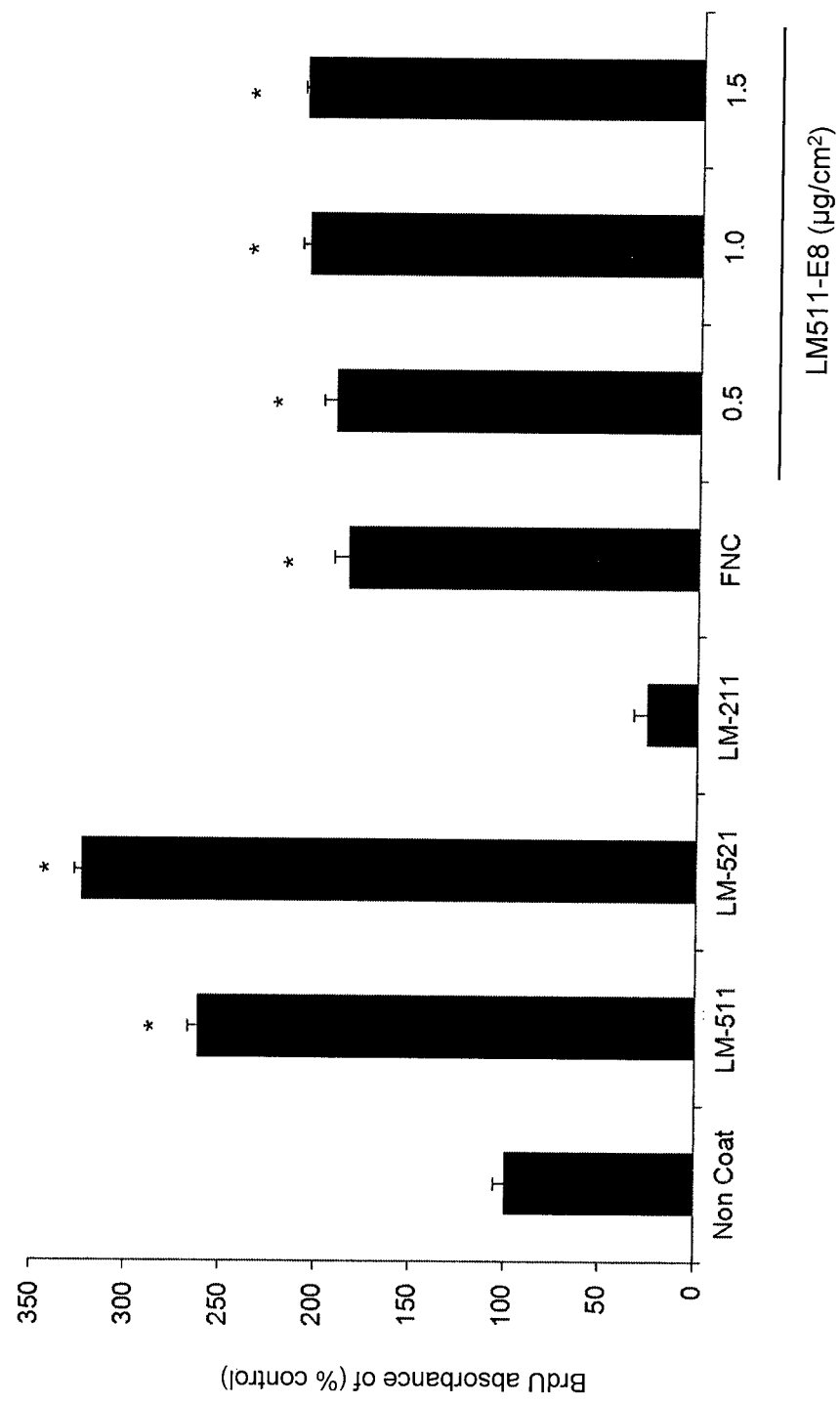
FIG. 7 is a graph showing that laminin 511, laminin 521, and laminin 511-E8 fragments promote cell adhesion of human corneal endothelial cells. The y-axis indicates the relative value (%) of BrdU absorbance with respect to a control. The x-axis, from the left, indicates no coating (control), laminin 511, laminin 521, laminin 211, FNC coating mix, and laminin 511-E8 fragments (from the left, 0.5 μg/cm$^2$, 1.0 μg/cm$^2$, and 1.5 μg/cm$^2$).

As shown in FIG. 7, in the presence of laminin 511, laminin 521 and laminin 511-E8 fragment, the cell growth of corneal endothelial cells was shown to be favorable compared to other conditions.

Example 3

Functional Analysis for Laminin 511 and Laminin 521 in Cell Culture of Human Corneal Endothelial Cells In the present example, functional analysis was conducted for laminin 511 and laminin 521 in cell culture of human corneal endothelial cells.

(Material and Method)

Human corneal endothelial cells (HCEC, Source and Culture Method): Culturing of the HCEC was conducted as follows. Briefly speaking, Descemet's membrane including corneal endothelial cells were exfoliated from the corneas for research-use purchased from the Seattle Eye Bank; the basement membrane was then mechanically exfoliated together with the corneal endothelial cells, which were then exfoliated from the basement membrane using collagenase (ROCHE catalogue number: 10 103 586 001) (typically, they were treated for two hours using 1 mg/mL collagenase A(Roche Applied Science) at 37° C.). After the retrieval, the primary culture was conducted. At the primary culture, plating was conducted to 1 well out of 12-well plates coated with laminin 511, laminin 521, laminin 211, FNC Coating Mix®. For the medium, the same one as in Example 1 was used. Cell observation was conducted over a period of time using a phase-contrast microscope.

Cell observing method for staining or the like (histological test): after immobilizing the cultured HCEC, immunostaining was conducted using ZO-1, Na$^+$/K$^+$-ATPase as a function-related marker followed by observation using a fluorescence microscope. The HCEC were immobilized with 4% formaldehyde for 10 minutes at room temperature (RT), followed by incubation with 1% bovine serum albumin (BSA) for 30 minutes. Immune tissue chemical analysis was conducted for tight junction-related protein, ZO-1, and protein related to pumping function, Na$^+$/K$^+$-ATPase. Each of the primary antibodies was used in a 1:200 dilution. For secondary antibody, 1:2000 dilution of Alexa Fluor™ 488 labelled or Alexa Fluor™ 594 labelled goat anti-mouse IgG (Life Technologies) was used. Then, cell nuclei were stained with DAPI (Vector Laboratories, Inc., Burlingame, Calif.). Then, slides were observed using a fluorescence microscope (BZ-9000; Keyence, Osaka, Japan).

Antibodies to Na$^+$/K$^+$-ATPase: those made by MILLIPORE (MILLIPORE catalogue number: 05-369) were used.

Antibodies to ZO-1: those made by Rabbit ZYMED LABORATORIES (ZYMED LABORATORIES catalogue number: 61-7300) were used.

(Result)

As shown in FIG. 8, the laminin 511 and laminin 521 were shown to make cell culturing of human corneal endothelial cells more efficient. The photographs show cells two days after the primary culture through a phase-contrast microscope.

Figure 9:
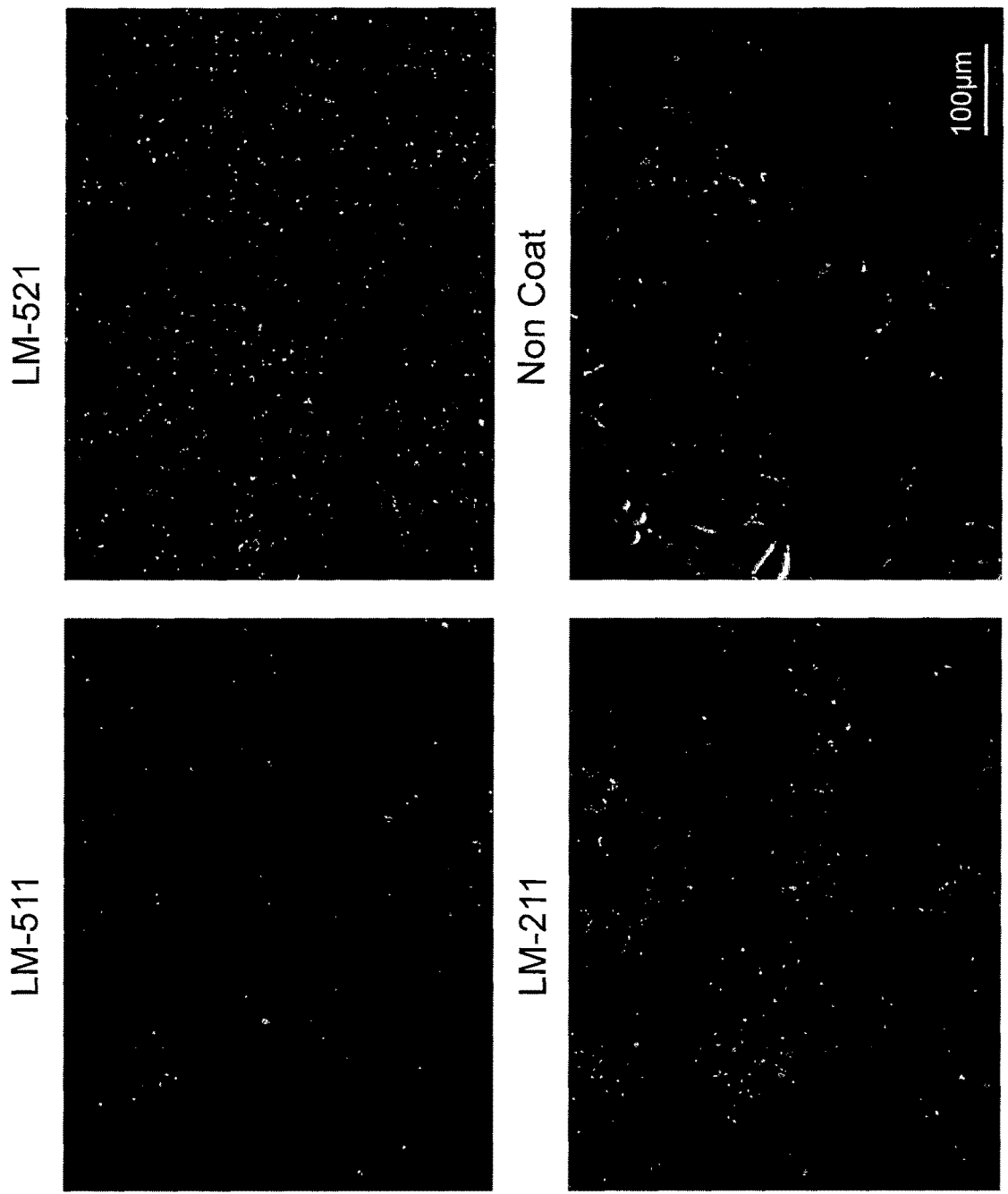
FIG. 9 is a picture from a phase-contrast microscope on day 20 of culture, showing that laminin 511 and laminin 521 enable culturing human corneal endothelial cells at a high cellular density. Top left shows laminin 511, top right shows laminin 521, bottom left shows laminin 211, and bottom right shows no coating. The bar indicates 100 μm.

As shown in FIG. 9, the laminin 511 and laminin 521 were shown to allow for cell culturing of human corneal endothelial cells with high cell density. The photographs show cells twenty days after the primary culture through a phase-contrast microscope.

Figure 11:
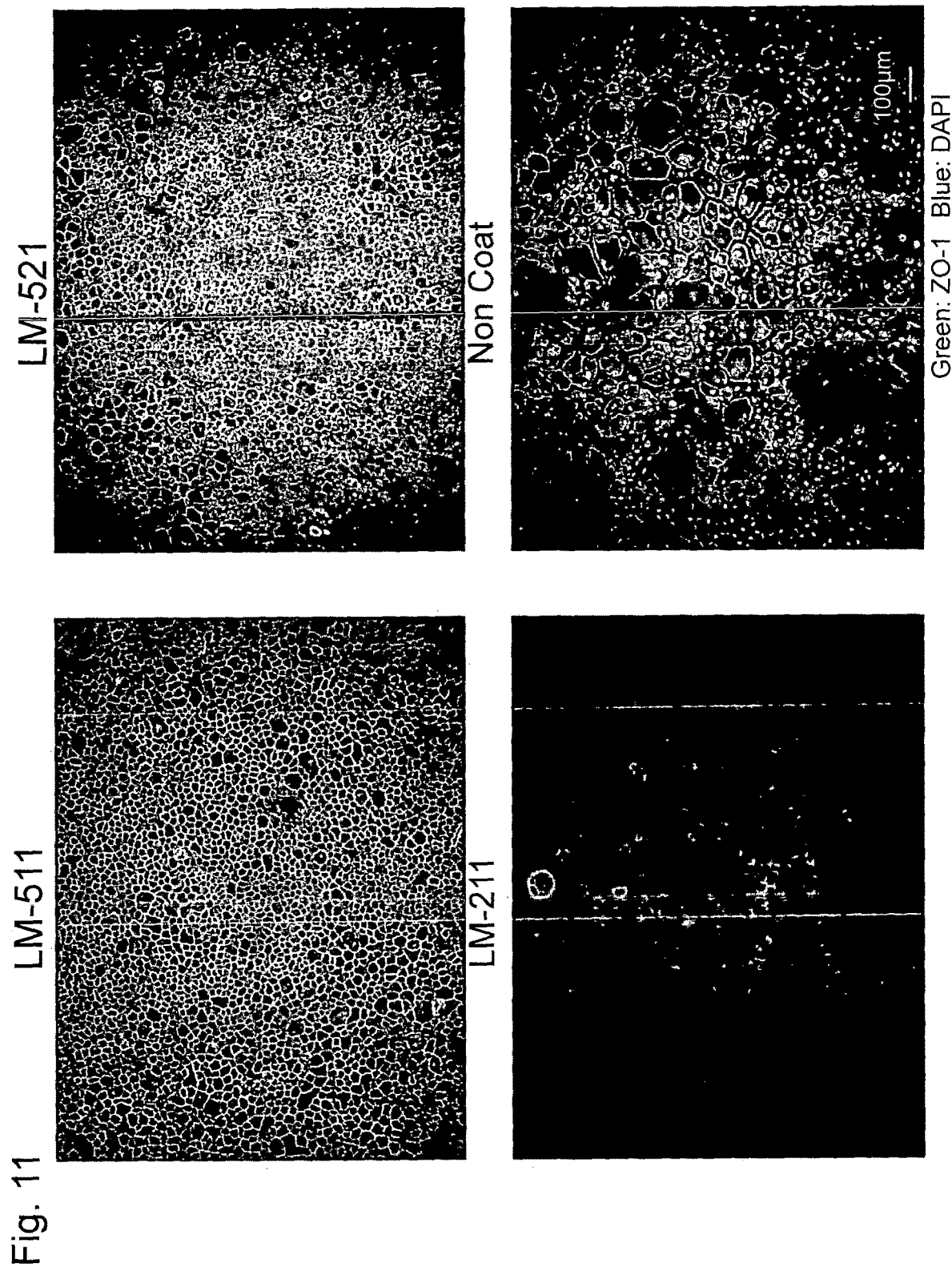
FIG. 11 is a picture showing that laminin 511 and laminin 521 enable culturing human corneal endothelial cells at a high cellular density. The green dye indicates ZO-1 and the blue dye indicates DAPI. The top left shows laminin 511, top right shows laminin 521, bottom left shows laminin 211, and bottom right shows no coating. The bar indicates 100 μm.

As shown in FIGS. 10 and 11, laminin 511 and laminin 521 were shown to retain the activity of ZO-1 and Na$^+$/K$^+$-ATPase, and it was demonstrated that culturing using the method according to the present invention allows for growing while maintaining normal functions. The cell density in laminin 511 and laminin 521 was higher compared to laminin 211 and non-coated control.

Figure 12:
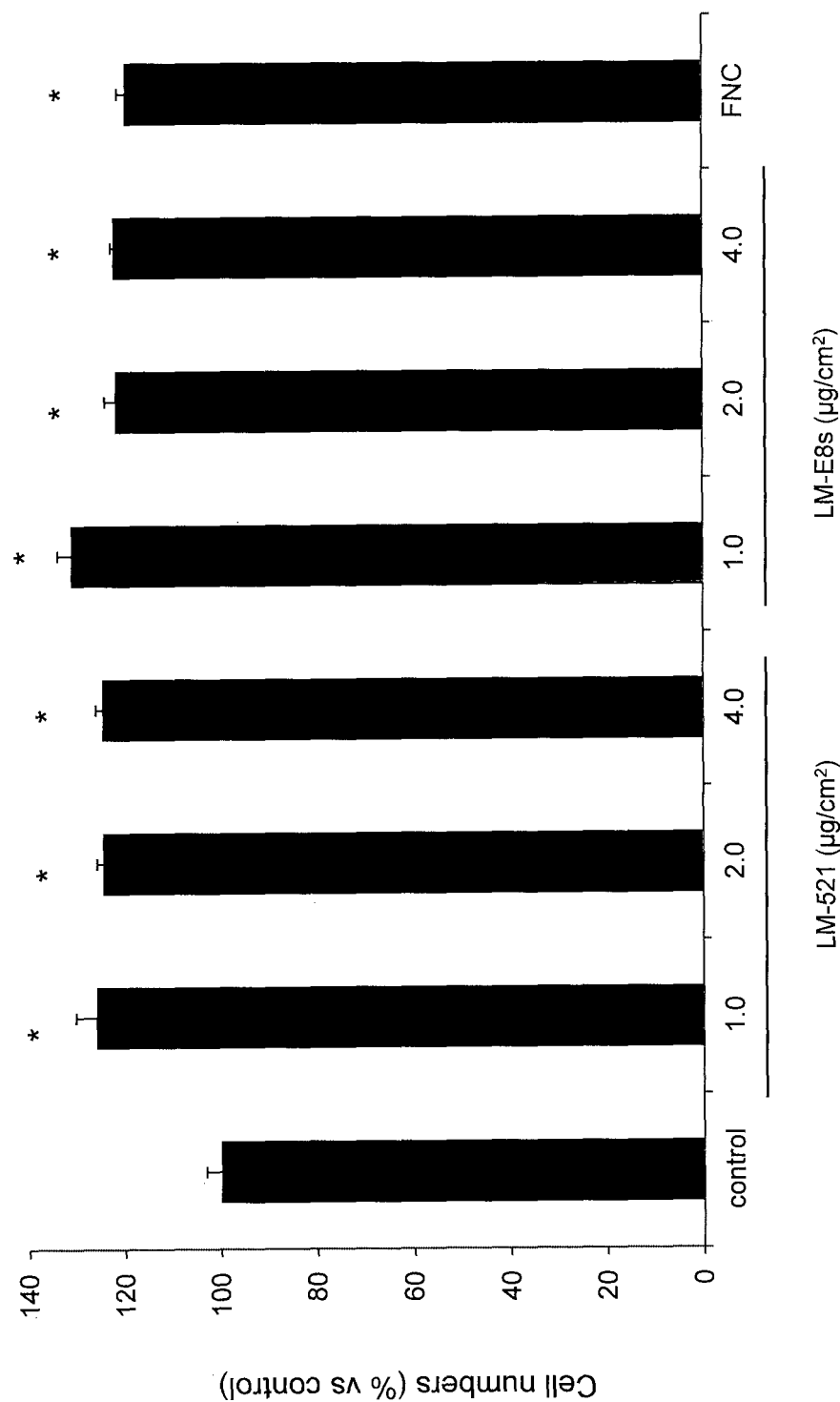
FIG. 12 is a graph indicating that cell adhesion of a human corneal endothelial cell is promoted even in a culture in which laminin 521 and laminin 511-E8 fragment are added to a culture medium. The y-axis indicates the number of cells (% control). The x-axis, from the left, indicates no coating (control), each concentration of laminin 521 (in order: 1.0 μg/cm$^2$, 2.0 μg/cm$^2$ and 4.0 μg/cm$^2$), each concentration of laminin 511-E8 fragments (in order: 1.0 μg/cm$^2$, 2.0 μg/cm$^2$ and 4.0 μg/cm$^2$), and FNC coating mix.

As shown in FIG. 12, laminin 521 and laminin 511-E8 fragment of various concentrations were added to media to be seeded, thus promoting the cell adhesion of the corneal endothelial cells.

Example 4

Exemplary Formulations: Culture Solution for Preparing a Corneal Endothelial Sheet In the present Example, as a formulation example, a culture solution for preparing a corneal endothelium sheet containing an agent of the present invention is manufactured as follows.

A culture solution shown below is prepared with a conventional method.

| | |
|---|---|
| Laminin 511, laminin 521 and/or a fragment thereof | (0.75 μg/cm$^2$) |
| Fetal bovine serum (FBS) | 10 mL |
| penicillin-streptomycin solution | 1 mL |
| FGF basic | 200 ng |
| DMEM | appropriate amount |
| total amount | 100 mL |

For example, BIOWEST (Catalog Number: S1820-500) or those manufactured by Invitrogen can be used for the FBS. For the penicillin-streptomycin solution, those manufactured by Nacalai Tesque (containing penicillin 5000 μg/mL, streptomycin 5000 μg/mL) can be used. In addition, for example, for the FGF basic, those manufactured by Invitrogen (INVITROGEN, Catalog Number: 13256-029) can be used. For SB431542, those manufactured by Tocris Cookson Ltd, and for SB203580, those of CALBIOCHEM brand can be used. For DMEM, those manufactured by Invitrogen can be used.

Example 5

Exemplary Formulations: Composition for a Container for Preserving or Amplifying a Cornea In the present Example, as an example of a formulation, a solution for coating a container comprising an agent of the present invention is manufactured as follows.

A preservation solution shown below is prepared by a conventional method.

| | |
|---|---|
| Laminin 511, laminin 521 and/or a fragment thereof | (0.75 μg/cm$^2$) |
| Appropriate buffer | appropriate amount |
| Total amount | 100 mL |

Each ingredient can be obtained similarly to Example 4.

As described above, the present invention is exemplified by the use of preferred embodiments of the present invention. However, it is understood that the scope of the present invention should be interpreted solely based on the claims. Further, it is understood that any patent, any patent application and any references cited herein should be incorporated by reference herein in the same manner as the contents are specifically described therein. The subject application claims priority on Japanese Patent Application No. 2013-244972 filed on Nov. 27, 2013, which should be herein incorporated by reference in its entirety.

INDUSTRIAL APPLICABILITY

Culture components and a culture method for promoting growth of corneal endothelium cells are provided. A technique available in the industry associated with a technique related to corneal implants (cell culturing industry, drug manufacturing and the like) is provided.

SEQUENCE LISTING FREE TEXT

SEQ ID NO: 1 laminin α5 chain nucleic acid sequence (NM_005560)
SEQ ID NO: 2 laminin α5 chain amino acid sequence (NP_005551)
SEQ ID NO: 3 laminin β1 chain nucleic acid sequence (NM_002291)
SEQ ID NO: 4 laminin β1 chain amino acid sequence (NP_002282)
SEQ ID NO: 5 laminin β2 chain nucleic acid sequence (NM_002292)
SEQ ID NO: 6 laminin β2 chain amino acid sequence (NP_002283)
SEQ ID NO: 7 laminin γ1 chain nucleic acid sequence (NM_002293)
SEQ ID NO: 8 laminin γ1 chain amino acid sequence (NP_002284)
SEQ ID NO: 9 laminin α1 chain sense primer sequence: 5'-GAGTCCGTCTCTCTGGACATAG-3'
SEQ ID NO: 10 laminin α1 chain antisense primer sequence: 5'-CGTGGCATTCACAGGGTTGAC-3'
SEQ ID NO: 11 laminin α2 chain sense primer sequence: 5'-TGCTAGAATTTACCTCCGCTCG-3'
SEQ ID NO: 12 laminin α2 chain antisense primer sequence: 5'-GATCAAGTGGACAAGCCCTG-3'
SEQ ID NO: 13 laminin α3 chain sense primer sequence: 5'-CTCCAAAGGCCCAACTCAAG-3'
SEQ ID NO: 14 laminin α3 chain antisense primer sequence: 5'-CCATAACTGCCTCCTTAGTCTC-3'
SEQ ID NO: 15 laminin α4 chain sense primer sequence: 5'-CTTACGCAACACCACCGGATTC-3'
SEQ ID NO: 16 laminin α4 chain antisense primer sequence: 5'-CCTTCTTCCAAGCATTCTCCG-3'
SEQ ID NO: 17 laminin α5 chain sense primer sequence: 5'-GAGGACTGAAGTGAAAACTCAA-3'
SEQ ID NO: 18 laminin α5 chain antisense primer sequence: 5'-CCACTGAAGTTGTAAATGGTG-3'
SEQ ID NO: 19 laminin β1 chain sense primer sequence: 5'-GATGGTGAACTTGATGAAAAGT-3'
SEQ ID NO: 20 laminin β1 chain antisense primer sequence: 5'-GGCTTATATCCTTTAGGAGTGA-3'
SEQ ID NO: 21 laminin β2 chain sense primer sequence: 5'-GATGATCGCATCCAAGGGAC-3'
SEQ ID NO: 22 laminin β2 chain antisense primer sequence: 5'-GTCCAGAGTAGGGAGTCTCAG-3'
SEQ ID NO: 23 laminin β3 chain sense primer sequence: 5'-CCCAGATGGAGGAAGATGTC-3'
SEQ ID NO: 24 laminin β3 chain antisense primer sequence: 5'-GTAGCTGAGTCTGTGGGCAG-3'
SEQ ID NO: 25 laminin β4 chain sense primer sequence: 5'-GGCAGGCTACTTTGGATTTC-3'
SEQ ID NO: 26 laminin β4 chain antisense primer sequence: 5'-GCTTGAGGGATCATCTGGAC-3'
SEQ ID NO: 27 laminin γ1 chain sense primer sequence: 5'-GATGAGATGGTGACAGATCAAG-3'
SEQ ID NO: 28 laminin γ1 chain antisense primer sequence: 5'-TTTCCAGTCTCTTCAATGGTAT-3'
SEQ ID NO: 29 laminin γ2 chain sense primer sequence: 5'-ATCGAAGGTTACTGCGGAATC-3'
SEQ ID NO: 30 laminin γ2 chain antisense primer sequence: 5'-GTAGCCAGAAGCACAATCCTG-3'
SEQ ID NO: 31 laminin γ3 chain sense primer sequence: 5'-GGGATACAAGAGGGAGATGC-3'
SEQ ID NO: 32 laminin γ3 chain antisense primer sequence: 5'-CATAGAAACCTGGCAAACAGC-3'
SEQ ID NO: 33 integrin α1 chain sense primer sequence: 5'-gaagaacctcctgaaaccctt-3'
SEQ ID NO: 34 integrin α1 chain antisense primer sequence: 5'-tgatgtcatattggggaatgaa-3'
SEQ ID NO: 35 integrin α2 chain sense primer sequence: 5'-tgatgggacagaagtaacatgc-3'
SEQ ID NO: 36 integrin α2 chain antisense primer sequence: 5'-tggaccaacatcttcaaaactg-3'

SEQ ID NO: 37 integrin α3 chain sense primer sequence: 5'-gctctgcctttggtttatctgt-3'

SEQ ID NO: 38 integrin α3 chain antisense primer sequence: 5'-ttcccactagaaggtctgggta-3'

SEQ ID NO: 39 integrin α4 chain sense primer sequence: 5'-atattcagtcggagctggtcat-3'

SEQ ID NO: 40 integrin α4 chain antisense primer sequence: 5'-gcatatttgtcacttccaacga-3'

SEQ ID NO: 41 integrin α5 chain sense primer sequence: 5'-tcctcagcaagaatctcaacaa-3'

SEQ ID NO: 42 integrin α5 chain antisense primer sequence: 5'-gttgagtcccgtaactctggtc-3'

SEQ ID NO: 43 integrin α6 chain sense primer sequence: 5'-agcaaggcagatggaataatgt-3'

SEQ ID NO: 44 integrin α6 chain antisense primer sequence: 5'-cagggtaggaatttcgatcaag-3'

SEQ ID NO: 45 integrin α7 chain sense primer sequence: 5'-caggtcaccttctacctcatcc-3'

SEQ ID NO: 46 integrin α7 chain antisense primer sequence: 5'-accgtgacctcatacttgacct-3'

SEQ ID NO: 47 integrin α8 chain sense primer sequence: 5'-atggaaaatgtaaccaggatgg-3'

SEQ ID NO: 48 integrin α8 chain antisense primer sequence: 5'-cagttatgaatgggcagaacaa-3'

SEQ ID NO: 49 integrin α9 chain sense primer sequence: 5'-cactttcagcccatcaatatca-3'

SEQ ID NO: 50 integrin α9 chain antisense primer sequence: 5'-acagtgtgctgttaggcaagaa-3'

SEQ ID NO: 51 integrin α10 chain sense primer sequence: 5'-atcagtgtggttcagagggact-3'

SEQ ID NO: 52 integrin α10 chain antisense primer sequence: 5'-gccctggctttgtagtattgtc-3'

SEQ ID NO: 53 integrin α11 chain sense primer sequence: 5'-ggacactgctgactacgtgaag-3'

SEQ ID NO: 54 integrin α11 chain antisense primer sequence: 5'-gcgtgtgctctctatgatgaag-3'

SEQ ID NO: 55 integrin αE chain sense primer sequence: 5'-tagcagtgaagaagctgacgag-3'

SEQ ID NO: 56 integrin αE chain antisense primer sequence: 5'-tctttcaggaagacgacagtga-3'

SEQ ID NO: 57 integrin αV chain sense primer sequence: 5'-atctgtgaggtcgaaacaggat-3'

SEQ ID NO: 58 integrin αV chain antisense primer sequence: 5'-accttgccaataaaagctacca-3'

SEQ ID NO: 59 integrin αL chain sense primer sequence: 5'-gaaccattgacaccagaagtga-3'

SEQ ID NO: 60 integrin αL chain antisense primer sequence: 5'-ttcttcaaacccccaactgtctt-3'

SEQ ID NO: 61 integrin αM chain sense primer sequence: 5'-gatcggctaagagaaggacaga-3'

SEQ ID NO: 62 integrin αM chain antisense primer sequence: 5'-cattgccacaattcttctcaaa-3'

SEQ ID NO: 63 integrin αX chain sense primer sequence: 5'-ccaacatctgcctttacattga-3'

SEQ ID NO: 64 integrin αX chain antisense primer sequence: 5'-cgtgaagtatctctgagcatcg-3'

SEQ ID NO: 65 integrin αD chain sense primer sequence: 5'-ttaaccagatgaagggctttgt-3'

SEQ ID NO: 66 integrin αD chain antisense primer sequence: 5'-ggtctttgtacttctgcccatc-3'

SEQ ID NO: 67 integrin αIIb chain sense primer sequence: 5'-gaaaagactgaggaggctgaga-3'

SEQ ID NO: 68 integrin αIIb chain antisense primer sequence: 5'-gagaaaatatccgcaactggag-3'

SEQ ID NO: 69 integrin β1 chain sense primer sequence: 5'-gctgaagactatcccattgacc-3'

SEQ ID NO: 70 integrin β1 chain antisense primer sequence: 5'-atttccagatatgcgctgtttt-3'

SEQ ID NO: 71 integrin β2 chain sense primer sequence: 5'-tgatggacctctcctactccat-3'

SEQ ID NO: 72 integrin β2 chain antisense primer sequence: 5'-gaaactggttggagttgttggt-3'

SEQ ID NO: 73 integrin β3 chain sense primer sequence: 5'-tgtttaccactgatgccaagac-3'

SEQ ID NO: 74 integrin β3 chain antisense primer sequence: 5'-tcccataagcatcaacaatgag-3'

SEQ ID NO: 75 integrin β4 chain sense primer sequence: 5'-gcttcacacctatttccctgtc-3'

SEQ ID NO: 76 integrin β4 chain antisense primer sequence: 5'-gaaggaaggtttcagatggatg-3'

SEQ ID NO: 77 integrin β5 chain sense primer sequence: 5'-gctggtgttcacaacagatgat-3'

SEQ ID NO: 78 integrin β5 chain antisense primer sequence: 5'-atcccagactgacaactccact-3'

SEQ ID NO: 79 integrin β6 chain sense primer sequence: 5'-tgtgactgtggtgaatgtgtgt-3'

SEQ ID NO: 80 integrin β6 chain antisense primer sequence: 5'-caccagctagtttgcacttgtc-3'

SEQ ID NO: 81 integrin β7 chain sense primer sequence: 5'-cacttcagacgacacattccat-3'

SEQ ID NO: 82 integrin β7 chain antisense primer sequence: 5'-cccaactgcagacttaggaatc-3'

SEQ ID NO: 83 integrin β8 chain sense primer sequence: 5'-gcattatgtcgaccaaacttca-3'

SEQ ID NO: 84 integrin β8 chain antisense primer sequence: 5'-atttcttcaggcttctcacgtc-3'

SEQ ID NO: 85 GAPDH-F: GAGTCAACGGATTTGGTCGT

SEQ ID NO: 86 GAPDH-R: TTGATTTTGGAGGGATCTCG

The invention claimed is:

1. A method for promoting growth of differentiated corneal endothelial cells comprising contacting the cells in a culture container with a composition comprising from 0.1 µg/cm² to less than 1.5 µg/cm² of laminin 511-E8 fragment.

2. The method of claim 1, wherein the differentiated corneal endothelial cells are isolated from human cornea.

3. A method for promoting growth of differentiated corneal endothelial cells comprising contacting the cells in a culture container with a composition comprising 0.1-1 µg/cm² of laminin 511-E8 fragment.

* * * * *